(12) United States Patent
Whalen et al.

(10) Patent No.: US 11,730,489 B1
(45) Date of Patent: Aug. 22, 2023

(54) BLOOD FLOW RESTRICTION BELTS AND SYSTEM

(71) Applicants: Robert Tremaine Whalen, Los Altos, CA (US); Sean Tremaine Whalen, Mountain View, CA (US); James Stray-Gundersen, Park City, UT (US)

(72) Inventors: Robert Tremaine Whalen, Los Altos, CA (US); Sean Tremaine Whalen, Mountain View, CA (US); James Stray-Gundersen, Park City, UT (US)

( * ) Notice: Subject to any disclaimer, the term of this patent is extended or adjusted under 35 U.S.C. 154(b) by 0 days.

(21) Appl. No.: 16/833,554

(22) Filed: Mar. 28, 2020

Related U.S. Application Data

(63) Continuation of application No. 15/430,404, filed on Feb. 10, 2017, now abandoned.

(60) Provisional application No. 62/311,936, filed on Mar. 23, 2016, provisional application No. 62/293,536, filed on Feb. 10, 2016.

(51) Int. Cl.
*A61B 17/135* (2006.01)
*A61B 17/132* (2006.01)

(52) U.S. Cl.
CPC ........ *A61B 17/1355* (2013.01); *A61B 17/135* (2013.01); *A61B 17/1322* (2013.01)

(58) Field of Classification Search
CPC . A61B 17/132–17/1355; A61H 9/0078; A61H 2201/165; A61H 2205/06; A61H 2205/10106; A61H 2205/108; A63B 21/0085; A63B 21/4025; A63B 2225/62
See application file for complete search history.

(56) References Cited

U.S. PATENT DOCUMENTS

| | | | | |
|---|---|---|---|---|
| 2,045,750 A | * | 6/1936 | Buschenfeldt | A61B 17/135 606/202 |
| 3,570,495 A | * | 3/1971 | Wright | A61B 17/135 606/202 |
| 4,198,031 A | * | 4/1980 | Ezekiel | A61B 5/0235 137/844 |
| 4,616,434 A | * | 10/1986 | Riba | D06F 81/14 38/140 |
| 4,682,588 A | * | 7/1987 | Curlee | A61F 5/028 128/DIG. 20 |
| 4,791,236 A | * | 12/1988 | Klein | H01B 7/186 174/DIG. 11 |
| 5,007,411 A | * | 4/1991 | Dye | A61H 9/0078 601/151 |
| 5,451,234 A | * | 9/1995 | Wassermann | A61B 17/1327 606/203 |

(Continued)

*Primary Examiner* — Kathleen S Holwerda
(74) *Attorney, Agent, or Firm* — Snell & Wilmer L.L.P.

(57) ABSTRACT

An inflatable belt 100 for use in a BFR system with an outer belt material 102 hermetically sealed to an inner belt material 101 along a perimeter, thereby forming at least one inflatable chamber 103, the inflatable chamber having an input port 104 for accepting a gas into the chamber, the inflatable belt further comprising a first fastening means 110 in communication with the outer belt material, for attaching to a second fastening means 111 in communication with the outer belt material, thereby locking a circumference of the inflatable belt when wrapped around a user's limb, the inflatable belt providing sufficient volume and compliance so as to reduce spikes in pressure and thereby improve comfort and safety of the inflatable belt for use in restriction of blood flow for muscle development.

16 Claims, 27 Drawing Sheets

(56) References Cited

U.S. PATENT DOCUMENTS

| | | | | |
|---|---|---|---|---|
| 5,618,302 A * | 4/1997 | Martin | | A61F 2/0054 |
| | | | | 606/201 |
| 7,455,630 B2 * | 11/2008 | Sato | | A63B 21/4025 |
| | | | | 482/111 |
| 8,652,164 B1 * | 2/2014 | Aston | | A61B 17/1327 |
| | | | | 606/203 |
| 10,136,900 B2 * | 11/2018 | Menashe | | A61K 45/06 |
| 2002/0010060 A1 * | 1/2002 | Bray | | A63B 23/0211 |
| | | | | 482/140 |
| 2002/0120288 A1 * | 8/2002 | Dedo | | A61B 17/1322 |
| | | | | 606/203 |
| 2003/0139766 A1 * | 7/2003 | McEwen | | A61B 17/135 |
| | | | | 606/202 |
| 2005/0159690 A1 * | 7/2005 | Barak | | A61H 9/0078 |
| | | | | 601/149 |
| 2005/0187501 A1 * | 8/2005 | Ravikumar | | A61F 13/085 |
| | | | | 601/152 |
| 2006/0211976 A1 * | 9/2006 | Ramsey | | A61B 17/1322 |
| | | | | 602/75 |
| 2006/0281611 A1 * | 12/2006 | Sato | | A63B 23/035 |
| | | | | 482/148 |
| 2007/0032819 A1 * | 2/2007 | McEwen | | A61B 17/1322 |
| | | | | 606/202 |
| 2011/0077566 A1 * | 3/2011 | Ganapathy | | A61H 9/0092 |
| | | | | 602/13 |
| 2011/0160022 A1 * | 6/2011 | Sato | | A63B 21/4025 |
| | | | | 482/113 |
| 2012/0046582 A1 * | 2/2012 | Hopman | | A61B 17/1327 |
| | | | | 602/5 |
| 2012/0065561 A1 * | 3/2012 | Ballas | | A61H 9/0092 |
| | | | | 601/152 |
| 2013/0190806 A1 * | 7/2013 | McEwen | | A61B 8/4227 |
| | | | | 606/202 |
| 2014/0228732 A1 * | 8/2014 | Steinbaugh | | A61B 17/1322 |
| | | | | 602/53 |
| 2015/0133991 A1 * | 5/2015 | Kosiorek | | A61B 17/135 |
| | | | | 606/202 |
| 2015/0150560 A1 * | 6/2015 | Sato | | A61H 9/0092 |
| | | | | 606/202 |
| 2015/0327870 A1 * | 11/2015 | Fortson | | A61B 17/0057 |
| | | | | 606/202 |
| 2016/0213373 A1 * | 7/2016 | Drasler | | A61B 17/1325 |

\* cited by examiner

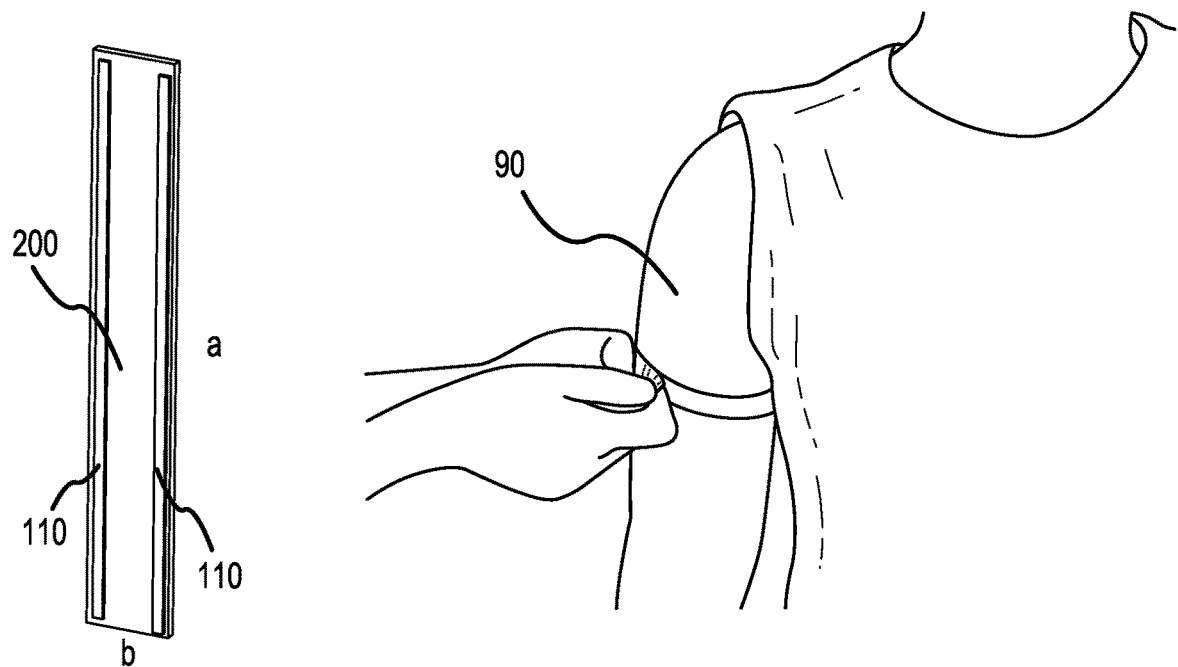
FIG.2A
FIG.2B
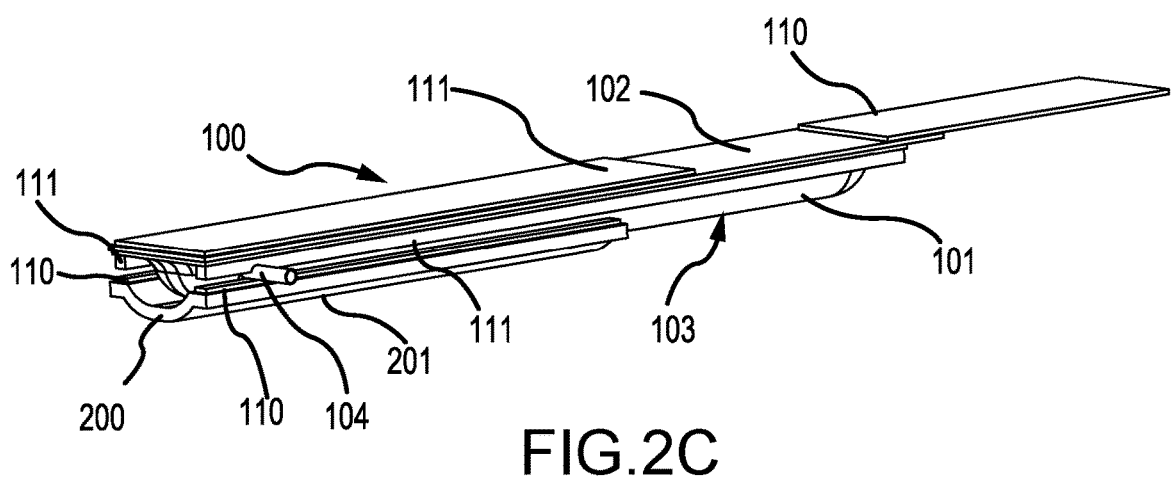
FIG.2C

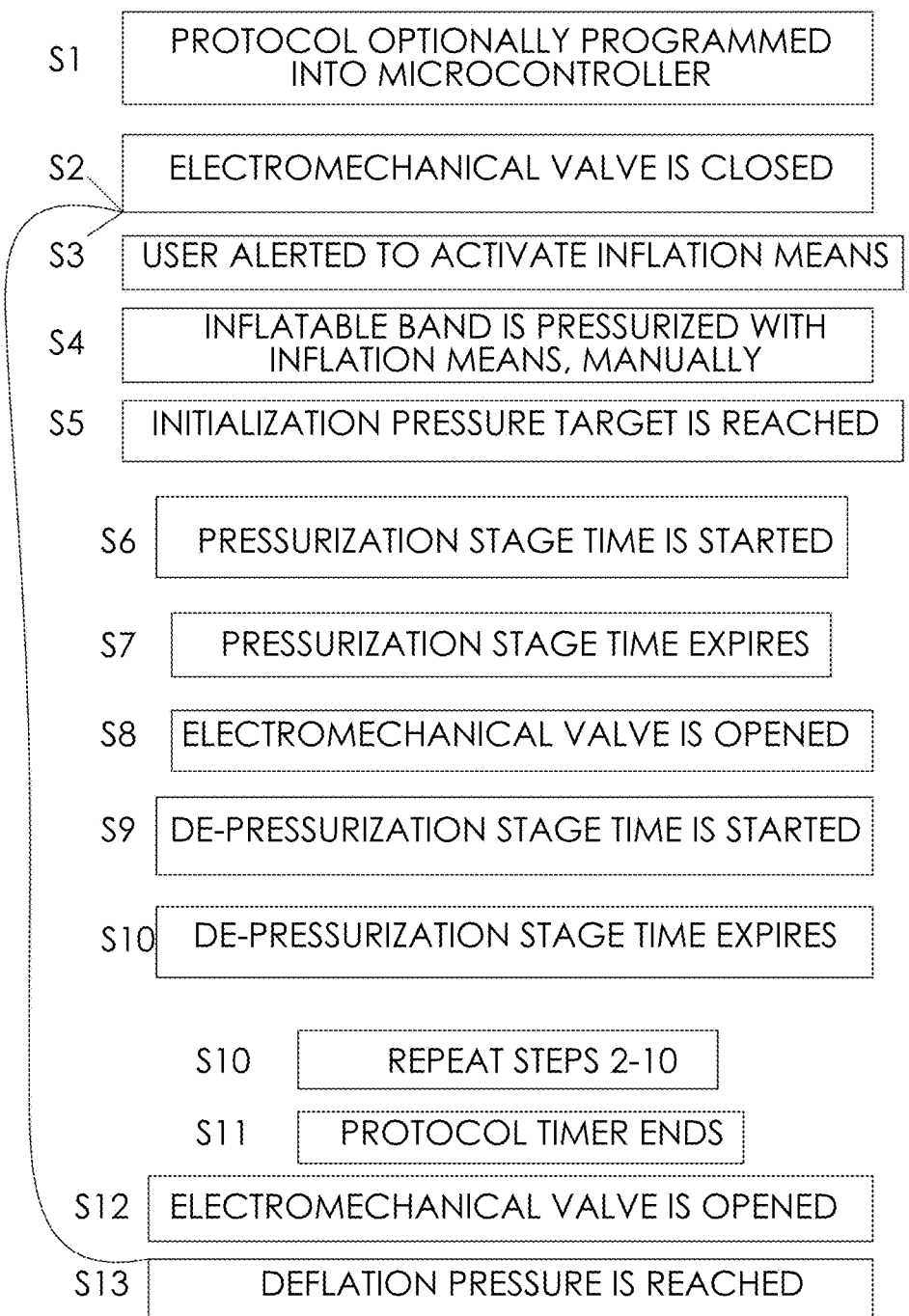

BLOOD FLOW RESTRICTION BELTS AND SYSTEM

CROSS-REFERENCE TO RELATED APPLICATIONS

This application is a continuation of U.S. Ser. No. 15/430,404 filed on Feb. 10, 2017 and entitled "Blood Flow Restriction Belts and System." U.S. Ser. No. 15/430,404 claims priority to and the benefit of U.S. Provisional Application No. 62/293,536 filed on Feb. 10, 2016 and entitled "Blood Flow Restriction Belts and System," and U.S. Provisional Application No. 62/311,936 filed on Mar. 23, 2016 and entitled "Barrel Inflatable Belt." Each of the foregoing applications are hereby incorporated by reference.

FIELD OF THE INVENTION

This invention relates to blood flow restriction systems, and more specifically to an inflatable belt design for use therein, to provide a simple to manufacture, simple to use, comfortable, effective, and less expensive alternative to current designs and products in use.

BACKGROUND OF THE INVENTION

The muscle training apparatus, system, and method described in these applications is spreading fast globally because of its beneficial effects as described below. In addition, national and foreign physicians as well as universities have made research and investigations about it and, as a result of them, researchers have published many articles.

BRIEF DESCRIPTION OF THE DRAWINGS

FIG. 1A-2—shows the inflatable belt of FIG. 1A-1 but in an applied state.

FIG. 1D-1—shows the inflatable belt of FIG. 1C with an inflation means hooked up to the belt valve, and the inflatable means further comprising an adjustable pressure limiting valve.

FIG. 1D-2—shows the inflatable belt of FIG. 1C, with the belt valve coupled with an adjustable pressure limiting valve, to hold, but allow the release of a gas, and the adjustable pressure limiting valve further connected to an inflation means via a tube to transport a gas.

FIG. 2A—shows an example of a body interfacing component with optional means to attach to one or more components of an inflatable belt, and an optional method for determining an appropriate length of the body interfacing component based on the arm circumference, or a fraction thereof, to dictate a preset tension when applied to the arm by simply butting up the two ends of the body interfacing component as the initial tension guide.

FIG. 2B—shows the body interfacing component for FIG. 2A, having been cut down by an appropriate length by x, for an individual user.

FIG. 2C—shows the body interfacing component of FIG. 2B, further in communication with the inflatable belt of FIG. 1A-1 prior to application on the user's limb.

FIG. 9D—shows an example of a flow chart of cycle function, that can be effectively achieved with the blood flow restriction system of FIGS. 9A, B, such that the cycle parameters may be pre-programmed without heavy, expensive, power intensive, noisy, electro mechanical pump is required, and the user is forced to do a beneficial warmup style exercise to prolong the protocol.

DETAILED DESCRIPTION

Figures 1, 1A:
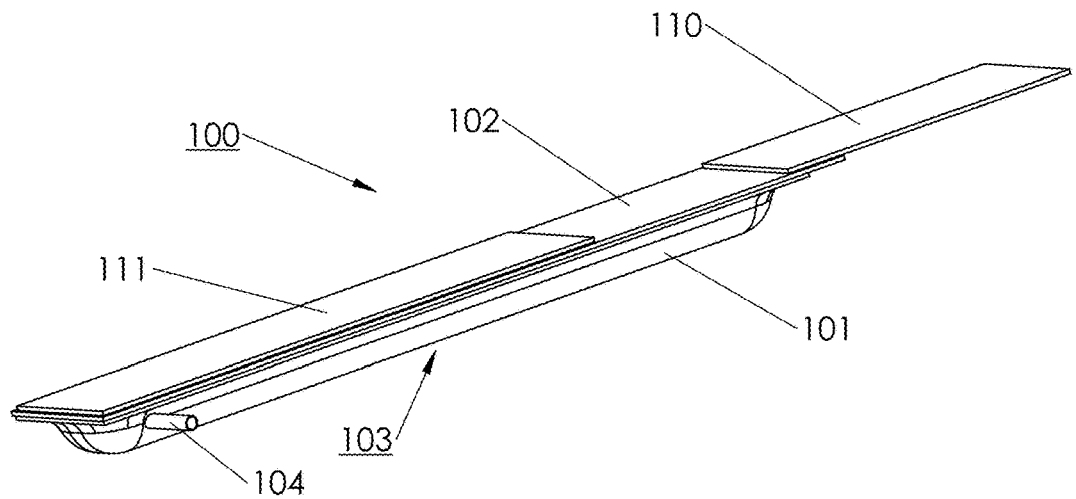
FIG. 1A-1—shows a straight overlap type of an inflatable belt design comprising an outer belt material, an elastic inner belt material, connected to form a gas bladder, and a belt fastening means, as depicted with hook and loop fasteners, to fix the circumference of the inflatable belt when applied to a limb in a straight overlap fashion, and input port for accepting a gas into the gas bladder, for use in a BFR system.

The muscle strength increasing method according to these patents is a distinctive non-conventional one that involves compression of an arm or leg at a position near the top thereof. This muscle strength increasing method (the subject muscle strength increasing method is herein referred to as a "Blood flow restriction muscle training method" or simply BFR.

Blood Flow Restriction Training (BFR) is spreading globally. However, there are various aspects of current technology and expertise that are limiting the distribution of the technology. The BFR training system, and method described in these applications is a distinctive non-conventional one that involves compression of an arm and/or leg at a position near the top thereof.

A relatively narrow (4-10 centimeter), pneumatic belt of unique design, is applied at a proximal location on an extremity, proximal to the main belly of the m. bicep brachia on the arm, and as high on the thigh, as possible, on the leg. The desired effect is to produce an obstruction or impediment to deep venous flow coming out of the limb. To the extent possible, veins and capillaries in the distal muscle are distended and full of blood. The muscle belly and its blood vessels are not covered by the belt, allowing some blood to perfuse those fibers.

Once in place, the belt is inflated to a certain pressure to alter the circulation in the vasculature of the extremity, and this particular pressure level is critical for the effectiveness of this BFR technique.

Effects on the Vasculature.
  a. Superficial Veins—are completely blocked by the inflated belt, resulting in distended surface veins and redirecting blood into the deep venous system.
  b. Deep Veins—Change the pattern of the deep venous outflow from a rhythmic, gentle steady stream of blood, flowing back to the central circulation, to a more pulsatile flow ranging from no flow (0 mls/sec) at times, to very brisk flows (>100 mls/sec) with distal muscular contractions. The deep venous system distends to accommodate the flow into the extremity that is temporarily prevented or impeded from leaving the extremity and then collapses as blood is emptied by muscle contraction and pushed past the deep venous obstruction.

c. The Capillary network is distended and has increased permeability.
d. Arteries—may have inflow reduced, but remain patent.
e. Arterioles—which are the main control of vascular resistance, distal to the band are fully dilated.

At high belt pressures, deep veins are temporarily obstructed until muscle contraction moves blood in the deep veins out of the extremity. When that happens, blood from the arterial side fills back into the extremity. Under these circumstances arterial inflow waxes and wanes depending on the frequency of muscle contraction emptying the deep veins, making more room for fresh, oxygenated, arterial blood. At lower pressures, arterial inflow is not reduced at all, but at higher and higher pressures, due to the inability to overcome the deep venous obstruction and the pressure itself, arterial inflow is reduced, but not eliminated.

Changes in the Circulation have the following effects:
1. By Impeding and modulating blood flow in a certain manner causes;
    i. Angiogenesis—Due to the effects on the vasculature, NO release, the distension of the capillaries and veins and periodic flushing and emptying of the deep veins, all work to stimulate release of an angiogenic cascade documented by increases in circulating VEGF, and m RNA for various angiogenic factors.
    ii. This reduced and modulated blood flow is inadequate to recover the active muscle from otherwise easy, sustainable efforts. A Disturbance of Homeostasis in Active Muscle (primarily, consisting of a decrease pH, decrease pO2, increased lactate concentrations and deplete intracellular phosphates ATP/CP, increase concentrations of Pi, ADP and AMP, altered electrolyte concentrations) ensues as the initial fibers recruited are unable to maintain their work rate.
    iii. This Disturbance of Homeostasis causes initially recruited fibers (primarily fatigue resistant, type I fibers) to fail to produce the necessary force, so that additional larger motor units (with more easily fatigable Type II fibers) are recruited to perform the work. In turn, these Type II fibers become quickly fatigued as their pH and pO2 decrease and their intracellular phosphate stores are depleted and are unable to be replenished.
2. Metabolites from the Disturbance of Homeostasis, accompanied by an anabolic hormonal milieu, stimulate an increase in local protein synthesis in all motor units that were recruited and contracted, via the mTOR pathway.
3. The Disturbance of Homeostasis is also communicated via unmyelinated Group III and IV afferent fibers connected to metaboreceptors and nociceptors, to the CNS and is perceived as "burning", "fatigue", or "discomfort" in the active muscle. The CNS also, increases sympathetic tone and releases an anabolic hormone cascade as noted by a robust increase in circulating growth hormone (GH). The increase in sympathetic tone, increases ventilation and heart rate. The GH release initiates an anabolic cascade, resulting in IGF-1. The anabolic hormone cascade also binds to anabolic cell surface receptors that have been up-regulated in active tissues, facilitating the local stimulation of increasing protein synthesis.

Exercise choice and protocol. There is good reason for the specific protocol of exercises to make the BFR session efficacious. We choose a series of exercises that utilize all muscle groups distal the belt, as well as, muscle groups proximal to the belt. We have a sequence of 3 sets of 30 repetitions separated by 30 second "rest" periods for each exercise. Typically, the person can perform the first 30 repetitions with minimal feelings of fatigue or only during the last few repetitions. Then there is a 30 second "rest" period where, if properly adjusted, the circulation slows down even more since venous blood does not have the force of muscle contraction to pump blood back into the central circulation and blood flow slows considerably and may stop. This further reduces the ability of the muscle to recover and normalize pO2 and pH. The intracellular muscle fiber milieu deteriorates as homeostatic conditions are lost. Then the second set of exercise commences. On one hand the circulation is improved, but the exercise is now being carried out by fibers with little O2, a low pH and a disturbed milieu. Contraction in those initial fibers fails, now other motor units must be recruited to produce the necessary force. Their milieu is disturbed even sooner and this disturbance of homeostasis is being communicated to the CNS. Another 30 second "rest" period ensues where the circulation is further reduced and cellular milieu of active motor units, further deteriorates. Now a third set of repetitions is performed utilizing fibers with very disturbed homeostasis. Failure of contraction happens quickly. Other motor units in the muscle are recruited to produce the necessary force and they begin to fail, partially because the low pO2 and low pH produced by initial motor units diffuses into the later recruited fibers, and partially, because these fibers are rarely recruited and are very glycolytic, rapidly contributing to a milieu inhibiting muscle contraction. Contraction failure of virtually all motor units in the muscle ensues. A robust signal of "failure" is sent to the CNS and the CNS reacts by secretion of an anabolic hormonal cascade.

Taken together, when one performs relatively easy exercise with muscles that have restricted, inadequate blood flow to sustain the work, a disturbance of homeostasis in the muscle ensues, prompting recruitment of additional fibers and ultimately resulting in muscle contraction failure. This "failure of contraction" stimulates local protein synthesis for repair and adaptation, as well as, initiating a systemic response from the CNS to repair and adapt working tissues.

Since the absolute workloads are light, they caused minimal damage to working muscle and much less damage than is normally associated with muscle contraction failure, thus, improvement in function occurs more rapidly than when damage must first be repaired.

While previously filed applications describe the concepts involved in BFR training, they do not address what is physically happening with the human body when the tightening tool is applied. More specifically, they do not address the anatomy of the human, the goal of the tightening tool, and what happens to the body when the tightening tool is applied, and the ramifications this has on the effect of the tool and comfort for the user. In regards to the tightening tool, they neglect to discuss the contributing factors to overall limb compression which is a combination of the shape and geometry of the tightening tool where it contacts the skin, as well as the tension applied via tightening, air pressure, or a combination of the two. For example, Sato discusses the desire to have normal arterial flow for safety reasons, but neglects to discuss that what is actually happening for the mechanism to work, and how the venous system is actually restricted in implementation. Arteries run deep in the body, but veins are both superficial, on the limb surface, and deep in the deep venous system. As the applicant will describe, this has ramifications as to the effectiveness of various belt, or tightening tool, designs and the impact therein on level of comfort and effectiveness. Specifically, the applicant will disclose designs that may target a portion of the circumference of a predetermined target range for compression, without compressing the entire circumference. By compressing only a portion of the circumference, the overall discomfort and feeling of constriction is reduced, yet sufficient venous restriction is obtained, as but one example.

What happens when the tightening tool, or hereinafter referred to as "belt", "band", "inflatable belt", "inflatable belt" etc., is placed on the body, is a certain amount of tissue is compressed inward. Superficial veins are closed off, depending on the level of compression, and tissue is pushed radially inward. This compression level that is felt by the user is a combination of the amount of surface area the belt contacts the limb, and the pressure in the belt in case of a pneumatic belt, or the belt tension in the case of a non-pneumatic belt, and the construction of the belt itself and shape the bladder forms under pressure. Because tissue is incompressible, there is no place for it to go (minimal amounts of tissue squishes out to the sides) and thus, the only "give" in the system is that some fluid displaces to the sides of the bands, and the veins, and eventually the arteries collapse and either partially or fully close off. This explanation is neglected in previous patent applications, leading one to surmise that the inventors did not fully understand what was happening inside the targeted limb with the tissue displacement and fluid shifts. As will be disclosed, what is essential in the end then, is only to cause enough displacement in the correct areas on the human body, i.e, where veins are present superficially or in the deep system, as to achieve the required level of BFR, and to do so in a way that spreads the loading and keeps changes in overall perceived and actual compression levels to a minimum. As an example, the human anatomy is such that the deep veins in the arms and legs may be compressed by applying pressure, to displace tissue inwards on the underside of the arm, and the inside, or groin area of the leg. While all previously disclosed bands have been of rectangular shape and fully encompassing the limbs, these rub over various muscle groups (biceps, hip flexor, etc) causing discomfort, cramping, and pain, when in reality these areas do not have any veins under them and do not require heavy compression. Therefore bladder size, and shape overall of the band, can be optimized to reduce compression in certain places that undergo rubbing over a muscle during movement, the band thinned out over these areas, as will be disclosed below. Understanding the full physiology and anatomy therefore is critical to designing a system that is comfortable, easy to use, and most economical to produce.

Sato also fails to adequately provide a means for applying a consistent starting belt tension by a novice, which further limits mass adoption. The starting belt tension is a critical aspect to the function and overall compression level that is set and an inability to properly, simply, and repeatedly measure this limits widespread adoption, or can be unsafe. Sato routinely discusses the technique needing to be applied by an expert, however this introduces a large barrier to adoption as Sato himself admits. The company, KAATSU, provides guidelines for setting a base belt tension via measuring a pressure once the belt is placed on the arms, but this process is cumbersome in that it requires the user to put on the belt, measure a pressure, then take off the belt to adjust, re-measure, etc. The applicant's locking system and pressure measuring sequence options have solved these issues in a way that is prescriptive based on a user's limb girth.

Various patent applications by two inventors, Sato and Wasowski, have been issued on the devices, apparatus, and methods used to implement BFR training, and various other methods have been published in research papers as discussed. It will be shown how there are yet many improvements to be made both on the apparatus, system and method of application to promote widespread adoption, in the areas of cost effectiveness; comfort, and ease of use, Both inventors describe in their applications the importance of reduce the cost of the system (Sato U.S. Pat. No. 8,992,397), improving the comfort level (Wosowski U.S. Pat. No. 8,273, 114), and make the system easy and safe to use, together with an instructor or by oneself (Sato U.S. Pat. No. 8,992, 397), as the principle barriers to mass adoption, and it is the aim of the applicant to solve these deficiencies in existing product and disclosed embodiments.

U.S. Pat. No. 8,273,114. U.S. Pat. No. 8,273,114 to Wosowski describes a full body suit with the addition of cooling, electrical grounding, and a variety of other features. Wosowski's invention appears to be a variation of Sato's designs, but is significantly more costly and difficult to use. Further Wosowski does not go into any further detail on the blood flow restriction means other than to say they are like ordinary blood pressure cuffs. Ordinary blood pressure cuffs are inelastic and cover a substantial length of the limb, encompassing the bulk of the muscle that is to be expanded during contraction and exercise. In practice, a very wide inelastic cuff around the full circumference, as described by Wosowski, is extremely uncomfortable and even painful because the muscle has no room to expand when contracted. Wosowski therefore fails to contemplate a simple, cheap, affordable, safe, easy to use design for bands or belts for performing BFR training as will be described by the applicant.

U.S. Pat. No. 36,149,618. U.S. Pat. No. 6,149,618 to Sato is the original application on the subject of BFR and describes a simple, non-inflatable belt concept and generic method of using the band to perform the BFR method, or KAATSU Training 1M method. Sato describes a simple band, or rope, made of elastic material, for wrapping around the body as a tightening tool, as well as a band or belt made of inelastic material with spring inserted and indication means to telling what tension is applied. Sato neglects to realize that in the case of such a belt, the belt tension will not be even around the surface of the limb due to varying friction around the circumference, so measuring a tension in such a way is inadequate. Sato appears to have not yet conceived of the method of using air pressure when coming up with this concept and thus there are no features in the design related to making an air-bladder based system function comfortably, effectively, and cheap to make. Sato correctly notes the importance of the tightening tool to have some elastic element and some method of knowing what the compression force is that is applied to the body. While Sato discloses a liner for the belt, Sato only recognizes the importance to protect the user's skin from abrasion. However, Sato's belt will thin in width as it is pulled and may cut into the skin, and Sato fails to note the need for a load spreading mechanism, which greatly improves the comfort of a pneumatic system and simultaneously avoids pinching of the skin. Sato, in U.S. Pat. No. 8,992,397, notes the economical nature of this construction, and the importance thereof, however Sato's following patents are all utilizing a pneumatic adjustment, as is the KAATSU equipment currently on the market, and thus Sato has acknowledged the superiority of a pneumatic system for adjustability, precision, safety, and efficacy standpoint. This is likely because such a construction as described in U.S. Pat. No. 6,149,618 would be cumbersome for a user to try to adjust by make small adjustments in the locked circumference, vs, locking a circumference and adding small amounts of air pressure, In trying to achieve a specific tension, the adjustments would be very small and difficult to read or accurately achieve with the type of system and scale Sato presents. Therefore, as an initial tension setting mechanism, this concept is not very practical. Sato, and Wosowski both for that matter, correctly recognize the superiority of a pneumatic system.

U.S. Pat. No. 7,413,527. Sato then advanced to U.S. Pat. No. 7,413,527, in which he improved upon the simplistic band design with an inflatable belt design. Sato also mentions another deficiency of U.S. Pat. No. 6,149,618, which is that Sato's design in U.S. Pat. No. 6,149,618 rotates around the limb when a user attempts to tighten it by themselves, which would further make setting an initial tension very difficult. This is a problem with U.S. Pat. No. 6,149,618 because for that device to function, significant compression must be applied by the band itself, initially, to achieve the required levels of compression, further exacerbating the problem of setting the initial tension accurately and repeatedly. This rotation therefore renders the design very difficult to use by an individual, further limiting adoption as stated by Sato in later applications. However, Sato's solution in U.S. Pat. No. 7,413,527 is to add multiple additional belt members which further complicates the sewing process, adds materials, bulk, and cost to the system. The applicant will disclose how adding frictional features to the band helps to adhere to the user's limb, and in addition to removing the need to apply high initial tension, will ameliorate the problem of rotation of the band style in 61/149,618. Sato aimed to resolve the problem of lack of precision and easy adjustment by creating a tube that slips inside a hollow bag, the bag formed by sewing two pieces of fabric together, both of which are elastic. Sato further describes the tube being replaceable and a clip being used to fold over and limit the length of the inflatable tube. However, such suggested construction of stuffing a tube into a hollow bag for each application or each individual user is impractical and a barrier to ease of use, where Sato has described himself that ease of use of the band is a critical factor toward the utility of BFR. Sato further discusses about the need for the clip such as to eliminate a gap between the muscles at the overlap point and provide full circumference compression. This further shows that Sato does not fully understand what is happening inside the limb and where it is important to apply pressure, and why this clip and limiting features is not necessary. Sato further discusses a deficiency in the design such that a limiting piece, such as a plate, or wire, is necessary to prevent expansion of the tube in the radially outward direction, similar to what happens when inflating an inner tube. Sato specifically states that the main belt has a predetermined elasticity, as do current KAATSU products. This benefits in expanding slightly during muscle contraction, but forces inclusion of the limiter plate to prevent radially outward expansion, and thus adds parts, complexity, and cost into the design. Sato describes modifying the construction of the tube itself so that it may inflate more toward the inside than the outside, however Sato is still stuck on the idea that there is a main band around the tube, and that all components, and the tube as specifically stated, are elastic, further necessitating a limiter plate. Sato describes two strip shaped elastic bodies having different spring rates, but by virtue of them both being elastic, there will be radially outward expansion and thus, a requirement for additional hardware to maintain required compression. In fact, Sato never addresses the need to determine initial compression of the inflatable system, and further does not discuss the by-product of higher initial compressions as a detriment to the comfort; and decreased safety, of Sato's designs. High initial compression results in discomfort because there is always some degree of restriction and when there are metabolites and lactic acid built up, there is not enough flow to relieve that pain, even at rest, so there is a constant discomfort not easily tolerated by many people. In failing to address the initial compression guidelines, or design elements, Sato has optimized the inflation scheme as it relates to comfort of the user. As described above, a tight band is uncomfortable, and without a large air cushion, the muscle is further in contact with the harder, stiffer main band Sato describes when the muscle contracts. This puts higher stress on the muscle and can lead to pain, cramping and discontinuing use. The applicant has witnessed such effects first hand with current KAATSU equipment where the hip flexor muscle feels it was hit with a hard object from this compression point loading, and rubbing, Similar effects of nerve impingement on the arm were felt and pain lasted for several days. It is an aim of the applicant to solve this problem by spacing the inflatable bladder off the limb by a sufficient amount that it may inflate inward to form a large air cushion, further assisted by a body interfacing component that spreads the load on the limb.

Overall, Sato fails to recognize that the construction of his band has unnecessary components in it, and that sufficient, radially inward, more comfortable, and easier to apply, compression, can be achieved with proper construction techniques and selection of materials as will be disclosed by the present inventor. By stating that economics are important, yet including unnecessary components in the main band construction in this application and in now-current product sales, Sato unnecessarily complicates the design, driving up manufacturing costs, and increasing the price to the end customer, and shows that he has not contemplated a simpler more efficient design like that disclosed by the application.

U.S. Pat. No. 7,455,630. Sato then moved to U.S. Pat. No. 7,455,630 wherein he depicts a simplified BFR system consisting of a manual analog valve readout, and manual squeeze ball inflation means. However, rather than expanding on a full system that would be cheap and effective to implement, Sato continues to invent around methods of limiting the inflation toward the user's limb with complicated limiting plate designs. Sato seems to have come to the conclusion that the limiting plate is a key feature, (as it currently exists in the product as well), and is therefore focusing on adding components to the design, rather than rethinking the design to eliminate parts and make the construction more efficient, yet just as effective, as the current inventor has conceived. Sato further discusses the need to provide even compression around the entire limb with a complicated limiter plate design that bends and contours. However the limiter plate is not in contact with the skin, the air bladder is, and the air pressure, and presumably the profile of the bladder in contact with the skin in the bladder is uniform therefore the compression will be about the same. This is yet another confirmation that Sato does not fully understand the physics of what is happening with the band, and what is needed to achieve the proper level of venous restriction. As stated above, but restated here, the applicant's invention of a spacing method to space the air bladder, or gas bladder off the limb, thereby providing a large inflation volume, more uniform contouring of the bladder to the limb, which has the significant effect to improve comfort.

Part of this is evidenced by applying a KAATSU band and band of applicant's invention on the same location and doing a muscle contraction and measuring the pressure. In the KAATSU belt, placed around the quadriceps, the pressure in the belt rose from initially 350 to 420 mmHg. In the applicant's belt design the pressure rose from initially 350 to a maximum of 380 mmHg. This reduction in spikes in pressure, and correspondingly in compression due to substantial maintenance of the band/limb junction profile, during muscle contraction, means that the muscle is seeing less force overall and therefore is not getting cycling "pounding" during movement on each contraction from the applicant's band as it is with the KAATSU band In experiments, the KAATSU belts became too painful during a dynamic training session that the subject had to discontinue the training, whereas the subject could complete a BFR training session with the applicant's band to achieve muscle "failure", vs bruising or cramping sensation. Despite the fact that the limiter plate is not necessary, Sato further does not describe any elastic characteristic of the limiter plate; in fact he contemplates it as inelastic. Thus because the limiter plate is coupled to the main belt, and encompasses the limb, the main belt will be prevented from expanding under muscle contraction, further exacerbating the pressure and pain on the muscle and causing higher pressure spikes in the band under muscle contraction. All in all, U.S. Pat. No. 7,455,639 to Sato has the same deficiencies as U.S. Pat. No. 7,413,527, and further reinforces Sato has not contemplated the simplifying elements of the applicant's invention.

U.S. Pat. Nos. 8,021,283 & 8,328,693. Realizing the difficulty in facilitating widespread adoption based on significant expertise and knowledge of the body, Sato further continued to invent along the lines of automation and sensing to make KAATSU Training safe for any person. U.S. Pat. Nos. 8,021,283 and 8,328,693 to Sato principally focus on these automation aspects, assuming band designs as discussed prior. In fact, Sato even discusses the inadequacy of just measuring pressure because of physiological changes during the workout, for example the increase in limb circumference from doing work during KAATSU Training, and Sato's belt designs inadequacy of dealing with these expansions to keep a more constant compression level on the limb. Sato further reinforces the need for accurate, more constant pressure control, so it is significant that Sato's band designs result in high pressure spikes during muscle contraction compared with the applicant's invention. Sato does not even address the ability of the band design itself to maintain more-constant pressure by providing a larger volume for example, presumably because Sato does not recognize the significance of improving upon such feature, and the ramifications thereof in relation to comfort for the user. Whereas the applicant's invention is optimized to maintain a certain compression level on the limb by achieving a larger air volume and maintaining a specific contact profile with a limb, than Sato's designs for a given desired compression, Sato's bands encompass relative little air as the inflatable portion is rested directly against the skin to begin with, and therefore less volume into which the bands can expand before compressing the limb. Because there is less air, any change in limb circumference will proportionally correlate to a larger % of displaced volume in the gas bag, and a larger deformation of the bag itself which will also alter to overall limb compression level, This large percent displacement was observed as a high pressure spike, and overly large percentage increase in pressure over time during a KAATSU Training session, which further restricts flow, potentially beyond a safe level. The applicant's inventions, which allow for a large air volume, and less deformation of the bladder shape during a muscle contraction, act as an accumulator and increases in limb circumference during training have less of an effect on the increase in band pressure, and overall compression level on the limb, because the displacement represents a smaller proportion compared to the total volume of air in the bands.

Sato, in discussing the safety aspects and need to avoiding a situation where full occlusion of the venous system is achieved, fails to recognize that his system may start a session in a safe zone, but then, as the limb engorges in blood and expands, the level of restriction may become unsafe because the pressure in the bands has risen significantly. Sato describes a disconnect option, as do current KAATSU products, and thus by disconnection from the control equipment, a user is potentially given a false sense of security that they are still safe when disconnected from the monitoring and adjustment equipment. This all goes to point out that the design of the bands is critical, and a design which minimizes pressure increases during a training session, as disclosed by the applicant, is a safer inherent design.

One final note is that while Sato argues for a fully automated system, the applicant argues for a hybrid system with a manual inflation means and automated pressure control. The significance is that if there is a problem, the safety procedure is always to reduce pressure and restore normal conditions, which both Sato and the applicant agree on. However in Sato's automated system, the machine can potentially continue to work and prolong the unsafe condition, whereas a re-inflation action is required to be performed by a human in the applicant's system, and the human can assess many more variables in the situation better than Sato's machine, in deciding whether to continue or not.

Relating to bands, Sato does disclose another configuration of a gas bladder, or bag, plus belt combination by stating the gas bag may be on or in the belt. Prior, the gas bag is only described as being in the belt. However, Sato does not go into detail on how exactly this works, and it is left to believe that the gas bladder is a separate item that is permanently attached to the belt, and thus still incorporating more components, and manufacturing processes than the applicant's inventions. Sato further fails to describe a "doubling back" band, such as disclosed in U.S. Pat. No. 6,149,618, further confirming that Sato has discarded such design as non-preferable and too difficult to use by the user because of the rotational issues, which the applicant has solved. Sato further states the importance of being able to utilize the system for longer periods of time, saying that the technique of restricting blood flow is improved with longer durations. Therefore, this further reinforces the importance of band comfort during training, and the value of the applicant's inventions in improving comfort such that a user may sustain restricted flow for a longer period than with KAATSU equipment, because the comfort level is better. Sato further describes the belt as being elastic, neoprene rubber, which, as Sato has previously stated, requires a limiting plate in order to provide sufficient restriction. Thus, Sato's designs have not significantly changed from prior applications, and still remain expensive to build and cumbersome to use.

The focus of U.S. Pat. No. 8,021,283 is around automation and sensing and creating a system that the user does not have to think much about. Sato's design provides various drawbacks and could be improved as the applicant will disclose. In discussing the pressure setting means, Sato defines the pressure setting means as being able to both provide and remove pressure from the belts. This further differs from the applicant's provision for a manual inflation means, electromechanical valve, and belts as the basic elements in a blood flow restriction system. By removing the need for an electrical pump, which is what Sato describes, the system can be greatly simplified in terms of cost, electricity requirements, weight, noise, and speed of inflation. All these are significant drawbacks in the usability of the system and a barrier to widespread adoption. Sato fails to conceive of a system that optimizes the benefits and tradeoffs of an all electrical system with one that is a hybrid. A manual inflation means is faster to inflate the belts. Current KAATSU products employ small pumps, which take significant time to fill the belts with air, up to 5× slower than the applicant's suggested hand pump based system. Time is critical to the user, and in fact of the two models KAATSU offers, a main sales argument purported by KAATSU is that the larger more expensive system inflates faster and reduces waiting time. Therefore, an inflation means that is faster than what Sato describes is beneficial. While Sato could use larger pumps, this increases cost, weight, bulk, and reduces portability which are all significant drawbacks. KAATSU is further touted as being portable, lightweight, and carry anywhere, thus the ability to eliminate large batteries, and heavy pumps and electronics (as seen on the www.kaatsu-global.com website for the Master and Nano products), is of further benefit.

Continuing, the pumps represent the main reliability failure point, and cost for the system, thus being able to eliminate them by using a manual inflation means, further has benefit in making the blood flow restriction system cheaper, and more reliable. Using pumps also drains the battery, and as KAATSU is in part meant for travel purposes, not having to carry a bulky charging cable, or go search for a power outlet is of further benefit in eliminating the pumps, Finally, KAATSU, as seen on the website, is further touted as applicable for use in the workplace, however pumps are noisy and not suitable for a work environment. While sound proofing could be added, this would further add unnecessary cost and complexity and potentially lead to overheating and further reliability issues. Finally, a manual inflation system as disclosed by the applicant requires the user to use some muscles to pump air into the valves. In particular, in a cycle function as disclosed herein, such movement is repeated and helps serve as a warmup for the BFR training, Sato in later applications discloses the importance of a warmup, but does so purely in the frame of a system exercising the vasculature and not requiring any movement or muscle activation by the user. The applicant's invention for a blood flow restriction system requires the user to perform simple warmup exercises of squeezing an elastic squeeze ball to pump up the bands, thereby getting some blood flowing. The applicant has further shown that muscle contractions squeeze blood past an extremity and prevent a state of completely occluded blood flow for a long period of time which could be dangerous.

In fact, KAATSU Training teaches an exercise that is very similar in doing hand grip motions, but only teaches doing this exercise AFTER the bands have been pressurized, not prior to or during the pressurization process. Doing such exercises to pump up the bands saves time in the long run as one set of recommended exercises is done simultaneously with the inflation or warmup cycling in the applicant's disclosed systems and methods, versus done serially according to KAATSU Training protocols. For all these reasons, a hybrid system, as disclosed in the applicant's inventions, which utilizes manual inflation means with electromechanical pressure control means is a more effective and safer solution overall. Finally, Sato discusses use and placement of a number of sensors to improve the safety of KAATSU Training, and deficiencies related to these sensors may be discussed in further applications by the present inventors.

U.S. Pat. No. 8,992,397. In U.S. Pat. No. 8,992,397 to Sato, Sato comes back to the band design as a critical element to improve and reiterates, and further reveals, significant shortcomings of his previous inventions. Sato recognizes the superiority of a pneumatic system in improving the safety and pressure adjustment capabilities during setup and in the middle of a training session, but acknowledges the complexity in the design as a detriment to a pneumatic system versus a simple elastic band. Sato fails to recognize a design that is both simple and inexpensive to construct, and incorporates, and improves, the benefits of using pneumatics to apply pressure to the user. Sato describes two band structures, a straight type, and an overlap type, and how they have a significant drawback of rotating on the user's arm when trying to apply initial tension. Because of Sato's band design, and the lack of a means to stand the band off the skin surface, the initial tension of a substantial degree is required to provide enough starting compression to obtain a sufficient overall compression level on the limb. In addition to solving the rotational problem, the applicant's invention does not require strong initial tension to achieve the required limb compression and therefore eliminates the rotational issues, while maintaining a simple construction. Sato further describes an overlap type of having a detriment that the ring employed, may cover a muscle region during rotation and cause discomfort the user, thereby further acknowledging the critical nature of user comfort in the application. Because the applicants design does not require significant initial tension the displacement of the ring is not a problem. Further, the band may additionally be adjusted circumferentially after the fact as needed. Further still, Sato describes the gas bag as being divided into two chambers by the ring and the pressures in the band not be controllable, however Sato therein, assumes that the circumference of the inflatable bladder must be longer than the limb circumference, causing the bladder to move through and wrap around the ring. In the applications designs, and as described prior relating to understanding the physics of what is happening in the limb, the bladder does not need to be the full length of the limb. Additionally, failing to state that the bladders may be detachable, shows that Sato considers the gas bag/bladder to be permanently fixed to the band, which is further counter to another embodiment of the applicant's invention for a detachable gas bladder which and be changed out for various length bladders sizes for each limb.

Sato continues to state and discuss the concept of a belt plus a bag, therefore continuing to reinforce he has not contemplated a similar construction like the applicant is disclosing. Likewise, Sato continues to describe the nature of the compression force applied as necessarily 100% around the circumference, and evenly distributed, which again continues to reinforce that he does not truly understand the physics of what is happening, or contemplate other methods of targeting compression zones. Finally, Sato explicitly states the potential problem of excessive compression on the muscle during contraction and how this can lead to safety concerns, and therein cements the idea that pressure spikes and large changes in overall compression are to be avoided. Sato's suggestion for how to remedy this is to make the belt material (in addition to the gas bag) elastic, however, as Sato has previously disclosed in prior patents, this necessitates a limiter plater and increases the cost and complexity. Sato's principle invention therefore is the addition of a second strap on the band to be grabbed by the user's other hand, to help avoid rotation and properly position the band. However, this is just adding yet more components to the solution instead of solving the underlying problems, in this case rotation and the need to apply significant initial tension. As a note, Sato does describe a thin inner fabric, but discusses this only in the context of creating a soft surface interface between the user and the belt, not as a standoff mechanism. KAATSU's recommended guidelines actually suggest applying the bands over clothing (presumably to prevent pinching of the skin, and thus this design element is really not necessary. More importantly, it is clear that this inner fabric is not intended to be a spacer or load distribution mechanism as is described by the applicant.

U.S. Pat. No. 8,182,403 & US2015/0150560A1. Sato continues to improve and perfect his KAATSU Training method in U.S. Pat. No. 8,182,403 to Sato and pending application US2015/0150560A1, however these applications offer nothing new in terms of band design, and continue to use the same language and concepts around a bag plus a belt, elasticity which requires limiting members, and precision of pressure control, which is inherently better in the applicant's invention. The patent mainly describes other methods of implementation and using automated cycling of the pressure as a warmup for the user to reduce the chance of occlusion when higher pressures are used. Sato explains that without cycling, a certain lower pressure will lead to occlusion than with cycling, and that a higher pressure is more optimal in terms of effect of the technique. In relation to the blood flow restriction system itself, the system of Sato is substantially the same as previously described in U.S. Pat. Nos. 8,021,283 & 8,328,693, and therefore the shortcomings of a full automated system, when compared with a manual inflation plus electromechanical pressure control system, are likewise similar to previously laid out. However, Sato offers yet another important comment that further supports the fact that, while he has invented a useful technique with supporting hardware, he still fails to understand the interplay of the human physiology and how it relates to the design of the belts themselves. Sato describes in detail how cycling of the pressures between a minimum and maximum value, and doing so prior to training serves as a valuable warmup and preventive measure against over compression and venous occlusion. Sato further lays out specific pressure ranges and discusses minimum step increments of 30 mm Hg. However, not once does Sato mention the importance of band design, and in particular the width, and its effect on the various pressure levels. In fact, a wider cuff, when inflated to a given pressure, will displace a larger amount of tissue on the limb than a narrow band, and therefore lead to occlusion at lower pressures, even lower than what Sato has recommended. Similarly, minimum steps would need to be adjusted downwards for wider belts. Because Sato does not discuss this aspect at all, one is led to believe that he doesn't understand the ramifications of the specific band design, and in particular the width, as it relates to what is going on in the limb. This further evidenced by Sato's discussion of the upper range or pressures to which to cycle being equal to systolic pressure for the arms, and systolic +20 mm Hg for the legs, however Sato fails to give any guidance as to how these numbers should be varied based on the band design or user body type. It is therefore beneficial, as the applicant will show, to have a band design that inherently makes it difficult to reach occlusion pressures during BFR training, and reduces the need for a cycling, or warmup phase, as a countermeasure to occlusion at sub-optimal pressures. Further still, the applicant's manual inflation means not only reduces the cost and complexity, but forces the user to do muscle contractions that squeeze some blood past the obstruction, and itself serves as a warmup as previous stated, rendering an automated cycling process less efficient. Finally, Sato continues to reinforce the key aspects of the band design, that the band outer piece should be elastic, necessitating a limiter plate, and that the pneumatic bag be a separate piece attached to the band and approximately equal to the circumference of the limb.

In relation to the issue of comfort, which Sato and Wosowski both deem of critical importance, Sato also fails to recognize that the band design he sets forth will result in kinking, and that these kinks will reduce the uniform compression Sato says is important, but even more importantly, that these kinks will pinch the user's skin. This issue is discussed in prior art in relation to occlusive cuffs, and the applicant has witnessed such effects first hand. As the pressures are increased this pinch can be quite painful on sensitive surfaces like the inner arm or inner thigh. The application will provide several ways to overcome this issue in the course of this specification.

It is worth pointing out again that the design of the belt and understanding the physics of what is happening is critical to providing an effective, yet comfortable BFR experience. By reducing pressure spikes and maintaining conformance between the bladder and the limb, it is also safer, as Sato describes. Sato's efforts to combat this problem were purported to be solved by adding active control means to the system but this has multiple downsides. To start, pressure is not the ultimate measure of compression on the limb, it is only a contributing factor. For example, if a bladder was very loosely placed around a limb, it could be inflated to 500 mmhg and potentially barely compress the limb. This starting tension is a critical measure. Similarly, if the bladder has very small diameter, it will reach maximum expansion quickly as it forms an annulus, and further pressure will increase the tension in the walls but not put much additional compression on the limb. Additionally, active control means tethering the user to the pressure control system, and thus preventing them from doing dynamic movements, which is an important aspect taught in KAATSU Training. Secondly, the muscle contractions would squeeze out a significant amount of air during a single contraction, and the pumps employed in KAATSU equipment are not strong enough to re-inflate the bands in time to prepare for the next contraction. Significantly larger pumps would be required, thereby exacerbating the stated arguments of why electromechanical pumps are bad. The applicant's inflatable belt designs have been shown to keep the pressure in the inflatable belts at a more constant level than Sato's designs, and in addition, by forming a larger volume, keep a more constant profile against the limb, and thus all such problems related to pressure regulation have been substantially reduced by the applicant's inventions.

Accordingly, besides the objects and advantages of an inflatable belt for use in a blood flow restriction system described in this specification, several objects and advantages of the present invention are:
  a) to provide an inflatable belt that is simple and cheap to build
  b) to provide an inflatable belt that is designed to improve the comfort for the user
  c) to provide an inflatable belt that distributes the compression load onto the user's body in a more even manner to improve the comfort for the user
  d) to provide an inflatable belt that minimizes pressure spikes in the belt during a muscle contraction e) to provide an inflatable belt that is easy for a single person to don and remove
f) to provide an inflatable belt that is compact and easy to transport
g) to provide an inflatable belt that works for a range of user body types
h) to provide indicating means in the inflatable belt construction for making donning the belt simple and without requiring thinking or fine adjustments by the user
i) to provide a countermeasure to rotation when putting an inflatable belt on one's own body
j) to provide a means of limiting pressures in an inflatable belt to ensure that uneducated user's cannot use the inflatable belt unsafely
k) to provide a pre-inflated belt that does not require connection or inclusion of an inflation means, yet provides the benefit of the inflatable concepts
l) to provide a countermeasure to kinking of the inflatable belt and pinching of the user's skin
m) To optimize the target compression range on a limb for a targeting inflatable belt for performing BFR, wherein the compression region is only so large as to sufficiently compress necessary blood vessels, but does not encompass the entire limb, or overlap key problematic muscles such as the hip flexor or tricep
n) To provide a modular, replaceable, individually customizable bladder design that can be attached and removed from the inflatable belt assembly.
o) To provide a fully molded inflatable belt that incorporates sufficient features and dimensions to hold its location on the user's body, yet provide sufficient compression to accomplish the desired BFR effect.
p) To provide a preset relief and manual relief mechanism in combination into a single component for use in a BFR band in order to reduce part count and manufacturing costs, and the preset relief may or may not be adjustable
q) To provide an electromechanical blood flow restriction system that comprises a manual inflation means instead of an electromechanical inflation means in order to reduce the bulk, cost, battery requirements, charging lifetime, charging time, reliability risk, and risk that the system continues if the user experiences a problem, and for the electromechanical blood flow restriction system to allow for substantially all the same functionalities and benefits as a fully automated system.
r) To provide a prescription system for simply applying the proper belt tension to one's body without prior experience.

Still further objects and advantages will become apparent from a consideration of the ensuing description and drawings.

DRAWINGS - REFERENCE NUMERALS

Figures 1, 1A, 2:
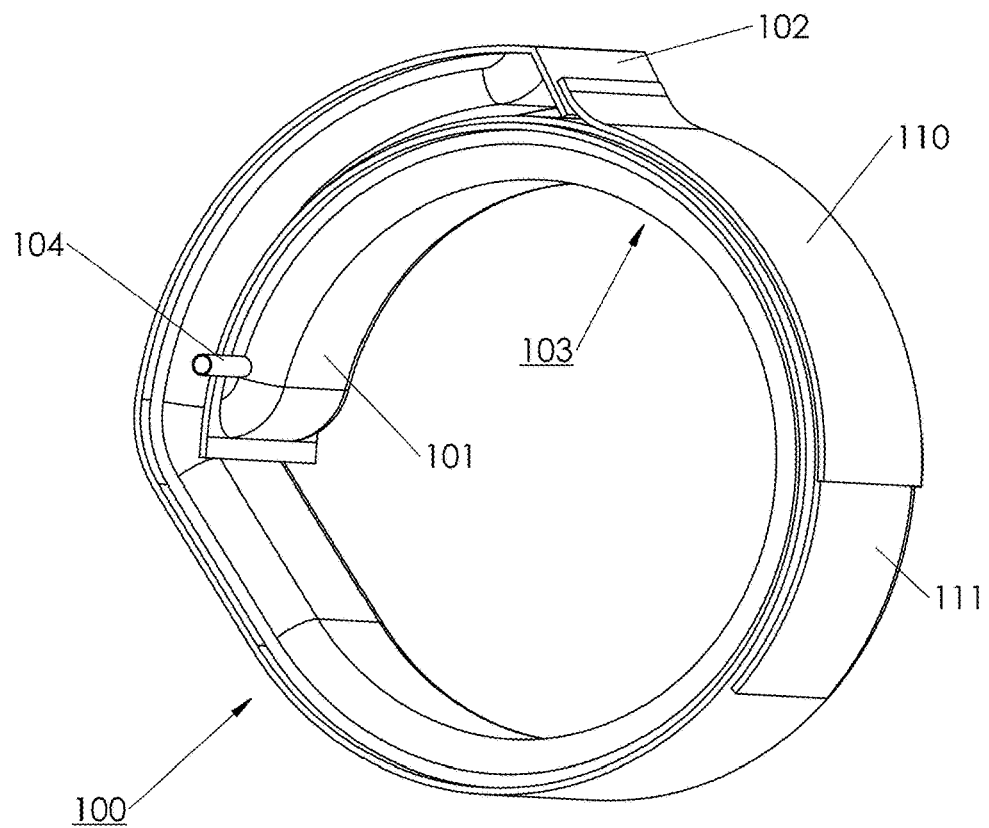

90 - User
100 - inflatable belt
101 - inner belt material
102 - outer belt material
103 - gas bladder (assembly)
104 - input port
105 - belt fastening means
106 - inflation means
107 - belt valve
108 - gas flow shutoff means
109 - airflow DRAWINGS - REFERENCE NUMERALS -continued 110 - first fastening means
111 - second fastening means
112 - ratchet style mechanismnism
113 - cam-lock style mechanismnism
114 - belt spring
115 - loop coupler
116 - blood flow restriction system
117 - pressure limiting valve
118 - adjustable release valve
119 - gas hose
120 - valve coupling
121 - belt tension strap
122 - teeth
130 - handle
131 - edging
139 - overlap length
200 - body interfacing component
201 - friction surface
300 - targeting inflatable belt
301 - target compression zone
302 - compression relief zone
400 - modular inflatable belt
401 - detachable gas bladder
402 - inner belt surface
402 - bladder limiting clip
501 - inner molded bladder
502 - outer bladder surface
503 - anit-roll feature
700 - pre-inflated belt
701 - inflatable chamber
702 - tensioning means
703 - pressure readout
800 - pressure relief valve combo
801 - manual relief mechanism
802 - pressure relief mechanism
803 - spring
804 - manual relief plunger
805 - pressure relief plunger
806 - adjustment cap
807 - pressure relieve valve body
808 - hose barb
809 - one-way valve
810 - o-ring
900 - Electromechanical blood flow restriction system
901 - electromechanical valve
902 - pressure sensing means
903 - microprocessor
1400 - adjustable distance measuring and positive locking system
1401 - non-inflated belt
1402 - distance indicator
1403 - positive lock adjustment
1404 - positive locking means Preferred Embodiment—Description. A preferred embodiment of an inflatable belt 100 for use in a BFR system is shown in FIG. 1K. The inflatable belt 100 is comprised of an outer belt material 102 which is substantially inelastic, such as single or double side urethane coated ballistic nylon of 800 denier. Such class of material is commonly referred to in the fabrics world as non-stretch, and where the term inelastic is used in this application, the reader shall understand the applicant's intent is to refer to this non-stretch class of material. The reader shall further understand that non-stretch fabric is understood in the industry to have certain characteristics regarding stretch, such as in the warp and fill directions, and other materials which may not necessarily be considered fabrics, but that have similar non-stretch properties shall also be considered "non-stretch" or "inelastic" within the context of this application. The reader shall understand that material properties of the belt may be changed to alter the elastic compressive response as described in the operation section of the preferred embodiment. For example, a stiffer material may provide a harder, stronger response, and a more elastic material may provide a softer response. This may be advantageous when design the inflatable belt 100 for different types of users. For example those with big strong limbs may desire a stronger, harder response while the elderly or frail may desire a softer response from the belt. The strength/weight of the fabric maybe lighter or heavier, such as 50 denier or 800 denier, and lighter fabric may provide additional advantages in terms of cost, weight, and compliance for conforming to the body. Important aspects of the outer belt material are that: it doesn't stretch or stretches to a very small degree, can hold a gas, or is substantially airtight, can be connected in an airtight fashion to an inner belt material 101, unless formed together with the inner belt material to make an integrally formed component. Ideally the outer belt material 102 is also machine washable. A substantially inelastic outer belt material 102 removes the need for complicated and expensive limiting plates and other such constructions as described by Sato, and forces the inflation to occur inward toward the user as can be seen in FIG. 1L, thereby proving that the complicated structures of Sato's bands are not necessary. The connection between the outer belt material 102 and the inner belt material 101 is preferably heat sealed, or RF welded, however the reader may note that many means for attaching two fabric like materials in an airtight fashion, such as bonding, may be considered within the scope of this invention. The width of the outer belt material 102 may be approximately 1 in-3 in for inflatable belts 100 intended for the arms and approximately 2-4.5 in for inflatable belts intended for the legs. However, the reader may note that, as described in other embodiments the shape may also be non-rectangular and may span a wider or narrower region at different points around the circumference. In general, for areas where freedom of movement is needed a narrower section may be beneficial, and for areas where load needs to be applied, a wider section may be beneficial.

The inner belt material 101 is preferably an elastic, or stretch fabric, material, and may have a significantly higher degree of elasticity than the outer belt material 102. The inner belt material 101 similarly may be connectable to the outer belt material in a substantially airtight fashion, and may itself be made of a substantially airtight material. For example the inner belt material 101 may be polyurethane coated nylon stretch fabric.

When the outer belt material 102 and inner belt material 101 are connected they form a gas bladder 103 as shown in FIG. 1K. The connection profile forming the gas bladder 103, may be along the entire perimeter of the inner belt fabric 101 or outer belt fabric 102 as shown in FIG. 1K, or may be along only a portion thereof. A gas bladder 103 that is formed along a portion of the circumference of the inflatable belt 100 may have the advantage that it only applies compression to a specific region on the limb and thus reduces the overall sense of compression to the user, improving a feeling of comfort as described further in the embodiment of FIG. 3. The gas bladder 103 may also have a non-rectangular profile, discussed further in the embodiment of FIG. 3B. Further still, in the configuration of FIG. 1K, a gas bladder 103 that is smaller than the length of the inflatable belt 100 may not run through a loop coupler 115 and exhibit the potential issues discussed by Sato in U.S. Pat. No. 8,992,397. The inflatable bladder 103 may be located anywhere along the length of the inflatable belt 100 and is not restricted to starting at one end, or at a junction with an optional belt spring 114 as shown in FIG. 1K.

An input port 104 is in communication with the gas bladder 103 to allow a gas to flow into and out of the gas bladder. The input port 104 may be an RF weldable valve component, or simply a tube welded or heat sealed between the inner belt material 101 and outer belt material 102 as in an IV bag. The input port 104 may be attached protruding out one edge of the gas bladder 103 as shown in FIG. 1A-1 for example, or may be connected perpendicular to the outer belt material 101 as shown in FIG. 1K. Perpendicular connection have a benefit of or being easy to connection an inflation means 106 because the user can use their limb as a back stop, versus a connection point that is parallel with the user's limb as would be in FIG. 1A-1. The specific material and method of fastening is not critical as long as an inlet is created in an airtight fashion. One or more valve configurations, such as a belt valve 107 (not shown) may further be placed into the input port 104 as part of the inflatable belt 104, but this is not necessarily part of the assembly. The belt valve may be disconnect-able, or otherwise removable, or may be a permanent fixture on the belt assembly. As discussed in other embodiments, there are many such valve configurations and combinations that produce beneficial results and the inflatable belt 100 of FIG. 1K, may include any one of them or derivations or extensions of them, or none at all.

The belt spring 114 is depicted as elastic stretch webbing and may be coupled to the end of the outer belt material 102, through means known in the art, such as stitching, bonding, RF welding, etc. However the belt spring 114 may also be connected elsewhere along the length of the outer belt material 102, for example at the mid-point of the outer belt material through suitable means. The main requirement of the belt spring 114 is that it resides at a point along the circumference under tension, and is in direct, or indirect communication with the outer belt material 102. If stitching is used, care is taken to not puncture the gas bladder 103 if the gas bladder commences at this end of the outer belt material 102 as shown in FIG. 1K. The belt spring 114 may be any such elastic material, and is itself an optional component. Should the outer belt material 102 be somewhat elastic itself, the belt spring 114 may not be necessary. The belt spring 114 assists in providing compliance to the system during muscle contraction, and experiments have shown it dramatically decreases the pressure spike in the gas bladder 103 under muscle contraction when the outer belt material 102 is, for example, polyurethane coated ballistic nylon 800 denier. The belt spring 114 may be made of any elastic material such as similar material to the inner belt material 101, of any suitable width, or may simply be an extension of the inner belt material as an integral piece, such that the overall elastic properties allow for optimal compliance of the assembly under muscle contraction.

A belt fastening means 105 as depicted in FIG. 1K by a first fastening means 110, shown as a strip of hook or loop fastener, and a second fastening means 111 depicted by a strip of mating hook or loop fastener. The belt fastening means 105 is used to lock an outer circumference of the inflatable belt 100 when applied around a user's limb (not shown). The reader may note that many such fastening means are known in the art, and hook and loop fasteners are but one version. Further such variations are described below, and the reader may note these are but a few examples and may not limit the scope of this invention. The first fastening means 110, or second fastening means 111, may in fact have itself elastic properties and serve as the function of a belt spring 114 (described later), thereby eliminating an extra component. The first fastening means 110 may be in communication with the an end of the second fastening means 111 via attachment means such as sewing, and the second attachment means in communication with the outer belt material 102. As previously stated, if sewing is used, care is taken not to puncture the gas bladder 103. The second fastening means 111 may run along the length of the outer belt material 102, or only along a portion thereof. Further, should the inner belt material 101 be made wider than the outer belt material 101, the second fastening means may be attached to the inner belt material only. The reader may note this is one example of the many combinations and possibilities of combining components, varying their sizes etc, and all such configurations may be considered within the scope and spirit of this invention. The second fastening means 111 may overhang one end of the gas bladder 103 as shown in FIG. 1K to provide a length of the inflatable belt 100 that is not covered by the inflatable bladder 103. In this manner, the total length of the belt, when laid flat, is only partially covered by the gas bladder 103. In such a configuration it may be desirable to have the gas bladder 103 equal the length of the smallest arm circumference of the expected user such that the gas bladder 103 never overlaps itself. In this case, for the smallest arm circumference the gas bladder 103 will butt up against itself, and for all larger users the gas bladder will cover only a portion of the circumference of the limb. This may be suitable for users up to the point where the gas bladder covers less than 30% of the limb circumference as shown in experiments to achieve adequate BFR. This is, but an example, and the gas bladder may also run the length, or substantially all of the length, of the belt and belt fastening means 105 as well. Alternatively, the gas bladder 103 may have a portion that is connected to the fastening means 105 and portion that is not connected to the fastening means as in design shown in the referenced application 62/311,936. In this the configuration the gas bladder 103 may overlap itself to accommodate a limb circumference smaller than the length of the gas bladder. Such configurations and concepts are extensive covered in 62/311,936 and shall not be repeated here, but rather incorporated in by reference. The first fastening means 110 may be attached to the end of the second fastening means 111 such that it may double-back through a loop coupler 115, and attach to the second fastening means 111 in the case of a fold-back style belt. Alternatively, if the second fastening means 111 is not extended beyond the end of the outer belt material 102, the first fastening means 110 may itself be connected to the outer belt material. The reader may note again that many combinations and variations are possible and all such configurations that result in a fastening of the inflatable belt 100 to limit the circumference of the belt, or restrain the circumference from expanding, when placed on a user and inflated may be considered herein.

Figure 1K:
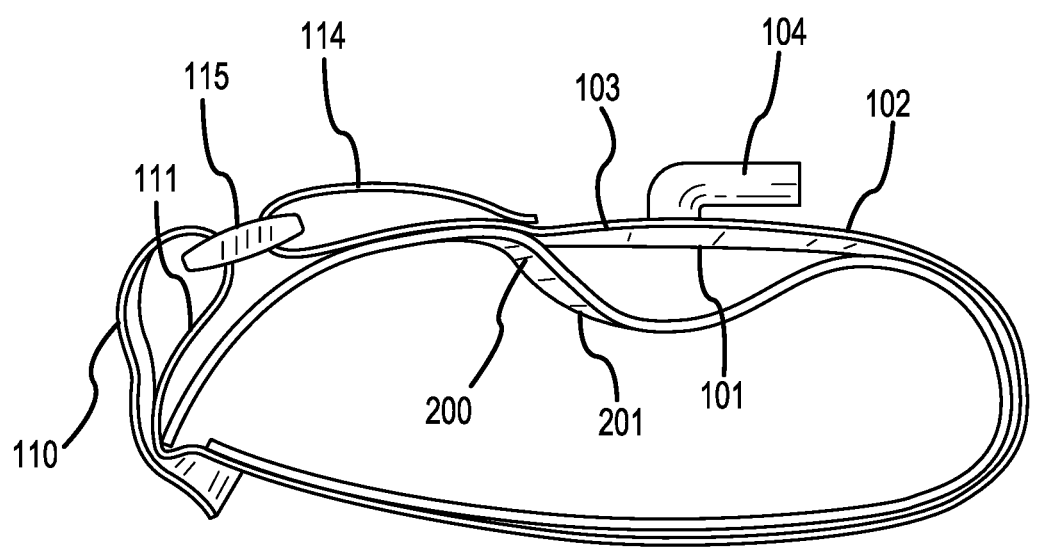
FIG. 1K—shows fold-back design of an inflatable belt with an outer belt material, an elastic inner belt material connected to the outer belt material and forming a gas bladder, in input port for accepting air into the gas bladder, a body interfacing component, and hook and loop fasteners for a belt fastening means, a belt spring element coupled to a loop coupler in the form of a D-ring, and the hook fastener passing through the loop coupler to double back and affix to the loop fastener.
Figure 1L:
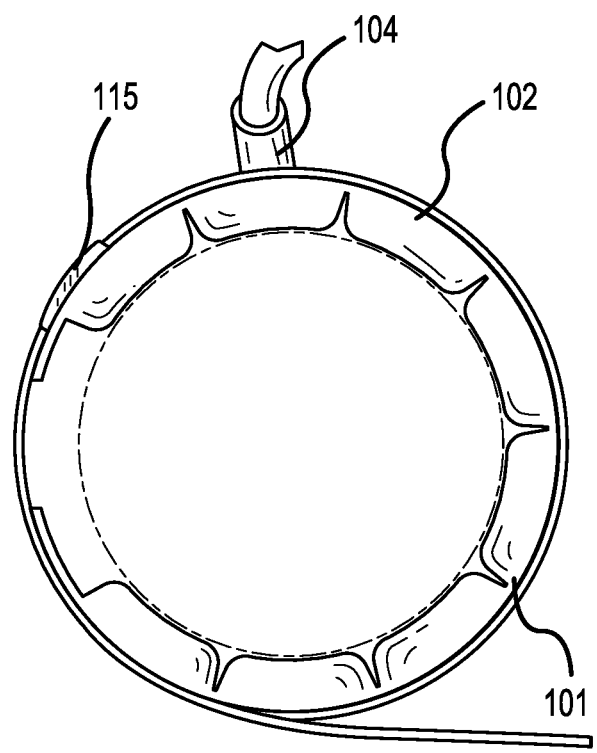
FIG. 1L—shows two versions of FIG. 1K where one is pre-stretched, and demonstrates smooth contouring and no kinking, and one is not pre-stretched and demonstrates visible kinking.
Figure 1L:
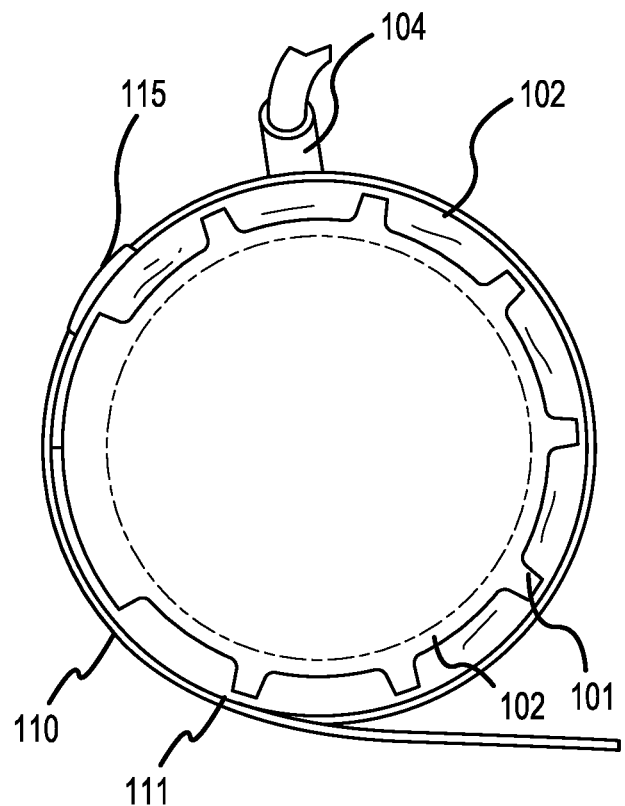
Figure 2D:
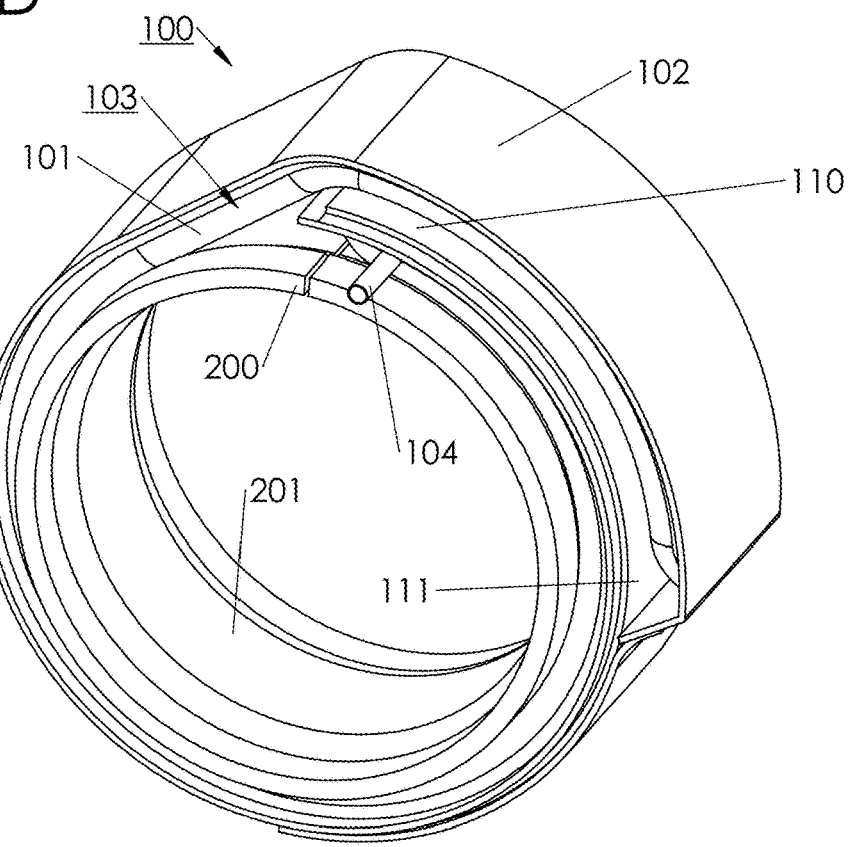
FIG. 2D—shows the inflatable belt plus body interfacing component assembly in the proper initially tensioned configuration with the two ends of the body interfacing component butting up together.

An optional body interfacing component 200 may be provided in communication with the inner belt material 101. The body interfacing component 200 is not required for sufficient functional operation of the inflatable belt of FIG. 1K, or other embodiments for that matter, but can offer some distinct advantages. As depicted in FIG. 1K, the body interfacing component 200 may be a strip of neoprene rubber, approximately 1.5 mm thick. Strips up to 5 mm thick were tested and all provide sufficient properties as herein discussed. The body interfacing component 200 preferably has a frictional surface 201, or in the case of the neoprene rubber, a "skin" side that is faced inward to contact the user. This high friction surface 201 may grab the user, or user's clothing such that rotation during initial tensioning is not observed. Further, the body interfacing component 200 spaces the gas bladder 103 off of the limb, in the case of FIG. 1K, by 1.5 mm. This gap between the gas bladder 103 and the user's limb (not shown) is significant because it prescribes a certain volume that the gas bladder may inflate into, prior to starting compression of the user's limb. In the case of FIG. 1K, where neoprene is used for the body interfacing component 200, the gas bladder 103 will compress and squish the neoprene material directly underneath out to the side and thin out underneath the gas bladder, and while the full volume filled by the neoprene is not vacated, enough is to allow for substantially more air to fill into the gas bladder prior to starting significant compression on the user's limb than would otherwise be allowed if the gas bladder were laid flat against the limb as in the belts of Sato. The body interfacing component 200 is further needed to facilitate donning of the inflatable belt 100 because, should the user want to employ this concept of spacing the gas bladder 103 off the surface, without the body interfacing component, there would be no friction or connection to the body (the gap would be filled with air) and this would cause the inflatable belt to slip down on, and rotate freely around the arm, and be very difficult put on. This phenomenon was in fact demonstrated in experiments leading to the invention of the body interfacing component 200, where the applicant felt a gas bladder directly against the limb was overly constricting, but when a second person held the gas bladder off the limb to allow for more inflation, the comfort level was substantially improved and pressure spikes reduced. The body interfacing component 200 further helps to guard the user's skin against pinching. Pinching is a result of kinking of the gas bladder 103 that can be observed in FIG. 1L where there are kinks in a inflatable belt 100 that has not been pre-stretched. The body interfacing component 200 takes the pinching from the kinks in the gas bladder 103 on the outer surface of the body interfacing component, but because of the significant thickness, the kink is dispersed along the thickness of the body interfacing component to where there is no more kink on the inner friction surface 201, which is against the skin, and thus no kink, and no pinching, is transmitted to the user's skin. This pinching phenomenon was another observed problem with Sato's equipment where Sato only contemplates a thin liner, and not something that will disperse and eliminate kinks. The body interfacing component 200 further serves to distribute the applied load from the gas bladder 103 across a certain width, and on to the user's limb. It is an important property of the body interfacing component that it be squishy to a sufficient degree so as to maintain a soft squishy interface to the user to provide maximum comfort, but be able to move and allow room for the inflatable bladder 103 to expand prior to compressing the user's limb. Comfort was seen in experiments to be dramatically improved by addition of the body interfacing component 200. The body interfacing component 200 may be permanently connected to the inflatable belt 100 as shown in FIG. 1K, or may be removable and attachable as shown in FIG. 2A, B, C, or may be applied prior to application of the inflatable belt, and not attached to the inflatable belt at all. In the case the body interfacing component 200 is attached to the inflatable belt 100, such attachment may be done with sewing, bonding or similar means. In the case the body interfacing component 200 is removable, the body interfacing component may further comprise or have fixed to it, a first fastening means 110 as shown in FIGS. 2A, B, C and a mating second fastening means 111 similarly attached to the inflatable belt 100. The attachment means may be any such means, such as hook and loop fasteners, described or inferred to herein. The body interfacing component 200, in the removable case, may serve an important function in that, as shown in FIG. 2A, it may be measured by the user to match an arm circumference, or slightly less, for example 80-95% of an arm circumference. In this way, a standard prescribed length of the body interfacing component 200 can be instructed to all users, in a consistent guideline requiring no prior BFR experience, since measuring an arm circumference is something any ordinary user is capable of. This is another detriment to Sato's designs, in that there is no guidelines for where to start the initial tension of the belt, and this has been shown to have a dramatic effect on the efficacy, safety, and comfort of KAATSU Training. KAATSU, the company, publishes protocols for determining this starting tension, but the protocols require much trial and error and even multiple KAATSU Training sessions to start to narrow in on what is right for the individual. Solving this problem, of recommending in a consistent way, to novice users, how to properly tension the bands, provides a very big advantage in ease of use, to spread mass adoption. The length prescribed may be such that only very mild tension is initial applied once the inflatable belt 100 is placed on the user's limb 90. Once the measurement is made, the user may cut a provided body interfacing component 200, or similarly fold it back, but in some way reduce the length to the prescribed amount for a given limb girth. Then the user may apply the body interfacing component 200 to the inflatable belt 100, connecting the two mating fastening means such that each end of the body interfacing component butts up against each other as shown in FIG. 2D. In this way, the body interfacing component 200 now serves as a reference guide so that when the user goes to place the inflatable belt 100 on their arm, they must only pull the portion of the inflatable belt meant to feed through the loop coupler (which may or may not include the gas bladder 103) through the loop coupler 115 until the two ends of the body interfacing component butt up together. In fact the shape of the body interfacing component 200 may be such that it physically cannot go through the loop coupler and thus serves as a simple, hard stop, requiring no thinking or expertise by the user in how tight to apply the initial tension, and further guaranteeing that the user cannot over tension the inflatable belt 100 which provides a further safety advantage. The attachment means for connecting the body interfacing component 200 to the inflatable belt 100 may be two strips along each side as shown in FIGS. 2A, B, C or may be a single flat strip across the entire width. In the case of a single strip however, since the attachment means is blocking the gas bladder 103, the attachment means should itself have similar squishy properties as the body interfacing component, or else may block the gas bladder from expanding sufficiently and compressing enough of the limb. The use of hook and loop fastener is mainly discussed here because of its simplicity, but adhesive backed tape, magnets, or other non-permanent fastening means may also be used. Another advantage of a removable body interfacing component 200 is that for hygienic reasons, the body interfacing component may be swappable as the human/belt interface and not only may users have their own person body interfacing components, but they may also be disposable. In the case of a hospital setting for example a disposable body interfacing component 200 may provide a distinct health advantage. Thus it can be seen that, while optional to the function of the inflatable belt in providing BFR, the body interfacing component 200 can serve a variety of important roles to improve both the comfort, ease of use, and safety of the inflatable belt 100. The body interfacing component 200 may be of sufficient width, length and quantity to serve one or all of the above described functions, and does not need to fulfill all the requirements above to be considered valuable.

Not shown is an optional stop mechanism that prevents the first fastening member 110 from exiting the loop coupler 115, and thus keeps the inflatable belt 100 in a substantially ring like shape. This can aid in donning the inflatable belt 100 as the user does not need to fiddle with feeding the first fastening means 110 though the loop couple 115. Such a stop mechanism may be a physical barrier such as a bar or tab that is fixed with suitable means, such as sewing, to the first fastening means 110 or second fastening means 111 and mechanically interferes with the loop coupler 115 such that the first fastening means cannot physically pass back through the loop coupler. This is but one example and the reader may not there are many ways to prevent an object such as the first fastening means 110 from passing back through the loop coupler 115.

Preferred Embodiment Operation. The inflatable belt 100 of FIG. 1K is applied as follows in conjunction with a BFR system. First, a user (not shown) selects an appropriate size of inflatable belt 100 based on their limb girth. For illustration purposes, we will discuss application to an arm, but the reader shall note any segment of a body may use these concepts. If a body interfacing component 200 is provided, and if the body interfacing component is removable, and has not been customized to the user, the user first measures their arm girth, and then cuts the body interfacing component down to a prescribed length which may be equal to, or slightly less than their measured arm girth. Multiple such body interfacing components 200 may be provided or purchased and each individual may have their own personal set. Being removable has a further advantage that the body interfacing component 200 may act as a sweat barrier and in case of medical applications, where sanitation is paramount, provides a cheap, simple means of swapping components from one use to the next and washing separately for each individual user. The user then attaches their body interfacing component 200 to the inside of the inflatable belt 100, if attachment means is provided, or alternatively if the body interfacing component is not meant to be attached to the inflatable belt, the user simply puts the body interfacing component in the proper location on their arm.

Next, the user takes the inflatable belt 100, which may be held in loop form, but is not necessarily so, and slips it over their arm or leg into the desired position as described in Sato and referenced herein. Then the user takes the first fastening means 110 and pulls it further through the loop coupler 115 until the desired tension is reached, which may be, but is not necessarily, dictated by the body interfacing component 200, if provided. As the user starts to pull the first attachment means 110, the side of the inflatable belt 103 opposite the loop coupler 115, first comes in contact with the user's skin or clothing. As preferred, the optional body interfacing component 200 is preferably employed with friction surface 201 facing inward and the friction surface contacts the user's skin or clothing. Because of the high frictional coefficient, the body interfacing component 200 grabs the surface and resists rotation, allowing the user to pull the inflatable belt 100, reasonably snug. Should the inflatable belt 100 require a high initial tension, as in the case of KAATSU equipment, the rotational force could overcome the frictional force resisting rotation and the inflatable belt could spin in an undesirable manner as Sato describes. This of course applies only to putting the inflatable belt 100 on oneself, as only one hand can easily reach the inflatable belt. If putting the inflatable belt 100 on someone else, the problems related to rotation are irrelevant. Because the optional body interfacing component 200 is spacing the gas bladder 103 sufficiently off the limb's surface, thereby providing significant volume increase for the gas bladder 200 to expand into, a low initial tension just to keep the band in place is all that is required and thus rotation is not a problem.

Thus ends the most basic method of operation of a basic inflatable belt 100, and tensioning system design to construct an inflatable belt, apply the inflatable belt to the user, and prepare the inflatable belt for inflation. For completeness, the full system operation will further be discussed in this preferred embodiment as related to system embodiments depicted in FIGS. 1D-1 and 1D-2.

Figure 1B:
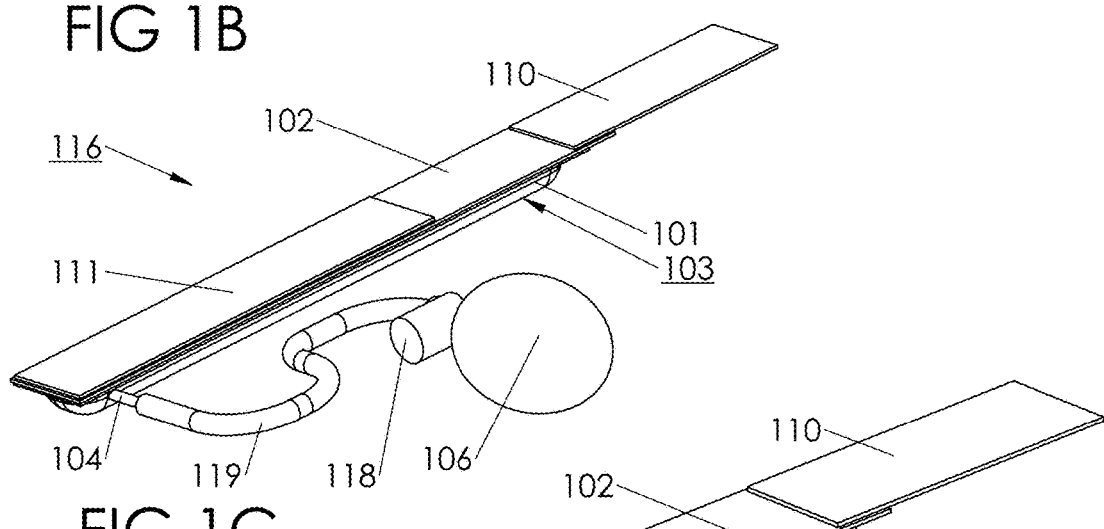
FIG. 1B—shows the inflatable belt of FIG. 1A-1 with an inflation means permanently connected to the input port, the inflation means further comprising an adjustable release valve.
Figure 1C:
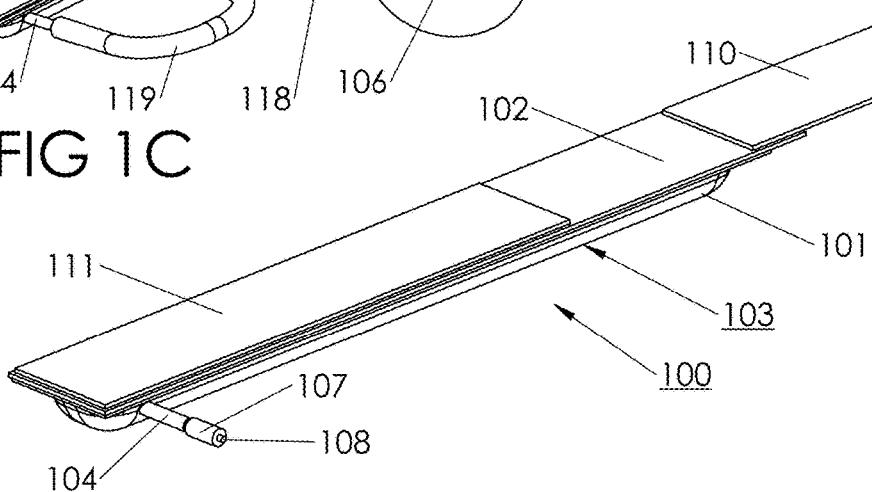
FIG. 1C—shows the inflatable belt of FIG. 1A-1 with a belt valve to maintain pressure in the inflatable belt when disconnected from an inflation means.
Figures 1, 1D:
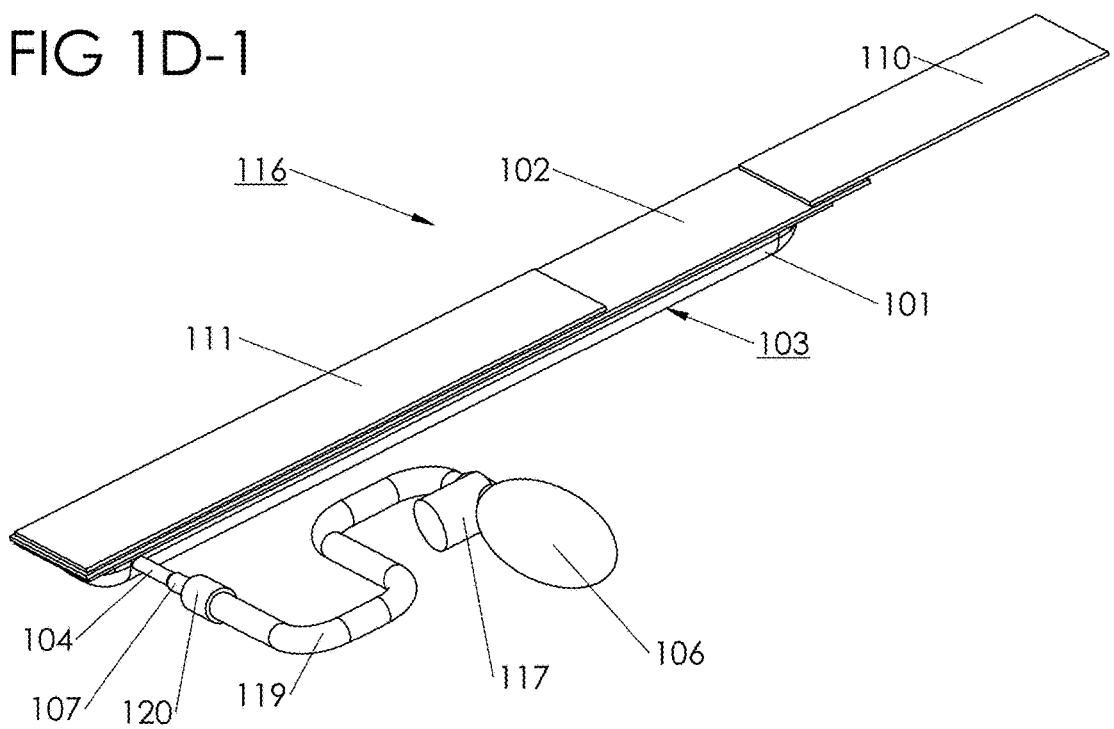
Figures 1, 1D, 2:
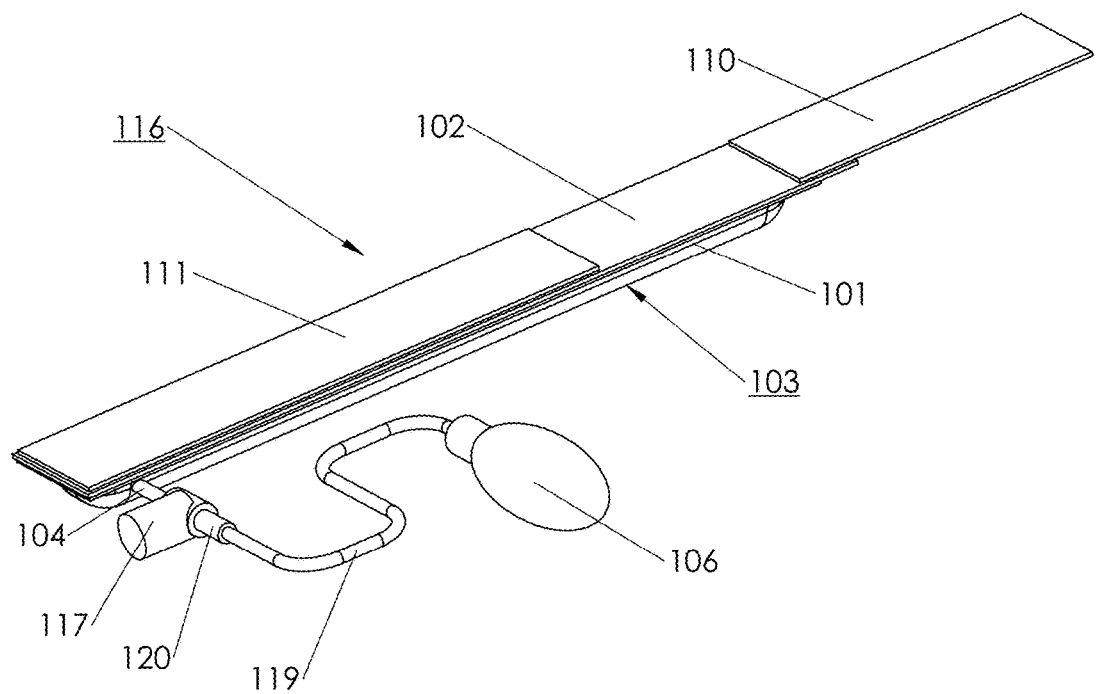
Figure 1E:
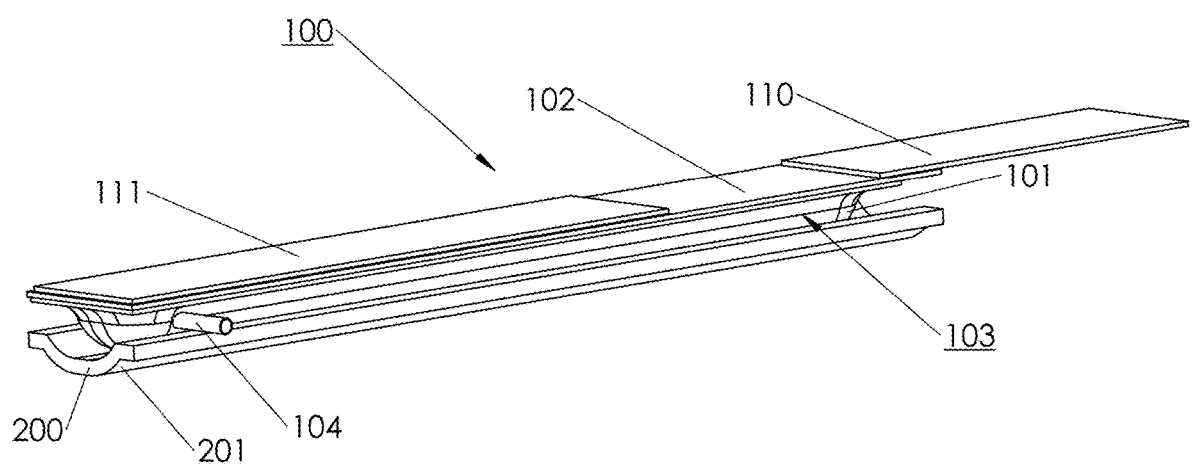
FIG. 1E—shows the inflatable belt of FIG. 1A-1 with an additional body interface component in communication with the inner belt material.

Once tensioned, the inflatable belt 100 may be connected, if not already permanently connected as shown in FIG. 1B, with an inflation means 106, and additional valves and optional components as will be discussed later. While not required, for example as shown in FIG. 1B, a belt valve 107, preferably employing a gas flow shutoff means 108, may come with, and remain attached to, the input port 104 of the inflatable belt 100 as shown in FIG. 1C on a straight overlap style belt. In this case the gas flow shutoff means 108 may be a spring plunger or duckbill valve, or any other means of holding air within the gas bladder 103 when the inflation means is disconnected. A valve coupling 120 may be configured to mate to the belt valve 107 in a quick connect type fashion to make clipping and unclipping of the inflation means 106 very simple and fast as shown in FIGS. 1D-1 and 1D-2. Many such valves are described in this specification and the reader shall note that an endless variety of such valves exist and all such mechanisms that perform the functions herein described may be considered within the scope of this application. If not permanently connected as shown in FIG. 1 B, an inflation means 106 may be connected to belt valve 107 via valve coupling 120. The inflation means may be a manual latex or PVC squeeze ball as depicted in FIGS. 1D-1,2 and seen on standard blood pressure cuff devices, or may be a different kind of gas pump, including an electromechanical pump. If the belt valve 107 employs a gas flow shutoff means 108, this means is preferable deactivated automatically upon connection of the valve coupling 120, as many such existing quick connect valve combinations function.

Figure 7A:
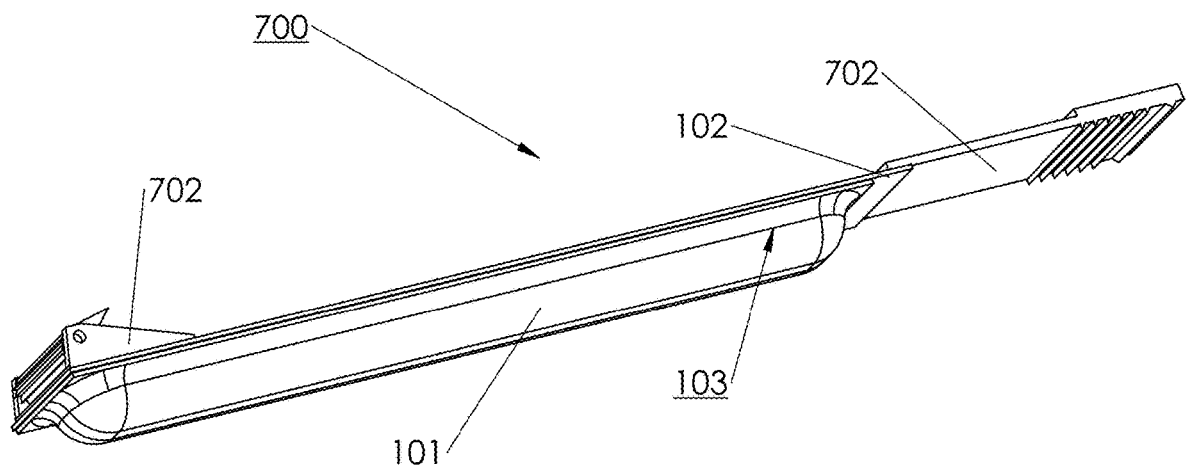
FIG. 7A—shows a pre-inflated belt encompassing a fixed volume of gas, with an outer belt material, an elastic inner belt material connected with the outer belt material to form a gas bladder, a tensioning means, for example a ratchet style mechanism, to fix a circumference of the belt around a user's limb, and no input port or means of gas entering or leaving.
Figure 7B:
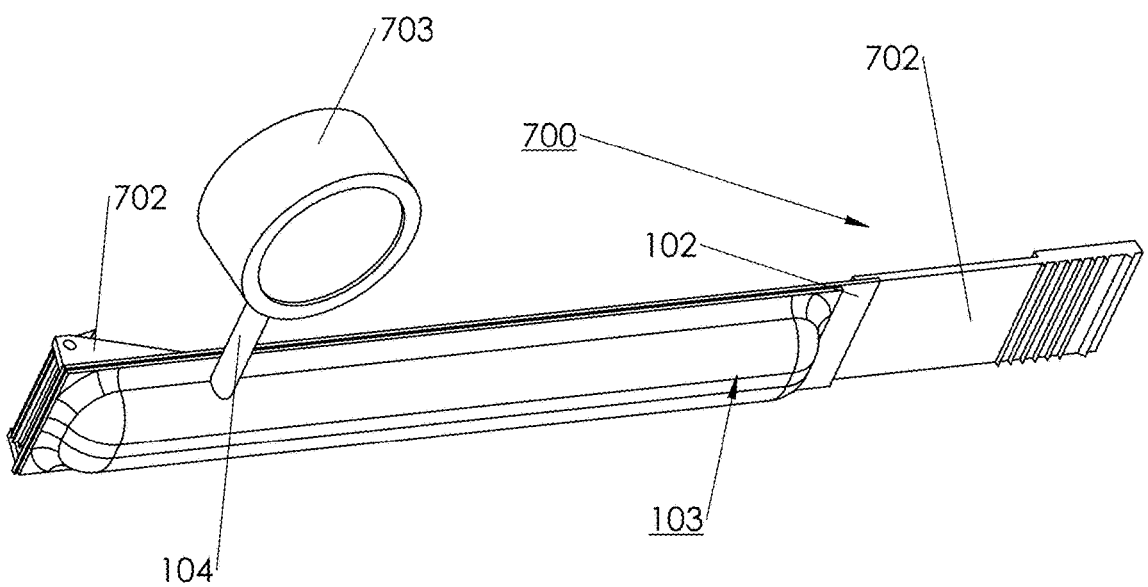
FIG. 7B—shows the pre-inflated belt of FIG. 7A with an additional input port and pressure readout to know a pressure in the gas bladder when tensioned around a user's limb.
Figure 8A:
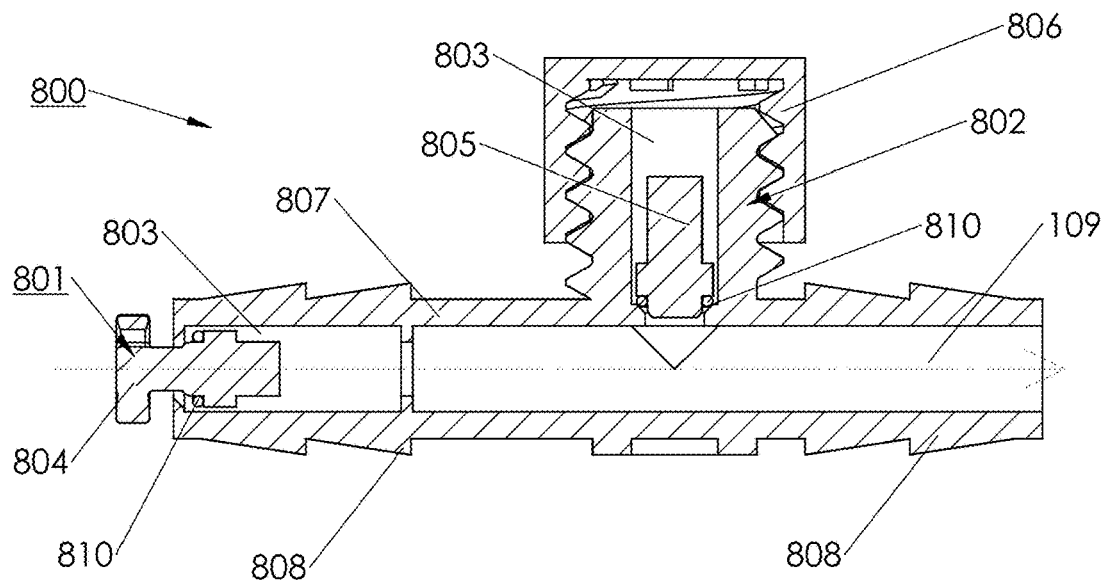
FIG. 8A—shows a pressure relief valve combo comprising a manual relief actuator in-line with an air flow, and an adjustable pressure limiting valve to pre-set a predetermined pressure cutoff to limit the pressure in an inflatable belt for use in BFR training.

Gas, preferably air, is next injected into the gas bladder 103 by inflation means 106 until a desired pressure is reached. A desired pressure may be indicated by a pressure readout 703 as shown in FIG. 7B, but adapted to the configuration of inflatable belt 100 shown in FIG. 1D-1,2, or other figures in this application. The reader shall note that it is well understood in the art how to connect or insert a pressure readout into a pneumatic system. In place of a pressure readout 703, a pressure limiting valve 117 may provide an upper pressure limit above, and the pressure limiting valve may release air until the pressure has dropped such that the pressure limiting valve resets and seals the opening. Such check-style, or pop-off, valves are well known in the industry and any such method or means for accomplishing pressure limiting may be considered within this scope. The pressure limiting valve 117 may be easily swappable, allowing for quick replacement for different users, or may be permanently connected, or may itself be adjustable, for example through mean such as shown in FIGS. 8A, B, or otherwise non-adjustable. Adjustability of the pressure limiting valve 117 will be discussed further below but may be done with different springs, or initial compressions of a given spring, and many such methods are commonly known in the field of pneumatic relief valves. The pressure limiting valve 117 may come with or without markings to indicate the maximum, or "pop-off", pressure setting. An advantage of the pressure limiting valve 117 may be that the user does not need to think or try and precisely inflate the inflatable belt 100, but can just pump the manual inflation means 106 until the pressure limiting valve activates, further simplifying use. Finally, an electromechanical pressure control system such as in FIGS. 9 A, B may be used to serve a similar function to the pressure limiting valve 117.

Once the desired pressure is achieved in the inflatable belt 100, the valve coupling 120 may be disconnected from the belt valve 107, and the gas flow shutoff means 108 may retain the pressure in the inflatable belt, and the user is free to move around and do various exercises without additional equipment attached that adds weight, bulk, and encumbers movement.

When the user is through with the desired exercises, the user may use an optional manual relief actuator 801, if provided, that is preferably, but not necessarily, part of the belt valve 107, to release the pressure in the gas bladder 103 and deflate the inflatable belt 100 to a low tension on the arm. The user then removes first fastening means 110 and pulls the inflatable belt 100, still preferably kept in loop form, off of their limb. The user may then remove the body interface component 200, if the component is configured to be removable, and may wash it, or replace it with a different one for a next user.

Alternate Embodiment—#1. FIGS. 1A-1 and 1A-2 depict an alternate embodiment wherein the inflatable belt 100 is configured to be fastened in a straight overlap configuration. The two principal configurations shown in the figures in this application are either of a straight overlap configuration or a fold-back configuration. Sato discusses some of the advantages and disadvantages of each style that need not be repeated here. In FIG. 1A-1 a gas bladder 103 is formed from an outer belt material 102 connected in a hermetically sealed fashion along a portion thereof, to an inner belt material 101. Widths, lengths and connection methods are substantially similar to the preferred embodiment. An input port 104, substantially similar to the input port of the preferred embodiment is in communication with the gas bladder 103. A first attachment means is in communication to one end of the outer belt material 102, such that a portion of the first attachment means 110 overhangs the end of the outer belt material. Alternatively the outer belt material 102 may be longer than the inner belt material and serve as a backing for the first attachment means 110, which may therefore be attached to the same side of the outer belt material as the inner belt material 101 is attached to. Alternatively still, the inner belt material 101 may be longer than the outer belt material 102 such that a portion overhangs the outer belt material 102. In this case the first attachment means 110 may be connected to the bottom surface of the inner belt material. Further still, since the inner belt material 101 is elastic, if a portion of the inner belt material, overhanging the outer belt material 102, is left uncovered by the inelastic first fastening means 110, this uncovered portion may serve as the belt spring 114 and further reduce components and make the construction more economical. Should the first fastening means 110 itself be elastic, there may be no need for an uncovered portion of the inner belt material 101.

FIG. 1A-2 shows the straight overlap style inflatable belt 100 of FIG. 1A-1 but in a wrapped configuration. To don the inflatable belt 100, the user would place one end on their limb and simply wrap the other end around their limb, overlapping appropriately so as to develop appropriate tension. The reader shall note that while not shown, the body interfacing component 200 may be used to provide all the advantages discussed previously. Once wrapped to the appropriate length, the user would secure first fastening means 110 to second fastening means 111 to lock the circumference of the inflatable belt 100. The inflation and usage of the inflatable belt 100 of FIG. 1A-1,2 is substantially similar to the preferred embodiment in reference to connection/disconnection of inflation means 106 and employment of belt valve 107 or pressure limiting valve 117, and other components described in the preferred embodiment.

Alternate Embodiment #2. FIG. 1B depicts an alternate embodiment of a blood flow restriction system 116 wherein the inflatable belt 100 is permanently connected with the inflation means 106 through a gas hose 119. The gas hose 119 may be further in communication with an adjustable release valve 118, shown positioned near the inflation means 106, but not necessarily so located. The adjustable release valve 118 may alternative be a pressure limiting valve 117. Permanent connection of the inflation means 106 has an added benefit of part count reduction further simplifying the system and reducing price. Such a configuration may be well suited for applications where the user will remain substantially stationary while doing basic movements, such as a rehabilitation setting. "Permanent", as stated in this specification, may be taken to mean semi-permanent where certain connections, for example a hose barb, may be disconnected from time to time, but are not necessarily intended for repeated connect/disconnect cycles.

The inflation and usage of the inflatable belt 100 of FIG. 1 B is substantially similar to the preferred embodiment in reference to connection/disconnection of inflation means 106 and employment of belt valve 107 or pressure limiting valve 117, and other components described in the preferred embodiment.

Alternate Embodiment #3. FIG. 1C depicts a modification of FIG. 1A-1, with the inflatable belt 100 connected further with a belt valve 107, and the belt valve further incorporates a gas flow shutoff means 108, such as a check valve, or any other such one way valves as herein disclosed. The inflatable belt 100 in FIG. 1C may come pre-populated with the belt valve 107 and may therefore be considered part of the assembly in this configuration. Such a belt valve 107 may further be configured for quick connect/disconnection functionality such as a spring loaded clasp or break away connection from a valve coupling 120 as shown in FIG. 1D-1. In such a scenario, the valve coupling 120 may be designed on connection to de-activate, or override the gas flow shutoff means 108, generally with a mechanical action, such that the air path is clear for gas, or air, to flow from the inflation means 106 into the gas bladder 103.

The inflation and usage of the inflatable belt 100 of FIG. 1C is substantially similar to the preferred embodiment in reference to connection/disconnection of inflation means 106 and employment of belt valve 107 or pressure limiting valve 117, and other components described in the preferred embodiment.

Alternate Embodiment #4. FIG. 1D-1 shows the inflatable belt of FIG. 1C, with the valve coupling 120 and inflation means 106 connected and the gas flow shutoff means 108 is de-activated. FIG. 1D-1 further shows a pressure limiting valve 117, that may be adjustable, in communication with a gas hose 119 such that when a pressure in the gas hose and air bladder 103 circuit is higher than a pre-determined value, the pressure limiting valve releases as much air as necessary to drop the pressure in the air circuit back below the maximum pressure allowed by the pressure limiting valve. The pressure limiting valve 117 may have a single fixed pressure limit value or may be adjustable and connected with a pressure readout (not shown) so that the user may control the actual pressure in the air circuit according to a visual pressure reading. When the desired pressure is achieved, the valve coupling 120 is disconnected and the gas flow shutoff means 108 activates, trapping a fixed volume at the desired pressure inside the gas bladder 103. The reader shall note that while FIG. 1 B, D-1 show two different valves, a pressure limiting valve 117 and an adjustable relief valve 118, both of these valves may have similar functions and designs, and in general are interchangeable in all described embodiments. The main difference is that the pressure relief valve 117 may be configured to automatically release pressure at the set limit, whereas the adjustable relief valve 118 may be manually turned to open and close.

The inflation and usage of the inflatable belt 100 of FIG. 1D-1 is substantially similar to the preferred embodiment in reference to connection/disconnection of inflation means 106 and employment of belt valve 107 or pressure limiting valve 117, and other components described in the preferred embodiment.

Alternate Embodiment #5. FIG. 1D-2 shows a similar configuration of a blood flow restriction system 116 as FIG. 1D-1, however the belt valve 107, has been removed and replaced with the pressure limiting means, shown as pressure limiting valve 117. In this case, the pressure limiting valve 117 must be able to accept air into an inlet, yet prevent air from releasing out of the gas bladder 103 until a limit pressure is reached. The pressure limiting valve 117 may have a pre-set limit where no pressure readout (not shown) is needed, and may incorporate a one way valve in addition to the pressure limiting feature, or in combination with the pressure limiting feature, to prevent backflow out of the intake. Alternatively, the pressure limiting valve 117 may simply be a manual twist-to-release valve, or adjustable relief valve 118, as commonly seen on blood pressure cuffs, which is configured to always allow air flow into the gas bladder 103 and manually opened to allow air flow out at a flow rate proportionally to the degree of twist. In such manner, when inflation means 106 is coupled via valve coupling 120 and too much air is pumped into the gas bladder 103, the adjustable relief valve 118 may be twisted to release air until a desired pressure is reached, and then twisted closed to prevent further leakage, thereby trapping the desired air pressure in the gas bladder. In this case it may be desirable to attach a pressure readout 703 (not shown) in communication with the gas hose 119 in between the adjustable relief valve 118 and the inflation means 106, so that the user can visibly regulate the pressure to the desired level and then decouple the pressure readout, gas hose, and inflation means by disconnecting valve coupling 120. The reader can clearly see that the present inventor is illustrating various ways of combining valve types and features for preventing, limiting, or allowing air flow within an air circuit, and various combinations may have advantages and disadvantages in terms of ease of use and manufacturability, or availability of off the shelf components, however all such combinations, whether currently existing or custom designed, may be considered within the scope of this application. The pressure limiting valve 117 however may offer a significant advantage over the adjustable release valve 118 in that it requires no thinking or titrating of the pressure, and does not require the cost of the pressure readout 703 or attachment means to the gas hose 119, thereby reducing cost, bulk, and increasing ease of use.

The inflation and usage of the inflatable belt 100 of FIG. 1D-2 is substantially similar to the preferred embodiment in reference to connection/disconnection of inflation means 106 and employment of belt valve 107 or pressure limiting valve 117, and other components described in the preferred embodiment.

Alternate Embodiment—#6. FIG. 1 E shows the straight overlap style inflatable belt 100 of FIG. 1A-1 with an addition of the body interfacing component 200. The body interfacing component 200 may be substantially similar to that described in the preferred embodiment. The body interfacing component 200 may be permanently fixed to, or detachable from to the inner belt material 101 at one or more points along the surface, preferably the perimeter, or may be simply loose fitting, or removable, and completely separate from the inflatable belt 100. In the case the inflatable belt is a separate assembly, the user would don the body interfacing component 200, after going through the process of trimming it to the appropriate length as discussed in the preferred embodiment, place the friction surface 201 facing against their limb, and securing the body interfacing component to itself with a fastening means (not shown) to hold the body interfacing component on their body. Then the inflatable belt 100 is applied around the body interfacing component, tightened to the appropriate degree and prepared for inflation as discussed prior. In the case of being separable, the body interfacing component 200 may have features that promote locating and holding to the inflatable belt 100 to keep the inflatable belt in a desired position, such as a trough design, adhesive surface, etc. In the case the body interfacing component 200 is fixed to the inflatable belt 100, the length of the body interfacing component may be, but is not necessarily, at least as long, and at least as wide as the inflatable bladder 103. The body interfacing component 200 may be shorter or longer than the inflatable bladder 103 but may not be so short as to fail to provide a single one of the benefits described in the preferred embodiment, and may not be so long as to provide bulk and interfere with tensioning of the belt. The body interfacing component 200 may be any width that provides at least one benefit as described in the preferred embodiment, but is preferably as wide, or wider than, the gas bladder 103 to facilitate connection to the outer belt material 102 along the edges, via, for example, stitching, bonding, or welding, or with non-permanent connection such as hook and loop fastener. As stated, the body interfacing component 200 may be attachable to the inflatable belt 100 via first attachment means 110 placed on the body interfacing component, and second attachment means 111 on the inflatable belt as shown in FIGS. 2A-C.

As previously discussed the body interfacing component 200 may be any material that has sufficient compliance to accomplish the benefits described in the preferred embodiment, and is preferably neoprene rubber, of reasonable thickness to provide the benefits, for example 1.5 mm thick, and with skin surface on at least one side. However a low durometer polyurethane, or latex would also suffice, and many other such materials and polymers may be used instead of neoprene rubber.

Figure 1F:
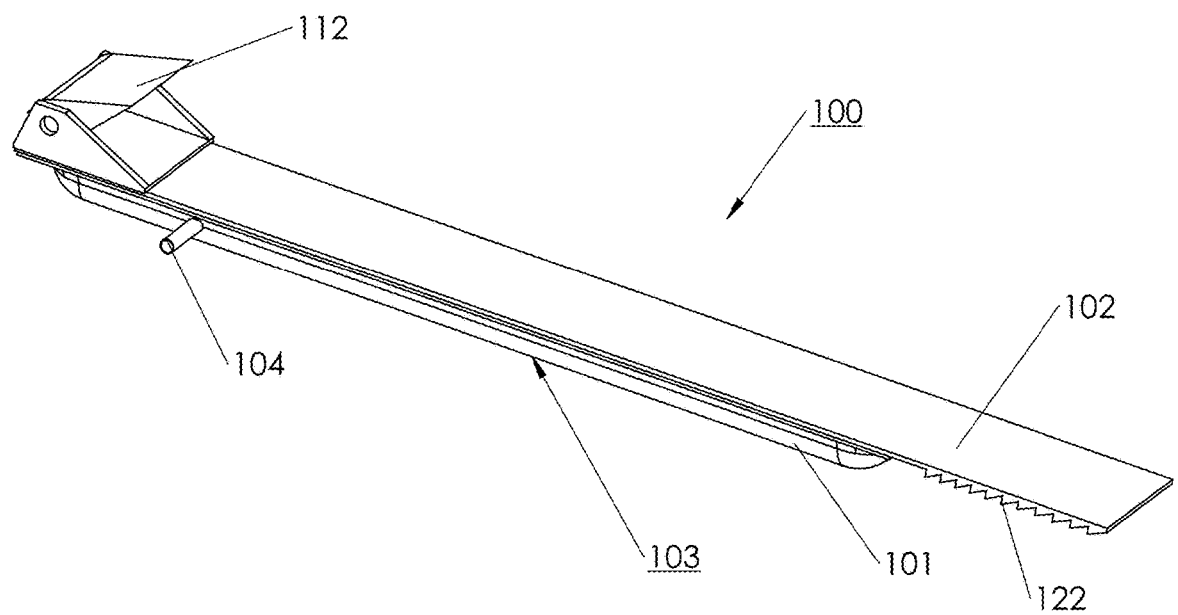
FIG. 1F—shows an inflatable belt design similar to FIG. 1A-1 wherein the belt fastening means is a ratchet style system.

Alternate Embodiment—#7. FIG. 1F shows an alternate construction for the straight overlap style band of FIG. 1A-i, employing a ratchet style mechanism 112 to lock the outer belt material 102 at a fixed circumference. The ratchet style mechanism 112 is shown connected to the end of the outer belt material 102 but may be additionally attached to a belt spring (not shown), which in turn is attached to the outer belt material. In this way, compliance is added to the inflatable belt 100, to provide comfort and reduce pressure spikes during muscle contraction. The ratchet style mechanism 112 is shown attached to the end of the inflatable belt 100, but may be attached anywhere along the length, for example in the middle or the inflatable belt. As previously stated, the input port 104 may be similarly located at any point along the length of the gas bladder 103, and is not restricted to placement at one end as shown. In this embodiment, additional features of the ratchet style mechanism 112 are added to the outer belt material 102 on the said where the inner belt material 101 exists. These features are represented by teeth 122 embossments, as those commonly seen in ratchet style mechanisms. These features may be applied to a surface of the outer belt material 102 that overhangs the gas bladder 103 as shown in FIG. 1F, or they may be attached to the end of the outer belt material and serve as an extension thereof. The teeth 122 and ratchet style mechanism 112 may be made of any material such as metal, plastic, or rubber to name a few, and are preferably flexible in nature to take a contour similar to the user's limb without providing a sense of bulk or abrasion to the user.

Figure 12:
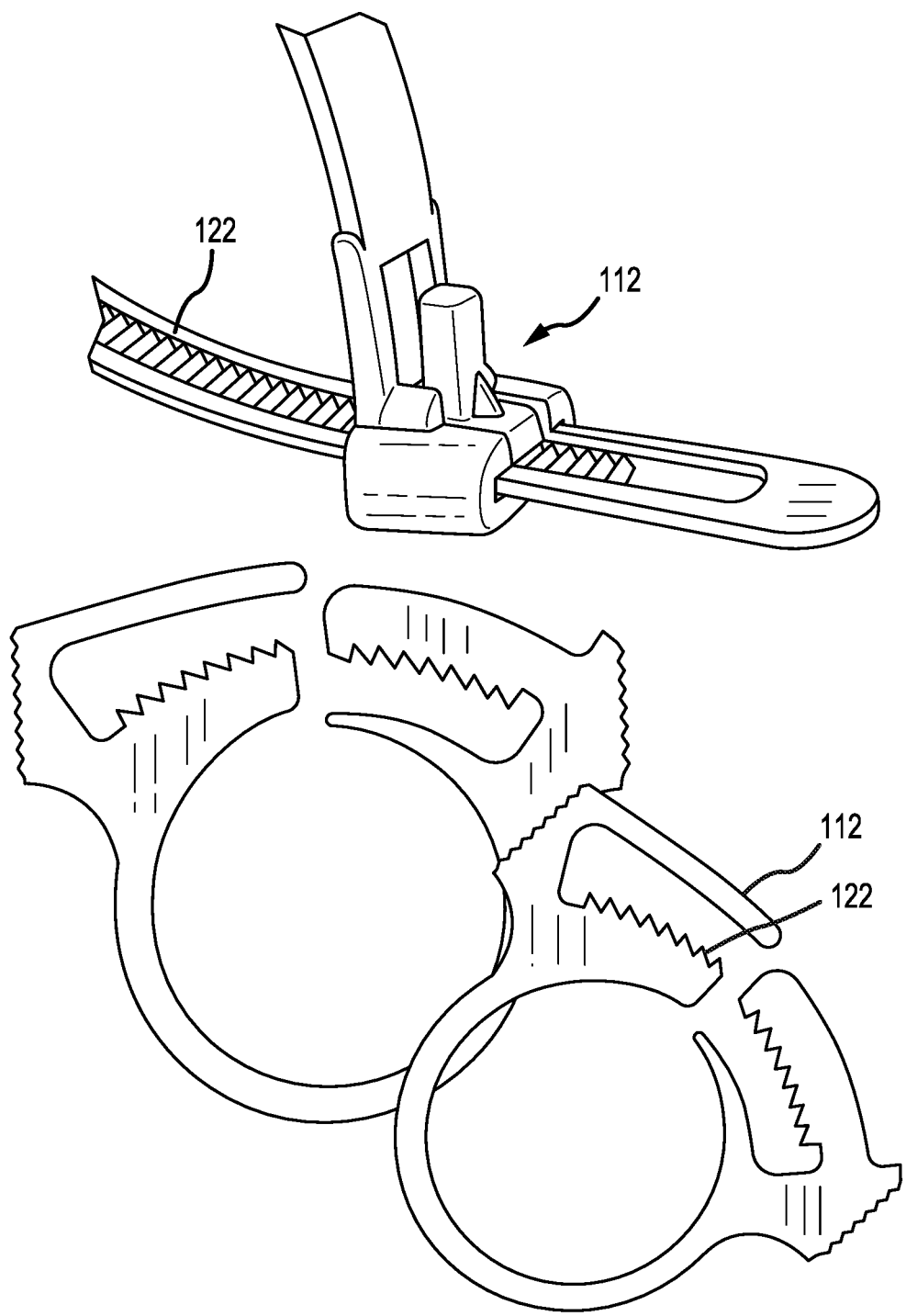
FIG. 12—shows some examples of ratchet style mechanisms that may be used to constrain the circumference dimension of the inflatable belt when applied to the limb.

When used, similar steps as to those described in the preferred embodiment are followed, and if applicable, the body interfacing component 200 (not shown) may be employed. The user feeds the teeth 122 through the ratchet style mechanism 112 and cranks the ratchet style mechanism down until a desired tension is reached. Alternatively re-useable zip tie style ratchet style mechanism 112, as shown in FIG. 12, may be employed relying on the user to pull the teeth 122 through the ratchet style mechanism 112 until the desired tension is reached, and the re-usable zip-tie style mechanism simply prevents the teeth from going back through the re-usable zip-lock style mechanism when the user releases the teeth, yet allowing the user to activate a lever that will release the teeth upon the user's actions.

The teeth 122 may further be permanently inserted into the ratchet style mechanism 112, such that they are not allowed to go fully back out of the mechanism, locking the inflatable belt 100 to a substantially loop-like shape at all times. This may aid in the usability as the user will simply need to insert their limb into the loop-like shape, and not need to feed the teeth 122 through the mechanism, and will simply need to activate the mechanism or pull the exposed section of teeth further through the mechanism to achieve the desired compression, or tension in the inflatable belt 100. This may be particularly beneficial on an arm belt design where only one hand is readily available.

The ratchet style mechanism 112 itself may act as a handle, or have an additional handle feature (not shown) to provide a similar technique for tightening as Sato describes in U.S. Pat. No. 8,992,397 where a user may use both hands to tighten the inflatable belt 100. In this case the ratchet style mechanism 112 itself may provide similar function to Sato's "second band shaped member", and the extra material passing through the ratchet style mechanism serves the function of Sato's "first band shaped member" in relation to how a user may grasp the inflatable belt 100 easily to tighten it down initially. The benefit being that the overall bulk of the mechanism is reduced, and there are not two "tails" that need to be dealt with to avoid flopping around during subsequent exercises; there is only one.

Figure 10:
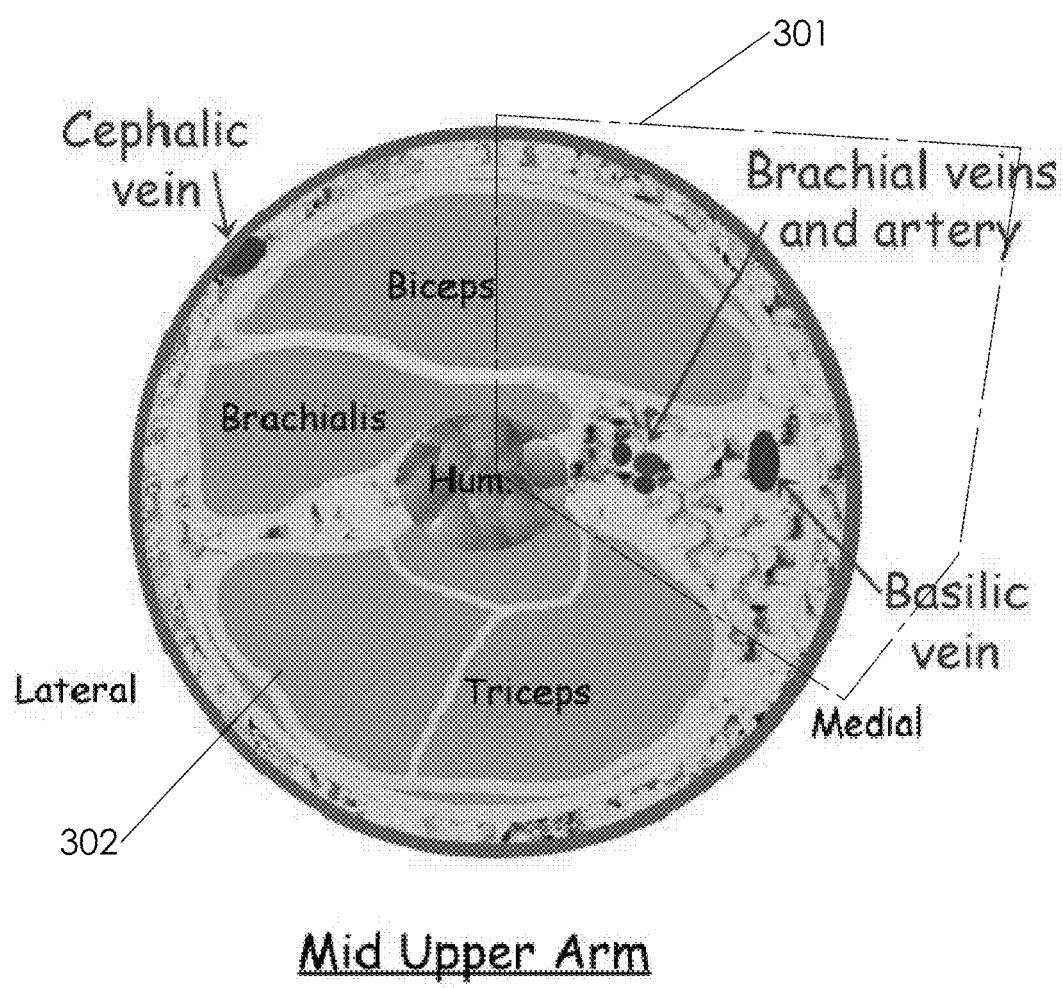
FIG. 10—shows a cross section of the arm in the vicinity where the inflatable belts should be placed, and highlights the location of the veins in the arm for targeting purposes.
Figure 11:
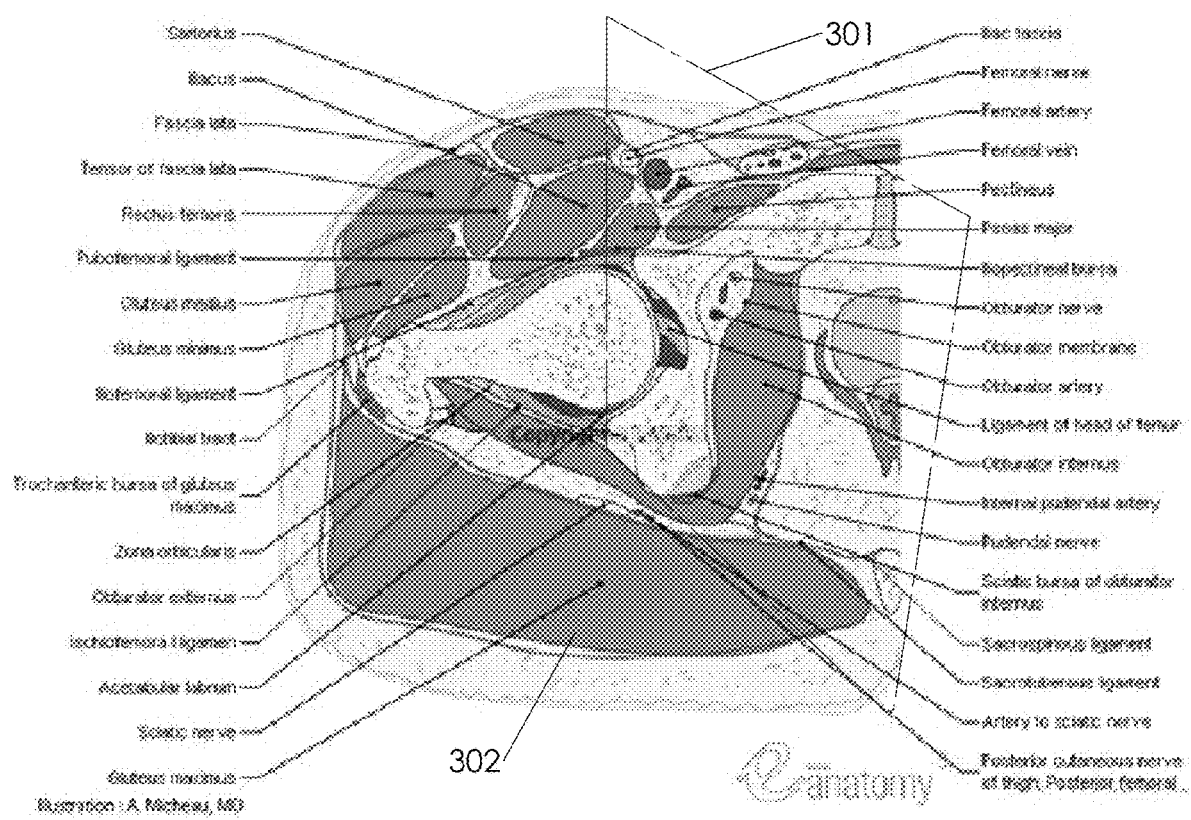
FIG. 11—shows a cross section of the leg in the vicinity where the inflatable belts should be placed, and highlights the location of the veins in the arm for targeting purposes.

A belt spring 114 (if used), cam-lock style mechanism 113, ratchet style mechanism 112, or loop coupler 115 are ideally located away from the deep venous target area. The ideal location for such components on the arms is the outer medial surface of the arm, and similarly for the legs, the outer medial surface as shown in FIGS. 10, 11. These locations are relatively flat, have only superficial veins that can be compressed by the non-gas bladder portion of the band, and do not experience much bulging or movement to impede or abrade during muscle contraction.

The inflation and usage of the inflatable belt 100 of FIG. 1F is substantially similar to the preferred embodiment in reference to connection/disconnection of inflation means 106 and employment of belt valve 107 or pressure limiting valve 117, and other components described in the preferred embodiment.

Figure 1G:
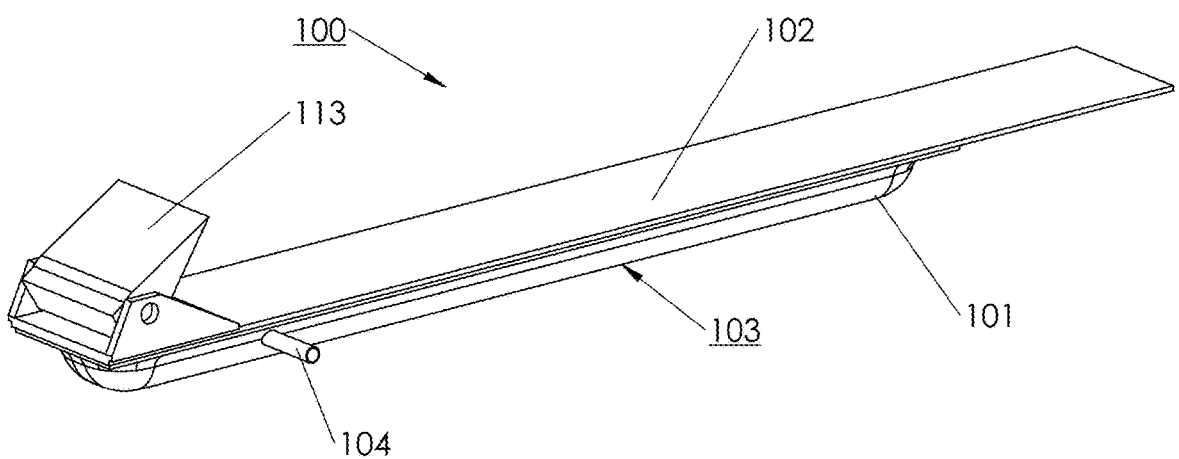
FIG. 1G—shows an inflatable belt design similar to FIG. 1A-1 wherein the belt fastening means is a cam-lock style system.

Alternate Embodiment #8. FIG. 1G shows a variation of the inflatable belt 100 of FIG. 1F where instead of a ratchet style mechanism 112, a cam-lock style mechanism 113 is provided. All such details about location, placement, material, operation etc. commented regarding FIG. 1G apply to FIG. 1F. The main difference is that there are no tooth embossments, or similar, features required for the cam-lock to function. The outer belt material 102 may simply be extended beyond the gas bladder 103, to a length sufficient as to wrap around a desired limb girth and push through the cam-lock style mechanism 113. The user may then simply pull the desired length through the cam-lock style mechanism 113 and activate the lock to hold the position of the outer belt fabric 102.

Similar concepts described in relation to the ratchet style mechanism 112, and how to lock the inflatable belt 100 in a loop-like shape, how to incorporate a belt spring 114, and how to use the ratchet style mechanism 112 as a handle for applying initial tension, similarly apply to the cam-lock style mechanism 113 of FIG. 1G.

Figure 1H:
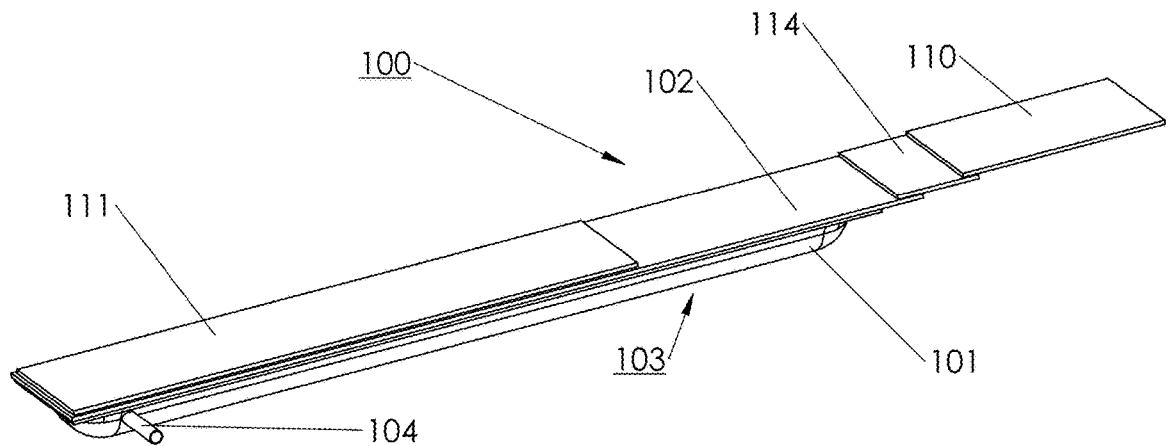
FIG. 1H—shows an inflatable belt design similar to FIG. 1A-1, further comprising a belt spring to add additional elasticity in the longitudinal direction for added comfort, safety, and assistance in keeping a constant pressure under muscle contraction.
Figure 1I:
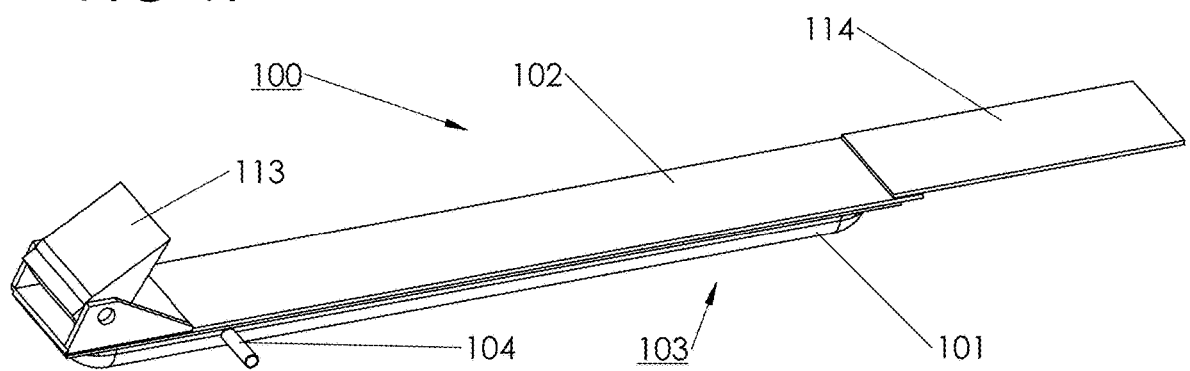
FIG. 1I—shows an inflatable belt design similar to FIG. 1G, further comprising a spring element, which is secured by the cam-lock style mechanism.
Figure 1J:
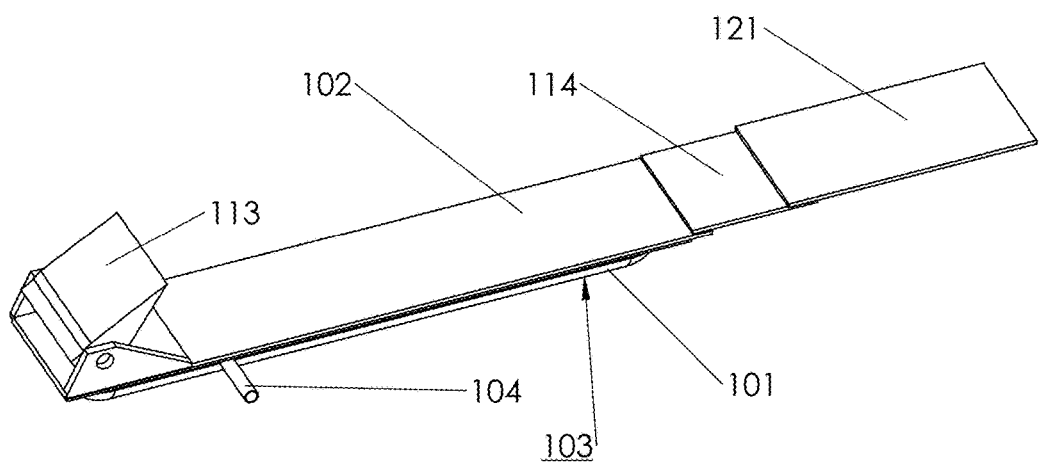
FIG. 1J—shows an inflatable belt design similar to FIG. 1I, but with an additional belt tension strap which connects to the belt spring and is secured into the cam-lock.

Alternate Embodiment #9. FIGS. 1 H, I, J shows an inflatable belt 100 similar to FIG. 1A-1, further comprising an optional component, a belt spring 114 to add additional elasticity in the longitudinal, or circumferential when placed around a body segment, direction for added comfort, safety, and assistance in keeping a constant pressure under muscle contraction. The belt spring 114 may be any elastic material that provides a suitable spring constant, such as, but not limited to, stretch webbing, stretch fabric, rubber, etc. The belt spring 114 may further be of any suitable width, length, or profile as to accomplish the goals set forth above and in the other embodiments described herein. For example the belt spring 114 may be the width of the outer belt material 102 or may be narrower or wider then that outer belt material, and have a rectangular shape, or a non-rectangular shape. The belt spring 114 may be attached to the outer belt material 102 at one end as shown, or anywhere along the length of the outer belt material, or may be placed between the cam-lock style mechanism 113 of FIG. 1G, or ratchet style mechanism 112 of FIG. 1H, and the outer belt material. The belt spring 114 may be of a short length as shown in FIG. 1H, for example 1 inch, or may be a longer length as shown in FIG. 1I. The belt spring 114 may be attached to an additional component, for example a first attachment means 110 as shown in FIG. 1H, or a belt tensioning strap 121 as shown in FIG. 1J. The belt spring 114 may be itself the belt fastening means 105 as shown in FIG. 1I where it is depicted in combination with the cam-lock style mechanism 113 of FIG. 1G. Additionally, combining FIGS. 1 H,1, the belt spring 114 and first fastening member 110 may be combined into an elastic first fastening member 110 such that a configuration similar to FIG. 1I is constructed but with a second fastening means 111 employed along an outer surface of the outer belt material 102 instead of the cam-lock style mechanism 113.

The belt spring 114 may similarly be applied in designs of a fold-back configuration such as shown in FIG. 1K and described in the preferred embodiment. In such cases the belt spring 114 may be attached to a loop coupler 115 that serves as the fold back mechanism. Or the belt spring 114 may be similar to as shown in FIGS. 1 H, I, J and the outer belt fabric 102 connected to the loop coupler 115.

The belt spring 114 functions as follows. As the user dons the inflatable belt 100, the belt spring is under very little tension and is in a substantially contracted state. As gas, or more specifically air, is pumped into the gas bladder 103 by the inflation means 106, the gas bladder begins to inflate and take up the space between the user's limb and the outer belt material 102. During this process, the belt spring 114 tension is increased and it starts to stretch, but only mildly so as most of the compliance is taken up by the air compressing in the gas bladder 103. When the target inflation pressure is reached, there is an equilibrium achieved in the tension in the belt spring 114 and the compression of the air in the gas bladder 103, combining to provide an overall compression on the user's limb. The belt spring 114, cam-lock style mechanism 113, ratchet style mechanism 112, or loop coupler 115 are ideally located away from the deep venous target area, which on the arms is the outer medial surface of the arm, and similarly the outer medial surface on the leg. These locations are relatively flat, have only superficial veins that can be compressed by the non-gas bladder portion of the band, and do not experience much bulging or movement to impede or abrade during muscle contraction. As the muscle contracts, volume inside the gas bladder 103 first begins to compress, causing a mild spike in the pressure according to arm girth, and volume of the air bladder. As the pressure increases, the higher pressure pushes outward on the outer belt material 102 in the radial direction and cause an increase in circumferential tension in the inflatable belt 100. This tension is taken up by the belt spring 114 and the belt spring expands slightly more to accommodate the now larger muscle bulge and keep the tension from further increasing and subsequently putting more compressive force directly on the underlying muscle. As the muscle is contracted, the system restores the previous equilibrium as the belt spring 114 shrinks back down in length and the bladder expands as the muscle reduces in size. Therefore the belt spring 114 serves as a further limiter to ensure that too-high pressures inside the gas bladder 103 are not allowed to occur, thereby improving both safety and comfort.

The reader may therefore note again that the exact location of the belt spring 114 in the construction of the inflatable belt 100 is not critical; what is critical is that the belt spring provides additional compliance during inflation and muscle contraction.

Alternate Embodiment—#10. FIG. 1L shows images of an inflatable belt 100 or a fold-back configuration, similar to FIG. 1K, from an experiment where the inner belt material 101 was pre-stretched by 20% as shown on the lower image. The reader may note there is significantly less kinking in the design with pre-stretch, eliminating the discomfort issue of the kinks pinching the user's skin. Pre-stretch of the inner belt material 101 may therefore be used to improve the comfort situation for the user. Additionally, pre-stretch cause the belt to curl into a spiral when not applied to the limb, and thus when applied, forms a natural "wrapping" of the limb which may help hold the location of the inflatable belt 100 on the limb. While the elimination of kinks via the pre-stretching technique is beneficial and may reduce the need for the body interface component 200, the reader may note that the body interface component provides many other functions such as spacing of the air bladder off the skin to allow sufficient inflation, anti-rotation gripping, and potentially used to guide in setting initial tension, therefore the reader shall understand there are still may benefits to the body interfacing component.

Figure 2E:
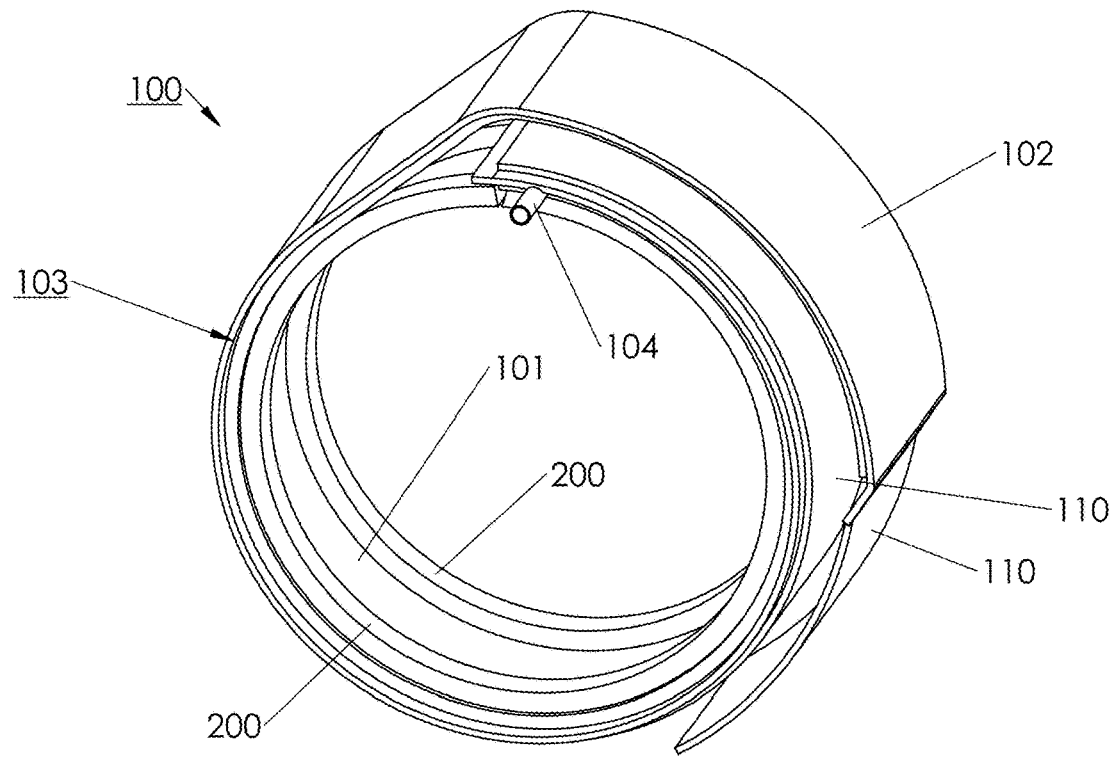
FIG. 2E—shows a variation of the configuration of FIG. 2D where two such body interfacing components are used on either edge of the inflatable belt, instead of a single body interfacing component that spans the full width of the belt.

Alternate Embodiment—#11. FIGS. 2A-E show the body interfacing component 200 as a detachable component. The body interfacing component 200 has been discussed extensively prior, and the reader shall remember it may be separable from the inflatable belt 100, attached at any point along the inflatable belt, not attached at all to the inflatable belt, at a width greater then, less than, or equal to the gas bladder 103, at a length greater than, less than, or equal to the gas bladder, made of any material that has appropriate properties to satisfy at least one of the described benefits, may or may not be used to guide the initial tensioning of the band, and may be employed in one or more instances to the inflatable belt. FIGS. 2D,E show configurations of the body interfacing component 200 as a single piece and as two pieces respectively. In both cases a friction surface 201 is facing inward against the user's limb. In FIG. 2D, the body interfacing component 200 spans the width of the gas bladder, has a length less than the gas bladder, and is attached along the edges of the outer belt material 102, via hook and loop fasteners as shown by first attachment means 110 and second attachment means 111. In FIG. 2E, the body interfacing component 200 is attached only along the edges of the inflatable belt 100, and attached similarly to the user as in FIG. 2D.

The reader shall note these are but two examples of how a body interfacing component 200 can be used, and all such further derived or combined configurations may be considered within the scope of this invention.

Figure 3A:
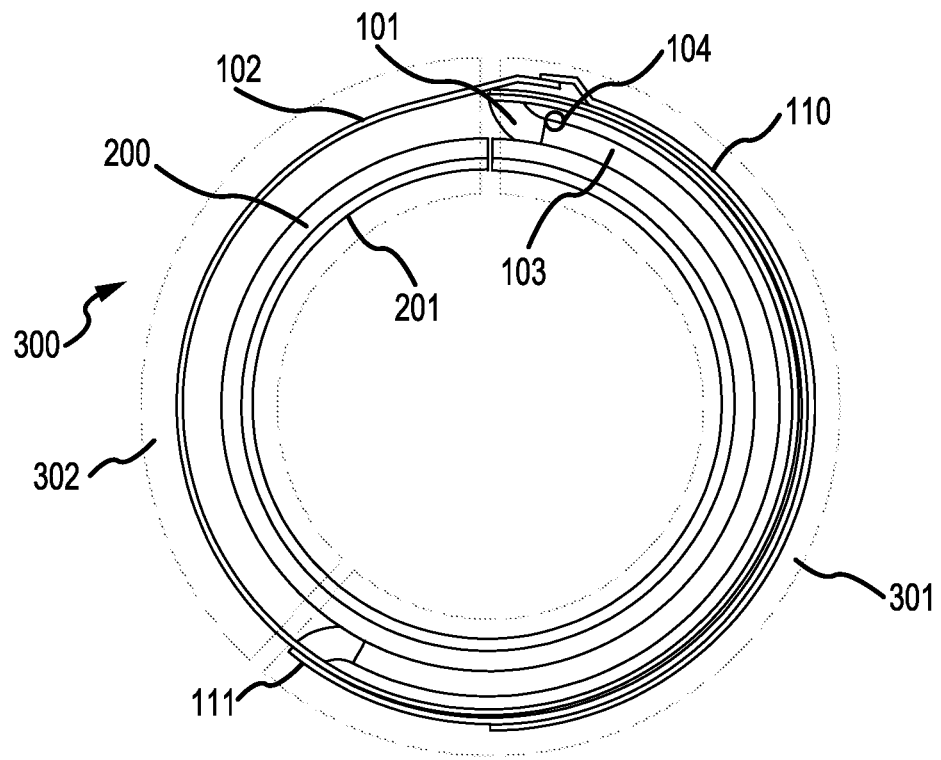
FIG. 3A—shows an example of a variation of the inflatable belt of FIG. 1A-1 wherein the inner belt material is substantially shorter than the outer belt material and the gas bladder covers only a portion of the circumference of the limb, targeting the zone required to optimally compress the veins.

Alternate Embodiment—#12. FIG. 3A shows a targeting inflatable belt 300, comprising a gas bladder 103 that divides the circumference of the limb (not shown) into a target compression zone 301 under the gas bladder, and a target compression relief zone 302 that is not under the gas bladder. The target compression zone 301 is ideally at least 30% of the full circumference and placed over a portion of the limb where the deep venous system may optimally be accessed and compressed as shown in FIG. 10, 11. The length of the gas bladder 103 in such a configuration may therefore be the girth of the smallest limb that is desired to be compressed, thereby covering 100% of that person, and covering up to 30% of the girth of a user who has a limb girth of 333% of the smaller limb girth, giving a substantial range of limb girths. The targeting inflatable belt 300 of FIG. 3A is applied in a circumferential position to the limb such that there is optimal coverage of the compression target zone 301 over the deep veins, in order that the tissue compressed during inflation, displaces radially inward, and cause compression of the deep veins. On the arms, this is position is on the inner medial surface and on the legs, this position is on the inner medial surface in the groin region, slightly rotated toward the thigh as shown in FIGS. 10, 11. The compression relief zone 302 is preferably located over the outer medial surface of the arm and on the outer medial surface and over the hip flexor muscle on the legs. By creating a relief space in these areas, the muscles that move perpendicular to, and underneath, the inflatable belt 100, in particular the hip flexor muscle during raising of the knee in running or "high knee" exercises, avoid a hard, pointed, compression feeling from the gas bladder 103, which can get quite rigid when inflated with substantial air, or used with belts of sufficient rigidity as in the case of Sato's inventions that employ stiffeners. Thus, overall comfort is improved while maintaining the effective levels of BFR.

The reader may note that while the targeting inflatable belt 300 is shown in a straight overlap configuration, the same concepts can be easily adapted to a fold-back style configuration.

Figure 3B:
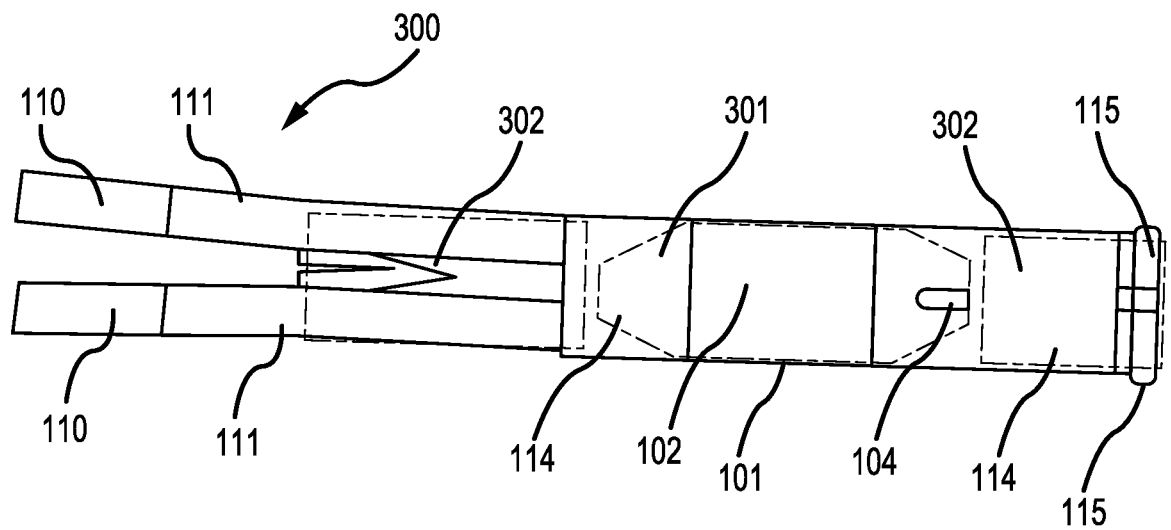
FIG. 3B—shows an example of a non-rectangular gas bladder, designed for the legs, for optimizing the comfort for the user by only compressing a target compression zone, while simultaneously providing sufficient compression to achieved adequate BFR.

Alternate Embodiment—#13. FIG. 3B is another example of a targeting inflatable belt 300, designed specifically for the leg. This version was designed and tested to demonstrate a couple key aspects of the physics of what is happening with the compression levels. It has been previously discussed that wider bands require less pressures to cause a given level of venous restriction, and it has been reported that user's wearing blood pressure cuffs report higher levels of comfort than with KAATSU equipment, which is narrow. What is known is that blood pressure cuffs are much wider, but also use much lower pressures than KAATSU equipment because of the previous effect discussed of cuff width on tissue displacement and degree of restriction. However, the applicant has tried a blood pressure cuff, and while the static comfort may be higher, the wide cuff compresses so much muscle, is totally inelastic, and therefore the muscle has nowhere to go and to try a movement, like running, is impossible. The applicant therefore has invented a concept of a wider targeting inflatable belt 300 with a gas-filled, non-rectangular, gas bladder 103, over non-rectangular compression target zone 301, shown by the diamond shaped profile in FIG. 3B, and compression relief zones 302 on either side of the target compression zone. The target compression zone 301 under the gas bladder 103 is meant to cover the inner groin area of the leg at the widest part, and tapers down to a thinner width as the targeting inflatable belt 300 is wrapped around the leg. The target compression zone 301, ends prior to overlapping the hip flexor muscle which resides underneath the compression relief zone 302. Hook and loop fasteners are employed as first fastening means 110 and second fastening means 111 respectively in a fold-back style for application to the user's leg. Because of the contour of the leg is in some cases conical, dual fastening means may be used, so that that they may separate and contour better to the conical surface of the leg than a single fastening means which would apply uneven tension and be loose on the bottom edge where the leg circumference is less. Spring elements 114, in the form of stretch fabric, are employed between the loop couplers 115 on one side and the second fastening means 111 on the opposite side.

This extension of the concept of a targeting inflation belt 300 illustrates yet another of the many configurations, combinations, and quantities of concepts and design elements invented by the applicant in designing the optimally comfortable and effective solution for a BFR belt concept. As is such, all prior discussion and concepts of spring elements, fastening means, etc shall further apply to this embodiment for creating an optimal targeting inflation belt 300.

Figure 4:
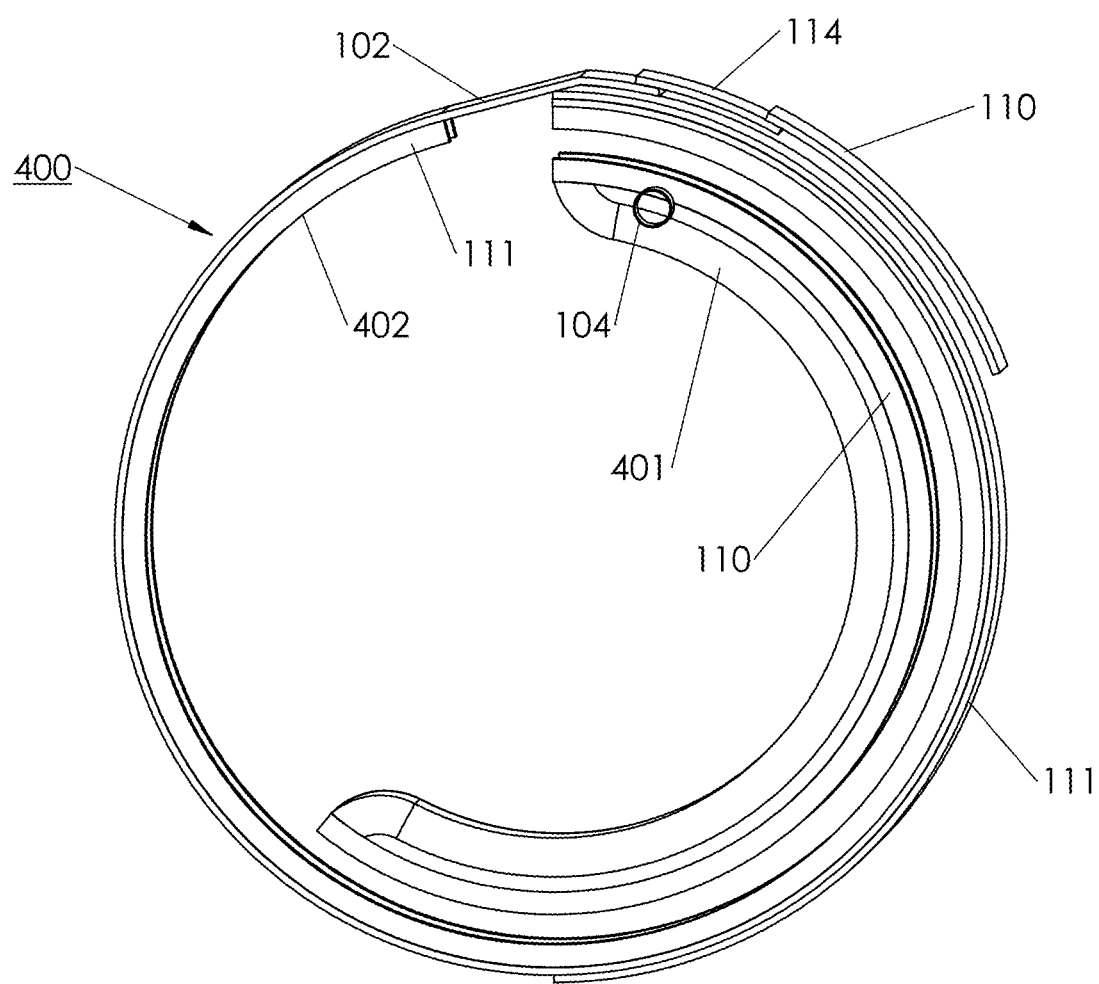
FIG. 4—shows an inflatable belt assembly wherein a gas bladder is removable from an outer belt material via fastening means, to allow for cleaning of the gas bladder, or quick attachment of bladders of appropriate lengths for users of different limb girths.

Alternate Embodiment—#14. FIG. 4 shows a modular inflatable bladder 400 comprising a detachable gas bladder 401 for attachment to an outer belt material 102. Detachable gas bladder 401 may be made of any suitable, elastic, airtight material such as those described herein. Detachable gas bladder 401 is in communication with an input port 104, and the input port may be a molded in feature in the case of a molded urethane or latex bladder, or may be a separate piece that is inserted. The detachable gas bladder 401 further may be in communication with a first attachment means 110 with which the user may attach the detachable gas bladder to a second attachment means 111 on the outer belt material 102. The outer belt material 102 further is in communication with another first attachment means 110 and another second attachment means 111 which are used to lock the outer circumference of the modular inflatable belt 400 as described in prior embodiments. In FIG. 4, the attachment means, or belt fastening means 105 are meant to be hook and loop fasteners but any such fastening methods as previously described may be used if they accomplish the same objectives. An optional spring element 114 is further shown to add a degree of circumferential elasticity as previously described as being beneficial, or the outer belt material 102 may be slightly elastic to allow for slight circumferential stretch as previously described as being beneficial.

Operation of this embodiment is substantially the same as previously described, only the step of adding an appropriately sized detachable gas bladder 401 to the outer belt material 102 is required prior to application to the user's limb. The benefit of detachable gas bladders 401 is that an individual can have and retain their own bladders for washing or cleaning and sanitation is thus improved which can be important in a medical application for example. Further, if the detachable gas bladder 401 is a simple construction, such as RF welding two strips of stretch fabric with Velcro strips together, many sizes can be fabricated in mass production very easily and thus a simple, customized solution is easily reached. The body interfacing component 200 is not shown, but may be added to the detachable gas bladder 401 permanently, detachable in its own right, or not used at all. All the prior discussions regarding the body interfacing component 200 and benefits thereof, still apply to this embodiment. Finally, the reader may not that while a straight overlap configuration is exemplified, the features, components, and quantity may all be adapted to create a fold-back style of belt.

Figure 5:
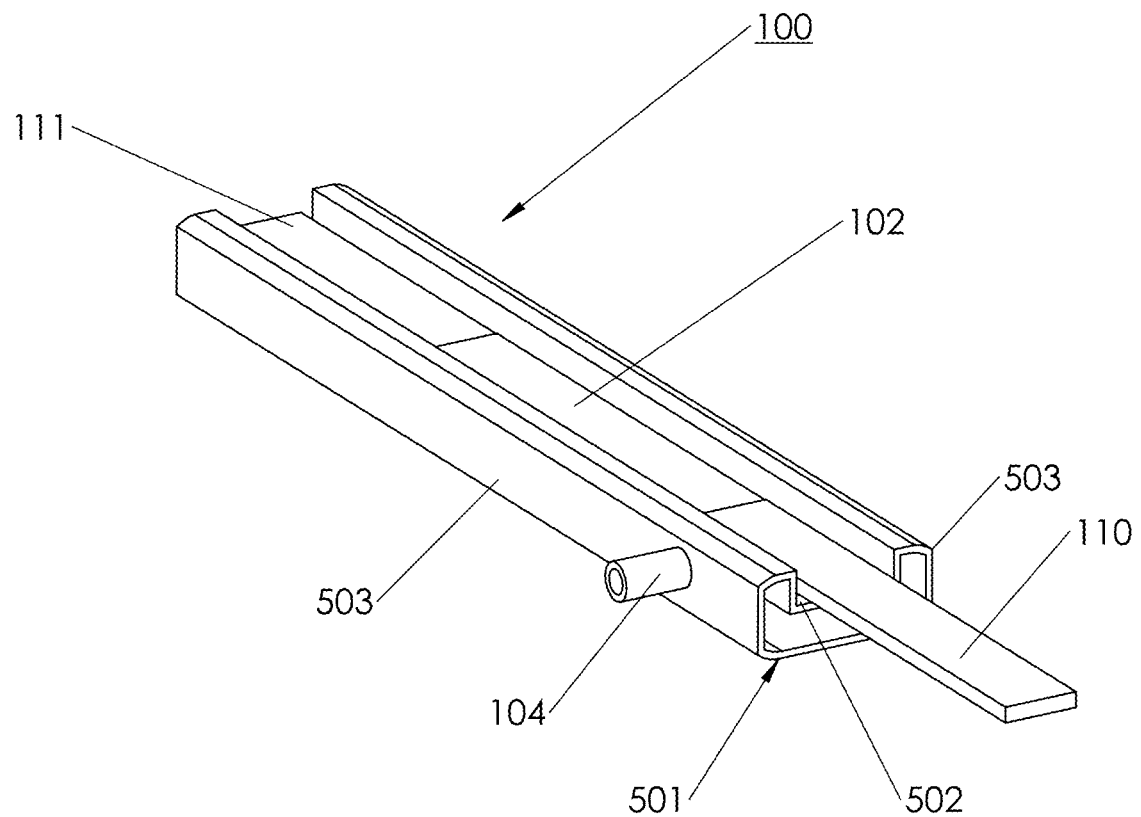
FIG. 5—shows an inflatable belt assembly comprised of a molded elastic bladder, an outer belt material, and anti-roll profile and features.
Figure 6:
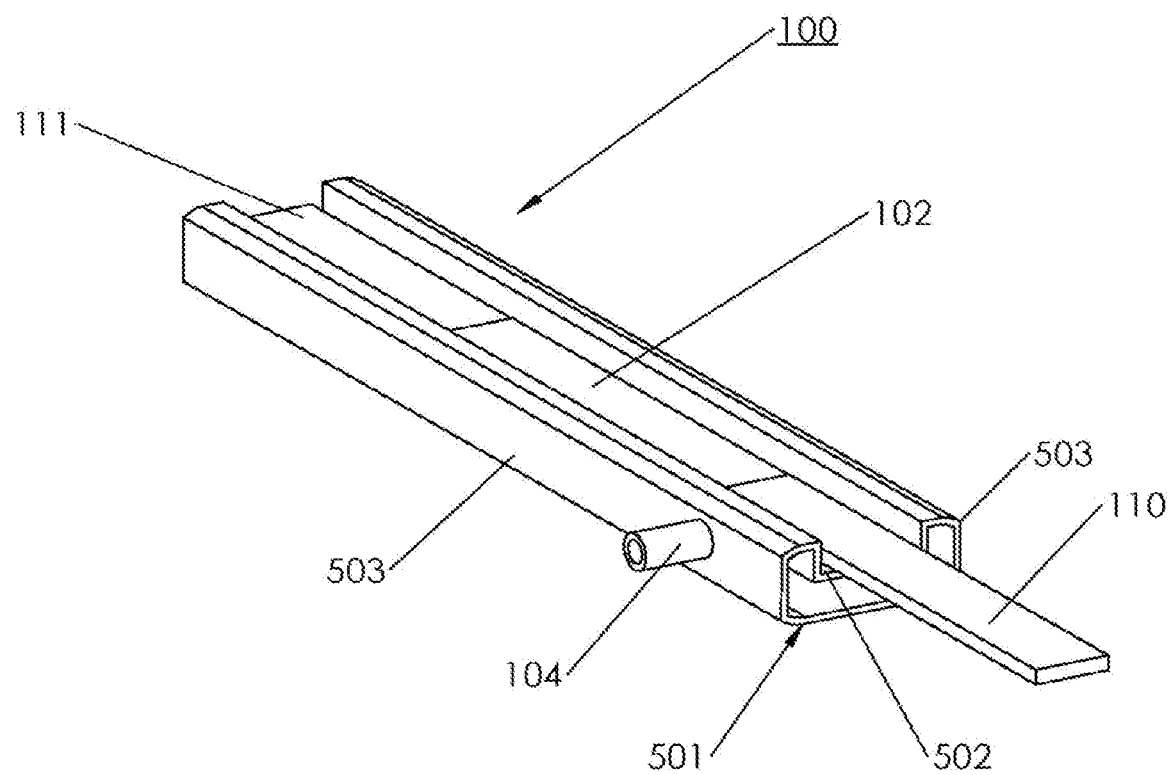
FIG. 6—shows an inflatable belt assembly comprised of a molded elastic bladder, an outer belt material, and anti-roll profile and features.

Alternate Embodiment—#16. FIG. 5 and FIG. 6 show an alternate construction of an inflatable belt 100, comprised of an inner molded bladder 501, an input port 104 in communication with the inner molded bladder, an outer bladder surface 502, an outer belt material 102 in communication with the outer bladder surface, and a first fastening means 110 and a second fastening means 111, and the inner molded bladder comprises additional anti roll features 503 on either side that prevent the inflatable belt from moving on the user's limb during inflation, muscle contraction, and exercise. The inflatable belt 100 of FIG. 5 is shown without end caps for illustration purposes only to show that it is hollow, but the readers may recognize the that inner molded bladder 501 is in fact hermetically sealed on the ends as well so that it is capable of holding a gas pressure. The inner molded bladder 501 may be made out of latex rubber, polyurethane, or another other such elastic material. The thickness of the walls may be equal, or, for example, the thickness of the wall in contact with the user may be thinned such that it has less resistance to inflation and biased to inflate radially inward to compress a body segment. The reader may recognize there are many variations of material type, material properties, and construction properties, such as wall thickness, that may provide certain advantages, and as long as the inner molded bladder 501 is configured to resist movement on the limb, and apply an adequate compression force against the limb under inflation and when restrained, all such variations may be considered within the scope of this invention.

The input port 104 is substantially the same as what has been described previously, but may be molded in, and therefore integrated together with the inner molded bladder 501 forming an integrally formed component. The length of the inner molded bladder 501 may be substantially similar to the bladders previously discussed and may cover only a portion of the target limb, the full circumference, or even overlap itself as shown in previous embodiments of an inflatable belt 100. The width of the inner molded bladder may be substantially similar to that previous discussed, or discussed in Sato's patents, but may also be wider or narrower depending on the target limb size. The outer belt material 102 is in contact with the outer bladder surface 502 of the inner molded bladder 501 as shown in FIG. 5 and may cover the full length of the outer bladder surface, be longer than the outer bladder surface, or only a portion thereof. For example, the outer belt material 102 may not cover a portion of the outer bladder surface 502 such that the inner molded bladder 501, which is elastic material, may stretch along this length. In such a construction, the inner molded bladder may act as the belt spring 114 described previously to assist in keeping pressure constant during muscle contraction. In such a case, the second fastening means 111 may be attached to the outer bladder surface 502 directly, for example via bonding, such that when the inner molded bladder is wrapped around a user's limb, the first fastening means 110 connects with the second fastening means 111 to lock the circumference of the inflatable belt 100. Additionally the outer belt material 102 may not be used at all and both fastening means attached directly to the outer bladder surface 502 by suitable means with an optional gap between the ends and along the length of the outer bladder surface to allow the inner molded bladder 501 to stretch. The inner molded bladder 501 may incorporate reinforcing components (not shown, but similar to FIGS. 6A-C) to assist it in keep its shape and prevent roll.

Additionally still, if one of the fastening members is elastic, no gap need exist and the other, non-elastic member may cover substantially the full length of the outer bladder surface 502. The inner molded bladder 501 may further incorporate anti-roll features 503 that resist the bladder from rolling or moving on the user's limb. The anti-roll features 503 are depicted in FIG. 5 as two cavities in the inner molded bladder 501 on either side of the fastening means and outer belt material 102.

When the inflatable belt 100 is placed around the user's body segment, for example the arm, with appropriate initial tension, and the inner molded bladder 501 is inflated, the large cavity will try to expand, invert, and form a sphere. The central portion, covered by the outer bladder surface 502 is kept from substantially expanding via the outer belt material 102 and fastening members, however employed, and the stress is shifted to the anti-roll features 503, which try and turn into small spheres on the ends. These anti-roll features 503 act as pontoons to keep the belt relatively stationary and located substantially in one place as the inner molded bladder moves over the underlying muscles during exercise. Many such profiles and shapes may be conceived that serve to prevent the belt from rolling across the muscles, and such profiles may be molded into the inner molded bladder 501 itself or affixed to it separately. The reader may recognize that the concept invented is a mechanism and method of restraining an inflatable belt 100, of inner molded bladder 501, from expanding radially outward, while simultaneously securing it to a body segment on the user and preventing it from rolling around on the user's limb during user movement.

Additionally, a belt spring 114 (not shown) may be added into the perimeter of the restraining mechanism, which in the case of FIG. 5 is the outer belt material 102 plus fastening members. Additionally still, a body interfacing component 200 (not shown) may be added to the assembly to improve the function based on the advantages of the body interfacing component as previously described. The reader may recognize that additions, or omissions, of these design elements further illustrate the applicant's statement that many combinations of such design elements exist and may be considered within the scope of this invention. The readers may further understand that by "prevent the inflatable belt from moving on the user's arm during inflation", the applicant understands and contemplates that the inflatable belt 100 may move slightly during user movement, but should return to substantially the same position when movement, i.e. muscle contraction, is ceased.

This invention has the benefits that it is simple, contains minimal components, and is cheap to construct and apply without any, or minimal sewing operations. Finally, the reader may not that while a straight overlap configuration is exemplified, the features, components, and quantity may all be adapted to create a fold-back style of belt.

Alternate Embodiment—#17. FIGS. 7A, B depict a pre-inflated belt 700 for use in BFR training. The pre-inflated belt 700 has a fixed volume of gas trapped inside the gas bladder 103, as shown in FIG. 7A, during the manufacturing process, with an optional input means 104, as shown in FIG. 7B, to refill the gas bladder or take a pressure reading of the pressure inside the gas bladder. Additionally, the pressure reading may come transmitted wirelessly or via wire, from an embedded pressure sensing means 902 (not shown), for visibility on a pressure readout 703 by the user. The gas bladder 103 may be formed by any of the concepts described herein, but is depicted by an outer belt material 102 connected with inner belt material 101 in a hermetically sealed fashion. Tensioning means 702, depicted here as a ratchet style, is further in communication with the outer belt material 102, or in the case of a molded, integrally formed belt, the molded component thereof. The tensioning means 702 may be configured such that the gas bladder 103 is capable of passing through the tensioning means, or the gas bladder may be short enough, as in the targeted inflatable belt 300, such that the minimum circumference is achieved when one end of the gas bladder contacts the other end during the tensioning process. An optional pressure readout 703, which may be detachable, may come fixed to the pre-inflated belt 700 or the pre-inflated belt may simply have notched markings or labeling means generally known in the art that illustrate to the user how to consistently reproduce a certain pressure condition from one time to the next. The notches or labeling means may correspond to a table, pre-calculated, and demonstrated, that links specific body segment girths with a specific notch or label, and predicts approximately a corresponding bladder pressure. In such manner, it may be possible to give guidance to a user on where to tension the belt without actually ever measuring the pressure inside. Such a configuration would prove beneficial in simplifying the process, providing consistency and reliability, and require no measurement or judgement process by the user. As will be discussed later, an automated system could be further simplified with a tensioning means such as a rack and pinion, stepper motor, or other accurate positioning system to measure length of the belt, and use pre-calculated knowledge given the limb circumference to infer the level of compression applied.

The use of the pre-inflated belt 700 is similar to prior embodiments except there is no need to attach an inflation means 106, and thus the overall system has fewer components, and is cheaper to make. In the case that notches or labels are provided, the user may tighten the pre-inflated belt to a specific notch or label position and may do so repeatedly or may increase or decrease the tension from time to time.

Alternate Embodiment—#18. FIG. 8A, B show two variations for a pressure relief valve combo 800. Various belt designs and systems have been described above, and the applicant has referred several times to the ability to combine various features and components to simplify the overall system and part count. FIG. 8A illustrates a combination of a manual relief mechanism 801 and an automated pressure relief mechanism 802, wherein the manual release mechanism is in-line with an air flow path 109. In FIG. 8A, the manual relief mechanism 801 comprises a manual relief plunger 804, trapped inside a pressure relief valve body 807, and in communication with a spring 803 (not shown) and o-ring 810. When no inflation means 106 (not shown) is attached, the spring 803 forces the manual relief plunger 804 against the pressure relief valve body 807 such that the o-ring 810 makes contact between the pressure relive valve body and the manual relief plunger to form an airtight seal and prevent backflow out the system. This mechanism is commonly employed in pressure relief systems and well understood in the field of pneumatic control. For the automated relief valve mechanism 802, an adjustable cap 806 is screwed up or down to compress a spring 803 (not shown), which in turn pushes a pressure relief plunger 805 to sandwich an o-ring 810 between the pressure relief plunger and the pressure relief valve body 807 to create an airtight seal. The screwing ability of the adjustable cap 806 gives the user flexibility to adjust the force that is holding the pressure relief plunger 805 against the pressure relief valve body 807 which is an important feature because typical check valves, or pressure relief valves have a tolerance of +/−20%, which is not acceptable for BFR training where a specific pressure limit is needed for safety and efficacy purposes. The automated pressure relief valve mechanism 802, may be considered analogous the pressure limiting valve 117 and, thus, herein disclosed is a mean for making the pressure limiting valve 117 adjustable. Two hose barbs 808 are provided. One hose barb 808 is provided on the side of the manual relief valve mechanism 801 for connection of a pressure inflation means 106 (not shown). This connection may have additional quick connect means such as valve coupling 120 (not shown), and the connection may further automatically compress the manual relief valve mechanism 801 when connected to allow air to enter into the system according to the airflow path 109 without an additional action by the user to open the manual relief valve. On the other hose barb 808, the input port 104 (not shown), or gas hose 119 (not shown) may be attached to accept air. Alternatively the belt valve 107 with quick connect style could be attached on this side as well in which case the quick connection should further incorporate a gas flow shutoff means 108. When the user has the system connected, air flows from the inflation means 106 into the opened manual relief valve mechanism 801, which is de-activated, and past the pressure relief mechanism 802, which is closed, and into the inflatable belt 100. When the pressure limit, according to the setting from the adjustable cap 806, is reached, the pressure in the system overcomes the spring 803 force associated with the pressure relief mechanism 802 and the pressure relief plunger 805 retracts, thus allowing air to escape until the air pressure drops below, or approximately below the limit, and the seal is restored, thus trapping a fixed, known pressure into the inflatable belt 100. The inflation means 106 is then disconnected, during which action the manual relief mechanism 802 is activated as the spring re-engages the manual relief plunger 804 against the pressure relief valve body 807, thus sealing the inlet and trapping the correct pressure inside. The manual relief plunger 804 is preferably exposed to the user such that they may depress it manually and relieve pressure from the belt at any time.

Figure 8B:
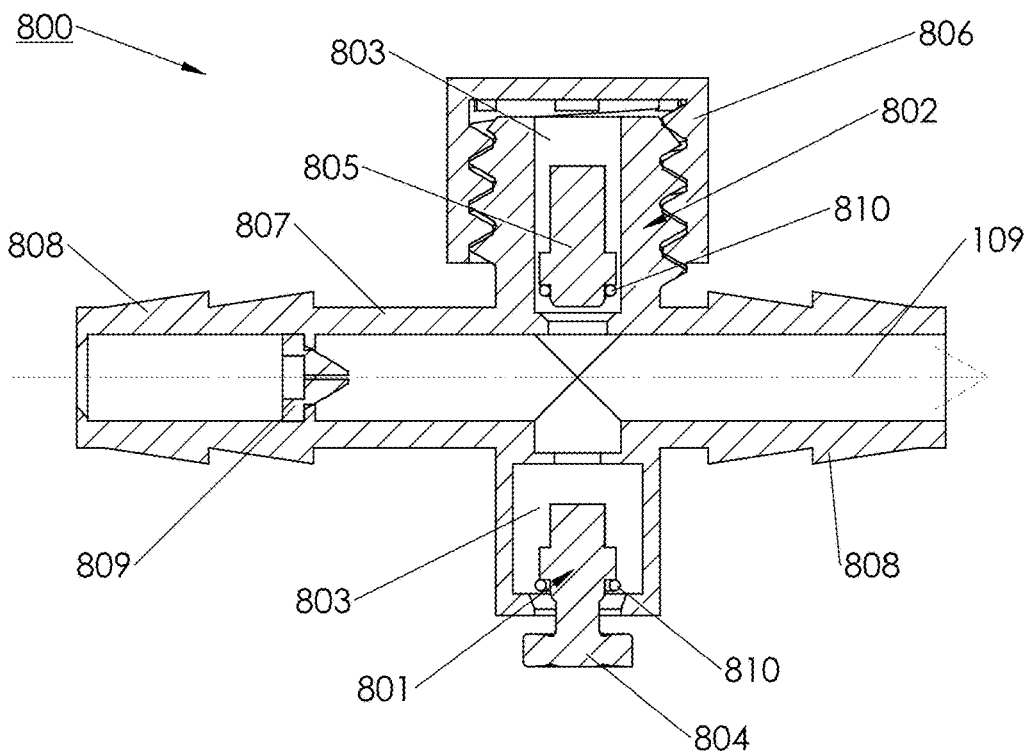
FIG. 8B—shows a pressure relief valve combo comprising a manual relief actuator perpendicular to an air flow, an adjustable pressure limiting valve to pre-set a predetermined pressure cutoff to limit the pressure in an inflatable belt, and a one-way valve for limiting return of a gas from a gas bladder in the inflatable belt, for use in BFR training.

FIG. 8B illustrates another configuration of FIG. 8A wherein the manual relief mechanism is removed from being in-line with the air flow path. To compensate, a one-way valve 809 in the form of a duckbill valve, is inserted into the inlet to allow air in, but not out. Otherwise, the various connection points and objects to the hose barbs 808, operation of the pressure relief mechanism 802 and manual relief mechanism 801 operate in substantially the same way as in relation to FIG. 8A.

The pressure relief valve combo 800 may be beneficial in combining various functions of valves discussed prior, and may be used in conjunction with, or instead of, the various valve configurations described prior. The pressure relief mechanism 802 may be configured to be separable from the rest of the pressure relief valve combo 800 to allow for replacement with pressure relief mechanisms with different maximum pressure settings. Such detachment, and replacement can provide a user with quick change maximum pressure settings without the complication of need a pressure readout to achieve a known, pre-determined pressure. This would reduce the bulk, cost, and complexity of the system and could provide for more accurate pressure setting as inexpensive pressure readouts can vary but +/−3% of full scale, and individual pressure relief mechanisms 802 could be individually calibrated more accurately. Various adjustments may further be made in such cases to the air flow paths, connection points, etc. without departing from the spirit of this invention.

Figure 9A:
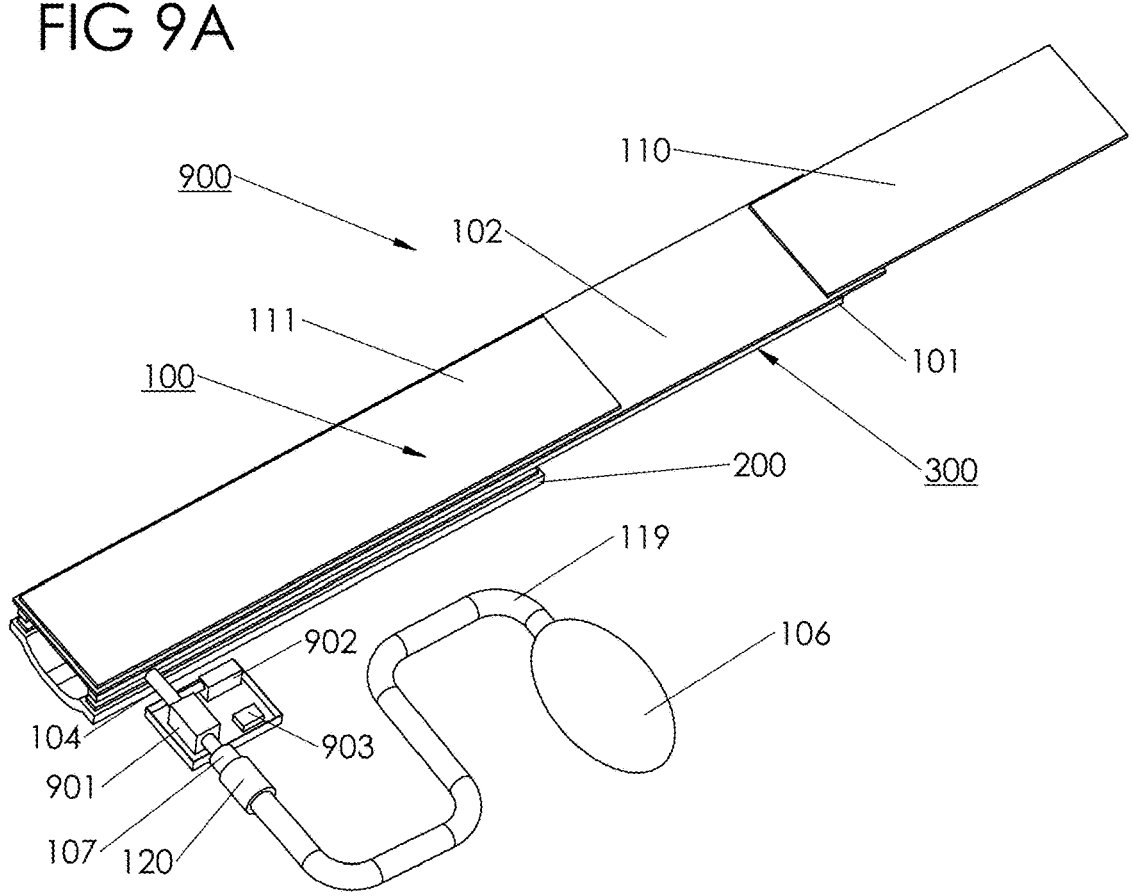
FIG. 9A—shows an electro mechanical blood flow restriction system comprising an inflatable belt as described in FIG. 2C, an electromechanical valve in communication with the input port to the belt, a pressure sensor also in communication with the input port of the belt, a microprocessor in communication with the pressure sensor, a belt valve for quick connection and disconnection of an air hose, an air hose, and a manual inflation means.

Alternate Embodiment—#19. FIGS. 9A-D represent a novel electromechanical blood flow restriction system 900 that incorporates an inflation means 106, which is manually actuated, together with an electromechanical pressure control system which is automated. FIGS. 9A, B show the belt design of FIG. 2C, but the reader may note this is but one example and the electromechanical blood flow restriction system 900 may incorporate any of the inflatable belt 100 designs discussed in this application or other designs or prior art, or variations thereof, such as targeting inflatable belt 300, as the means for applying a compression to a predetermined range on a user's limb. Similarly, a latex, or similar, squeeze ball and hose are attached as the inflation means 106, but any similar actuators as previously discussed may serve this function as well. Finally connection means to the belts or inflators may be considered covered by the myriad of examples previously listed on how to connect and provide proper valve control for belts and inflation means. Thus, this embodiment will focus on the electromechanical aspects, and interaction with the manually actuated inflation means 106.

It is important to first reiterate the distinct advantages of a manually actuated inflation means 106 versus an electromechanical inflation means. In particular, faster inflation times for a reasonably priced and sized package, cheaper overall cost, higher reliability, less noise, less weight, less battery usage and need for charging, causes the user to do a warmup which Sato states improves the effect and is a motion taught by KAATSU Training protocols, more readily available, and still others that may be apparent to the reader. The distinct advantages of an electromechanical inflation means is really only that the user doesn't need to do anything at all. However this could also present an unsafe scenario where, should a user for example pass out during BFR Training, and the training needs to be discontinued, the system will continue to function automatically and inflate/deflate cycle the belts. In the hybrid manual and automated system conceived herein, a user must themselves re-introduce pressure upon deflation, thus it is actually safer to eliminate the inflation aspect from automation, and restrict the automation to what pressure to maintain and how long to maintain that pressure for. Sato has described a number of cycling protocols in addition to the training protocols for how pressure should be varied over time, and the applicant may show that all such capabilities exist in the electromechanical blood flow restriction system 900 herein described and claimed, with the added distinct advantages of eliminating electrical inflation means as stated above.

The electromechanical control component of the electromechanical blood flow restriction system 900 shown in FIG. 9A, is comprised of an electromechanical valve 901 in communication with an input port 104 to the inflatable belt 100, the electromechanical valve further in communication with a belt valve 107 and a microprocessor 903 that is configured to control the electromechanical control valve based on a real time pressure data and a pressure target data. The belt valve 107 is further in communication with a valve coupling 120, which may be configured in a quick connect/disconnect fashion as previously described. However, whereas previously the belt valve 107 typically required a gas flow shutoff means 108 to trap a specific volume of gas in the gas bladder 103, the gas flow shutoff means in the configuration of FIG. 9A is not a required feature because the electromechanical valve 901 can serve this function of trapping air in the gas bladder. This is important because the gas flow shutoff means 108 is a more expensive option than the belt valve 107 that does not have this feature. A pressure sensing means 902 is in further communication with the input port 104 to sense a real time pressure measurement of the gas in the gas bladder 103, and relay this real time pressure data to the microprocessor 903 to properly control the electromechanical valve 901. The pressure sensing means may be a pressure transducer of any suitable kind that takes physical measure of a gas pressure and transduces it to an electrical signal, be it analog of digital. The reader shall note that a pressure limiting valve 117 could replace the need for a pressure sensing means 902 in terms of safety of not over-pressurizing the gas bladder 103. The microprocessor 903 may be any construction of integrated circuit such as FPGA, microcontroller, microprocessor, etc. The microprocessor 903 may be further configured to accept an input program, for example a cycling program as described by Sato, and execute the pressure limiting and timing attributes of such a protocol, or just the timing attributes in case a pressure limiting valve 117 is used to limit the pressure to a maximum value. The programming of such a protocol may be stored in memory, such as non-volatile RAM, (not shown), and any required supporting circuitry may similarly be provided. The programming may be done through a common connection port, such as USB (not shown), by connecting the electromechanical blood flow restriction system 900 to a PC, phone, or tablet, and downloading the program to the microprocessor's memory through this mechanism. Alternatively, a wireless communication means (not shown) may be provided such as wifi, Bluetooth classic, Bluetooth smart, etc. and the protocol may be programmed on the microprocessor 903 and stored in memory wirelessly. The microprocessor 903 may employ a basic control algorithm to compare actual real-time pressure data with a target value, and control the electromechanical valve 901 as a means to limit the pressure in the inflatable belt 100 to not more than a target pressure data, which is dictated by the program. Such a pressure control protocol may simply be a monitoring of the pressure, then opening of the valve until the pressure drops below the target pressure data, as in the process of FIG. 9C, or may employ more complicated means to achieve more accurate results. However the reader may note that BFR, or KAATSU Training need not be so precise that a few mmHg make a big difference in the outcome, for example if the actual pressure is 5 mm Hg less than the target pressure because the valve was opened a little too long, so as long as the pressure control protocol, and electromechanical blood flow restriction system 900 prevent the pressure from going higher than the pressure target data for an extended period, the system is deemed to be functioning safely and properly. User feedback (not shown) and user input means (not shown) may additionally be provided to make the user's experience more sensible and user friendly. For example LEDs may be used to indicate a status of the system, such as when the user should start pumping the inflation means 106 to refill the gas bladder 103, or an LCD maybe use to communicate instructions to the user. Buttons may be used similarly to take input from the user, such as a "START" command, or "PROCEED TO NEXT STAGE" command, or the input may alternatively be made with haptic actuators like accelerometers that sense taps or tilts to register commands. The reader may note that many such means of communicating with a handheld electronic device are well known in the art and any such methods may be used to communicate data to, and register commands and data from, the user.

Figure 9B:
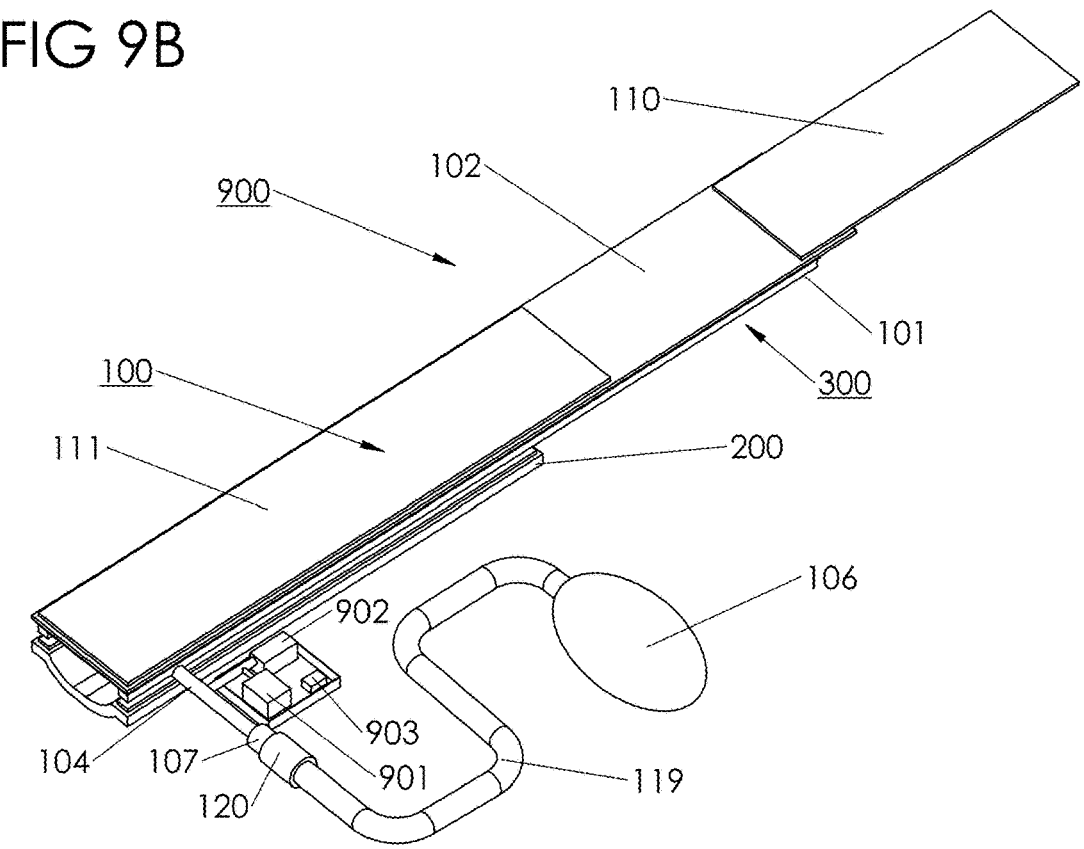
FIG. 9B—shows an electro mechanical blood flow restriction system similar to FIG. 9A, except the belt valve incorporates a gas flow shutoff means and is in communication with the input port instead of the air path going through the electromechanical valve.

FIG. 9B shows an alternate configuration of the electromechanical blood flow restriction system 900 wherein the location of the electromechanical valve 901 has been moved and the inflation means 106 is in direct communication with the belt valve 107. In such a configuration the belt valve 107 employs a gas flow shutoff means 108 to prevent the gas from leaking out of the gas bladder 103 when the valve coupling 120 is disconnected from the belt valve. FIG. 9B illustrates but one configuration, and as previously discussed there are many such variations possibly by swapping components around and all such configurations may be considered within the scope of this invention.

Figure 9C:
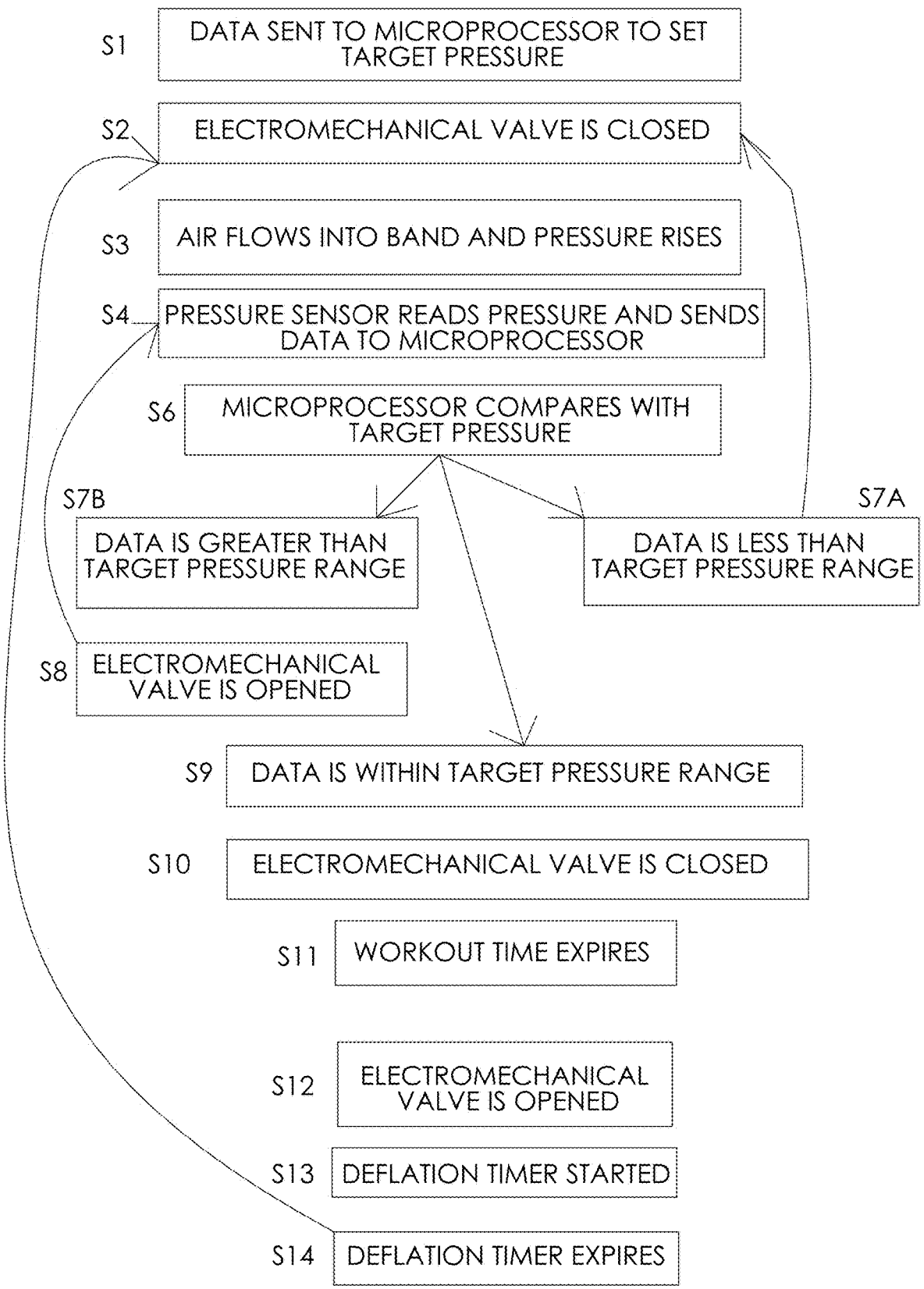
FIG. 9C—shows one example of a flow chart of data and programmed decision making around how to achieve a safe, accurate, programmable, pre-determined pressure limit in the blood flow restriction systems of FIGS. 9A, B, while requiring the user to do some minor work as a warmup exercise.

FIG. 9C illustrates a sample program for regulating pressure in the inflatable belt 100. Step 1 (S1) is that pressure target data is sent to the microprocessor 903 to set one or more pressure targets for the microprocessor. This step may apply to any point in the lifecycle of the microprocessor, whether it be pre-programmed data in the factory, or the day of the training session, programmed by the user. This may simply be a single pressure limit, which is a training pressure, or may be a series of pressure targets on timed intervals as described in FIG. 9D. Step 2 (S2) is that the electromechanical valve 901 is closed by the microprocessor 903. Alternatively the electromechanical valve 901 may be configured in a normally closed position, requiring electricity to open it, and this step therefore may be omitted. An optional starting input may be sent, or entered by the user, or the microprocessor may start the sequence automatically once turned on. The microprocessor 903 sits and waits, monitoring the real time pressure data from the pressure sensing means 902 at an appropriate rate, for example 10 Hz. The microprocessor 903 may optionally alert the user, for example with audio, vibration, or LED feedback to begin pumping on the manual inflation means 106. As air flows into the belt (S3) and the pressure rises the pressure sensing means 902 is constantly feeding real time pressure data to the microprocessor 903 (S4). Step 5 (S5) shows the microprocessor 903 compares each data point from the pressure sensing means 902 with the pressure target data that was programmed. From here the microprocessor 903 makes a decision based on the comparison output. If the real time pressure data is lower than the pressure target data (S7A), the microprocessor 903 maintains the electromechanical valve 901 closed, and waits for more air flow in, while continuously monitor and comparing the new data to the target (S2-S6) until the real time pressure data is higher than the target pressure data (S7B). After S7B, the microprocessor 903 optionally alerts the user that they can stop pumping, and opens the electromechanical valve 901 in S8. From here, the steps S4-S6 repeat, which is the monitoring cycle, until the real time pressure data is within a predetermined acceptable range from the target pressure data, Such a range may be for example +0/−10 mm Hg from the target pressure data for example. Once the real time pressure data is within the target range, the electromechanical valve 901 is closed S10 to maintain that pressure level inside the inflatable belt 100. If a workout timer is used, which is an added safety feature of the electromechanical blood flow restriction system 900, the workout time is started at this point as well. As FIG. 9A only illustrates a single pressure target, the system does not do anything further until the workout time (if set) expires in S11. At this point the electromechanical valve 901 is opened S12 and air is released from the inflatable belt 100. At this point the system may be turned off, however a few additional optional steps may provide a better experience for the user. At S12, the electromechanical valve 901 is left open and is in a similar state to just prior to S1, or after having been turned on for example when the valve is normally open configuration. The electromechanical valve 901 may remain open waiting for input from the user indicating they would like to start the training, or the microprocessor 903 may hold the electromechanical valve closed in preparation for a training session starting and sit at S3, constantly monitoring to look for appropriate pressures. Any configuration of sensory inputs and user feedback may be used to create nuances in the startup and termination procedure and the applicant makes it clear that he has contemplated all these variations. In the particular case of FIG. 9A, no user input means is assumed, and therefore the electromechanical blood flow restriction system must reset itself after each user, or power cycle to reside in a "waiting state" at S3. In terms of what happens after S11, a deflation time is then set S12 that waits for sufficient time to pass for all the air to be removed. At S13 the deflation time expires, and the microprocessor 903 assumes sufficient gas has been removed from the gas bladder 103 and returns to S2. The electromechanical valve 901 may be normally open or normally closed. The appropriate steps in 9A shall be modified, omitted, or added to provide the intended user experience as described, and it shall be clear to one skilled in the art of how to make these basic modifications.

FIG. 9D illustrates a cycle function capability similar to that described in Sato's patents, but carried out with the simple novel electromechanical blood flow restriction system 900. FIG. 9D illustrates how the same capabilities as a fully automated system can be provided with a hybrid manual/electromechanical system with all the advantages described above. In S1, a protocol is programmed into the microprocessor 903 or associated memory. If normally open configuration, the electromechanical valve 901 is closed by the microprocessor 903. If normally closed configuration this step may be omitted. FIG. 9D assumes various input and output mechanisms to illustrate these functions within the system, and thus at S3, the user is alerted to activate the inflation means 106 to start putting air into the inflatable belts 100 with the manual inflation means. Such alerts may be done with visual clues, audio clues, or haptic feedback to name but a few examples. S4 shows air entering the system from the user's actions. Intermediary steps between S4 and S5 have been omitted for clarity but the reader may understand that a similar process from FIG. 9C S4-S9 is repeated to cause the pressure to reach within a target range of the target pressure data in S5. Once the pressure target is reached, a pressurized stage timer is started S6, to monitor the time the pressure is to be maintained in the inflatable belt 100 according to the programmed cycle protocol. If this is the first stage, the protocol timer is also started to monitor the overall progress of the protocol and determine when to end the cycling functions. As the pressurization timer expires S7, the electromechanical valve 901 is opened S8 and a depressurization stage timer is started S9. When the de-pressurization time is expired, S2-S9 are repeated according to the programmed protocol until the protocol is finished and the protocol timer has expired S11. At this point the electromechanical valve 901 is opened to release air and optional preparations S12 & S13 are made to prepare for the next user. Alternatively the electromechanical valve 903 may be left open, for example in the case of a normally open valve, and an input means utilized to signal to the microprocessor 903 to close the valve and prepare the system for a new session.

The reader may hereby note that two examples of how an electromechanical blood flow restriction system 900 may operate have been described in detail, but there are many more ways in which the pressure may be controlled vs time in an effective manner, and no such deviations from the prescribed procedures may be deemed to depart from the scope of this invention.

Alternate Embodiment—#20. FIG. 10 shows a cross section of a human arm in the vicinity where the inflatable belt 100 should be placed. A target compression zone 301 is marked showing the approximate area that should be compressed to provide venous restriction. The reader can clearly see that the veins, and particularly the deep veins in the arm are concentrated to specific locations and therefore compression around the entire circumference is not necessary to restrict the superficial and deep venous system. In the image, the circumference to be compressed may be configured to represent approximately 30% of the total circumference at minimum (because the superficial Cephalic vein may be compressed by the non-inflatable portion of the belt, although the reader may also not that some restriction, and potentially adequate restriction to get some effect, may be achieved with even less coverage. As stated in relation to the target inflatable belt 300, whose principles can be extended to any of the belt designs or contemplated configurations thereof, compression of only a portion of the arm circumference may have the benefit of creating a simpler, less bulky belt design, and provide a more comfortable experience to the user, versus Sato's and Wosowski's designs. FIG. 10 shows the primary veins being directly on the inside of the arm, and a superficial vein slightly to the front medial side of the bicep. The reader may further note that the superficial veins may also be compressed by the belt spring, or other belt material that is not inflatable as the entire circumference is under some degree of radial compression.

FIG. 11 shows a target compression zone 301 for the leg in a cross sectional view of the body in the vicinity of where the inflatable belt 100 should be placed. Again the reader can see that the target compression zone 301 may be configured to represent approximately 30% of the total circumference, with the primary compression region being in the front interior side at roughly a 45 degree angle.

Alternate Embodiment—#21. FIG. 12 shows two examples of other ratchet style mechanisms 112. The first is a configuration similar to a zip tie, with a lever that may be rotated forward to disengage from the teeth 122 and release the ratchet. To tighten, the end of the mechanism with the teeth 122 is pulled through, and as each tooth passes the ratchet style mechanism 112 it is prevented from return via mechanical interference.

The second image is another form of ratchet style mechanism 112 in the form of a loop shape where two ends, of mating profiles are pushed and guided together by the inner tooth-like profiles. As each mating tooth 112 passes each other, the teeth click, and displace downward to fill the space directly above the mating profile, and thus mechanical interference in the circumferential direction is used to prevent the two ends from separating. To release, the two ends are slid laterally apart as there is no mechanical interference in that direction.

Both concepts for simply adjusting and locking a circumference of an inflatable belt 100 may be considered acceptable variations of the ratchet style mechanism 112, and could additionally serve to take the place of the outer belt material 102 in a configuration such as FIG. 4, or be used in constant connection with an inflatable bladder 103 that is adhered or connected via suitable means to the interior surface of these mechanisms. If the optional belt spring 114 is desired, at some point along the length of the belt, the belt spring may be inserted into the "tail" of these mechanisms between the tail and the gripping element to give the mechanisms some additional compliance.

Figure 13:
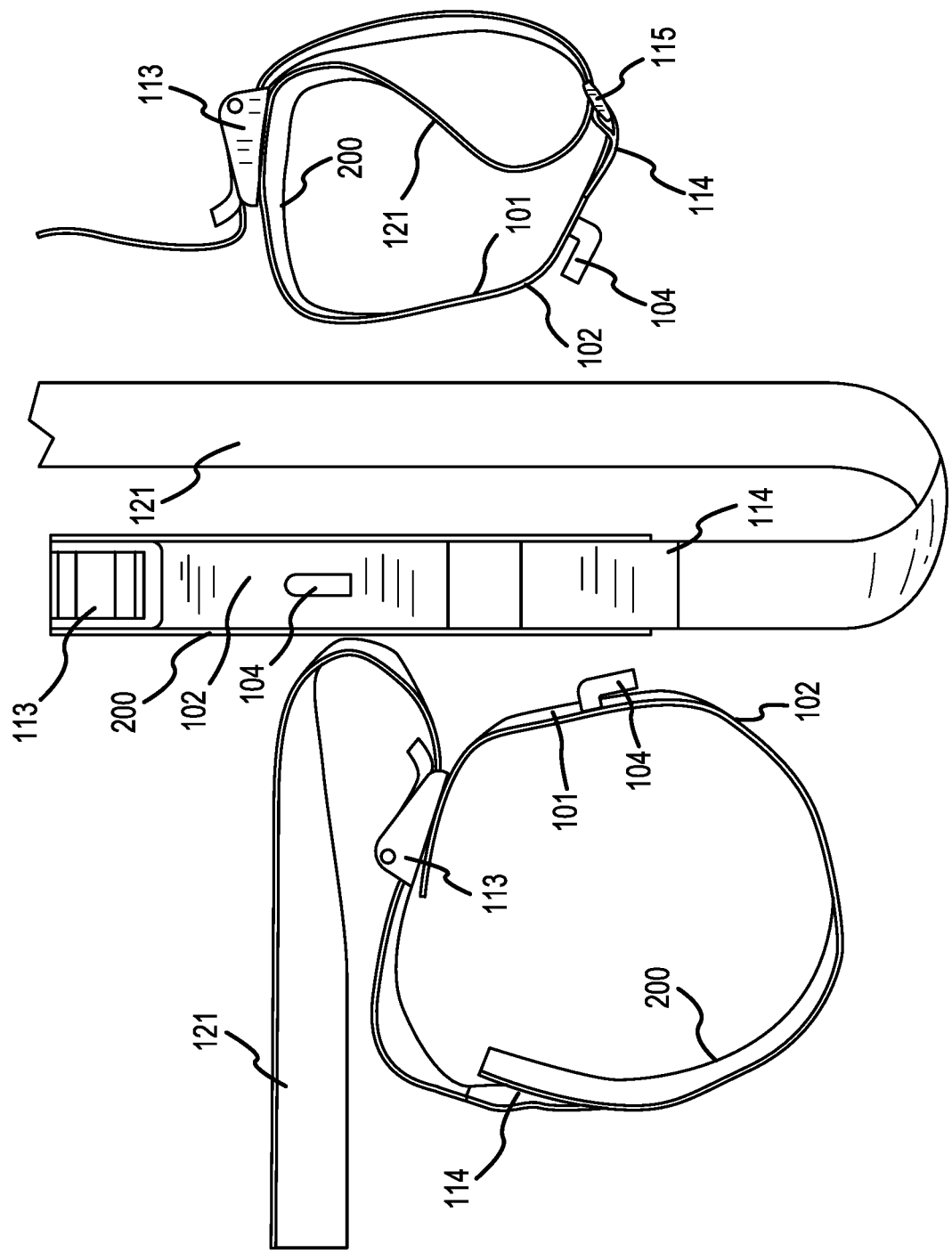
FIG. 13—shows three prototypes of inflatable belts that were constructed for testing; the left most is a cam-lock style with belt spring showing a belt tensioning strap, the middle belt is the same style but laid flat, and the right most belt is a cam-lock configuration in conjunction with a loop couple to double-back as a means of facilitating tightening of the belt.

Alternate Embodiment—#22. FIG. 13 shows a few physical prototypes of various inflatable belt 100 designs. The figure on the left is an actual prototype of FIG. 1J, with the addition of the body interface component 200. The middle image is the same inflatable belt 100 of FIG. 1J, with a body interface component 200 that is slightly wider than the outer belt material 102, and further serves to protect the user against the edge of the outer belt material. The belt tension strap 121 is sufficiently long that it may be grabbed by the arm where the inflatable belt 100 is applied to hold the position, while the user, with their opposite hand, uses the cam-lock style mechanism 113 as a handle, moves it in the direction opposite the belt tension strap to tighten down the inflatable belt.

The third image is an inflatable belt 100 with a belt tension strap 121 and cam lock mechanism 113, but with the addition of a loop coupler 115 attached to the belt spring 114, and the belt tension strap is fed through the loop coupler and then back through the cam lock mechanism. This configuration provides a small amount of pre-tension to the inflatable belt 100 and may further assist in reduction of rotation.

Alternate Embodiment—#23. FIG. 14A-E illustrate an adjustable distance measuring and positive locking system 1400 designed to make it prescriptive and straightforward for a novice to properly set the initial tension of a belt. Sato never addresses the initial tension in any of his applications related to inflatable belts, and this is a major oversight. KAATSU equipment does employ a mechanism for measuring initial tension but it is an iterative feedback loop process of setting, checking, and resetting, and therefore overly cumbersome and time consuming. Sato does discuss in U.S. Pat. No. 6,149,618 a tension measuring system, but this is in relation to operating tension, not initial tension, and is further susceptible to errors as the adjustments and hysteresis in the spring system Sato describes can cause significant differences in expected vs actual tension.

Figure 14A:
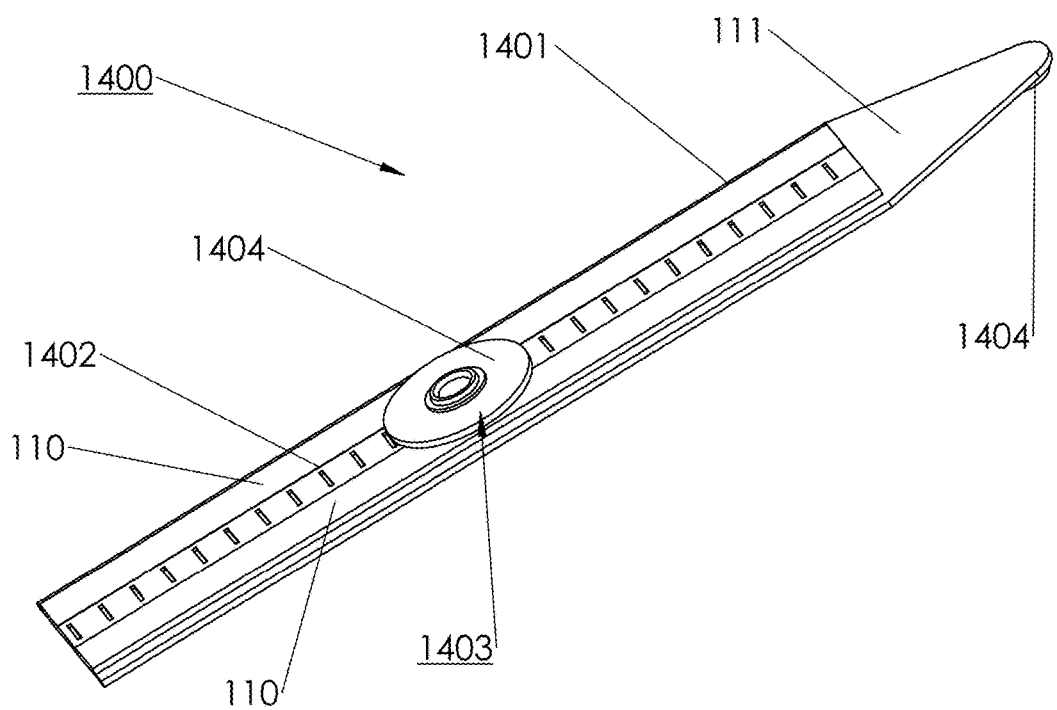
FIG. 14A—shows a non-inflatable belt that incorporates a prescription distance measuring and positive locking system for instructing a novice how to properly and precisely set the initial tension of the belt.

FIG. 14A shows a non-inflated belt 1401 similar to Sato's belt in U.S. Pat. No. 6,149,618, preferably made of some elastic material such as neoprene rubber. A first fastening means 110 is affixed to the outer surface of the non-inflatable belt 1401, at a point along the length of the belt as shown. The first fastening means 110 may cover the full length or only a portion thereof, and may start at one end, or somewhere other than at one end. An optional distance indicator 1402 may be screen printed, sewn on, or otherwise connected to the first fastening means 110, such that a scale is visibly formed on the non-inflated belt. Alternatively, the distance indicator 1402 may be a separate ruler or other devices that is not affixed in any way to the non-inflatable belt 1401. The distance indicator 1402 may incorporate markings that indicate a prescribed distance along the length for attachment of a positive locking means 112 that is in turn part of a positive lock adjustment 1403, which adheres to first fastening means 110 via second fastening means 111, also part of the positive lock adjustment. The positive lock adjustment 1403 may simply be made of a piece of hook fastener, with the hook side facing the loop fastener (i.e. first fastening means 110), and a positive locking means 112, such as a button snap, fixed to the hook fastener with the button snap facing upwards. The positive lock adjustment 1403 may be square, round, oblong, etc. and may incorporate markings that are obvious as to how to place against the distance indicator 1401 to achieve the desired setting. The positive locking means 112 is preferably a button snap, but may be any other such positive locking means such there is only one position at which the locking function may be achieved, and this precise location of the positive locking means is achieved. For example, it may be a hook, clip, or other mechanical type of interference where tolerances and dimensions are known and controllable. A mating component of the positive locking means 112 is placed on one end of the non-inflated belt 1401, such that when the belt is wrapped around the limb, the two components of the positive locking means are connected, and may be so connected in only one way, forming a known and predicable circumferential length of the non-inflatable belt.

To operate, the user follows the steps of FIG. 5E. The user first measures the girth of the limb to be compressed (S1). Then the user looks up on a table provided by the manufacturer, or equivalent instructor, the distance at which to place the positive lock adjustment 1403 along the distance indicator 1402 (S2). The user notes that distance on the distance indicator 1402 (S3) and attaches the positive lock adjustment 1403 thereon (S4), thus fixing the location of one end of the positive locking means 112. Then the user takes the non-inflatable belt 1401 and wraps it around the limb at the desired location (S5), and tightens until the mating end of the positive locking means 112 can reach the part on the positive lock adjustment 1403, and connects the two ends together (S6). In the case of snaps, this is simply snapping the two ends together to lock the initial circumference of the non-inflatable belt 1401.

The reader shall note that all such distance measuring and positive locking systems 1400 as described herein may be adapted to any of the inventions described in this application or the previously filed provisional application, and all such derivations and combinations shall be considered within the scope of this invention. Further the reader shall note that while a straight overlap style belt is described and depicted in FIG. 14A, a loop coupler 115 (not shown in FIG. 14A) may similarly be used to transform the configuration to a fold-back design as shown by Sato. An added benefit is that the user has a tactile, or "positive" feel to know that they have the band tensioned to the right amount and fastened in the right place. Often, depending on the limb girth, the attachment point is in a place that is not visible and so a generic scale as shown in Sato, without positive engagement, does not actually help the user. The applicant has solved this issue with the positive locking means 112. A further advantage of the positive locking means 112 is that it avoids the wear of hook and loop fastener over time. Sato, and indeed the applicant, advocate hook and loop fastener a simple mechanism for locking the circumference of the inflatable belt 100. However repeated application and removal of the hook component leads to fraying of the loop material. By using a positive locking means 112 that doesn't need to be removed, or only rarely so, the user doesn't impose this wear and tear on their product, and lifetime is improved, yet the infinite adjustability afforded by the hook and loop fastener is still maintained.

Figure 14B:
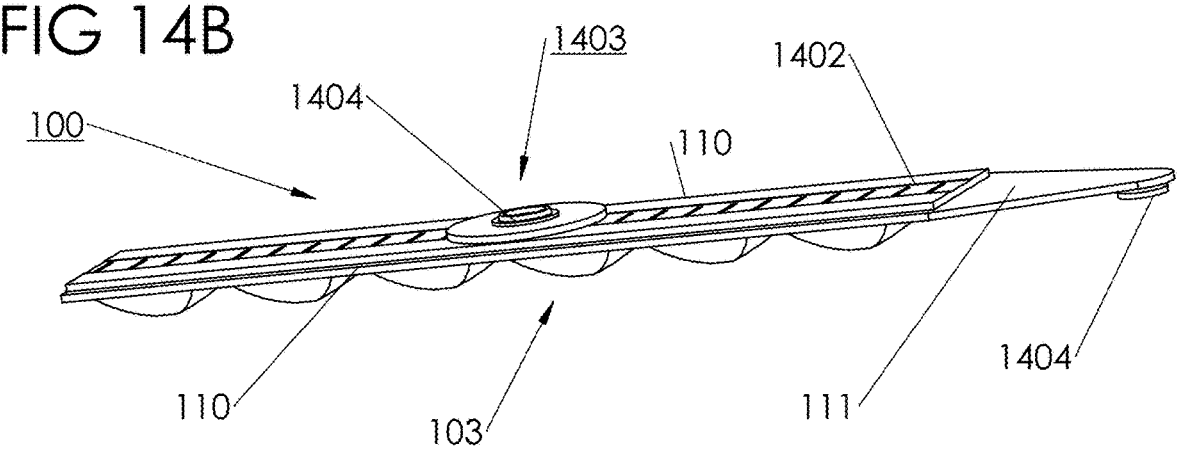
FIG. 14B—shows an inflatable belt with similar prescription distance measuring and positive locking system as FIG. 14A.

Alternate Embodiment—#24. FIG. 14B shows an adjustable distance measuring and positive locking system 1400 as adapted to an inflatable belt 100. The reader shall note the construction principles stated in the preferred embodiment and other embodiments related to inflatable belts 100 shall be combinable in a reasonable manner with modifications known to those skilled in the art, and all such combinations and variations need not be described further.

Figure 14C:
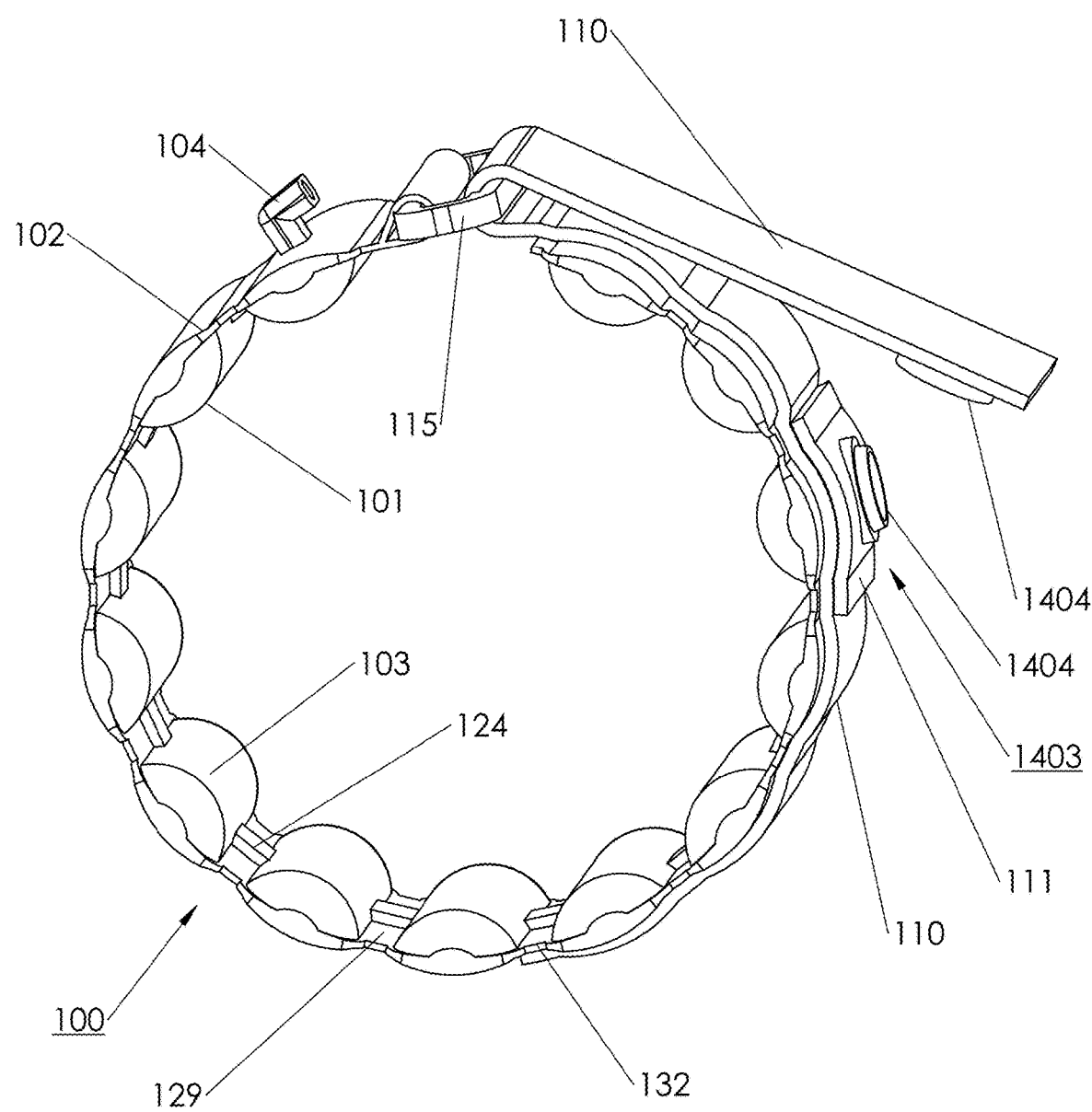
FIG. 14C—shows an inflatable belt in perspective view, combining properties and features with the distance measuring and positive locking means of FIG. 14A.
Figure 14D:
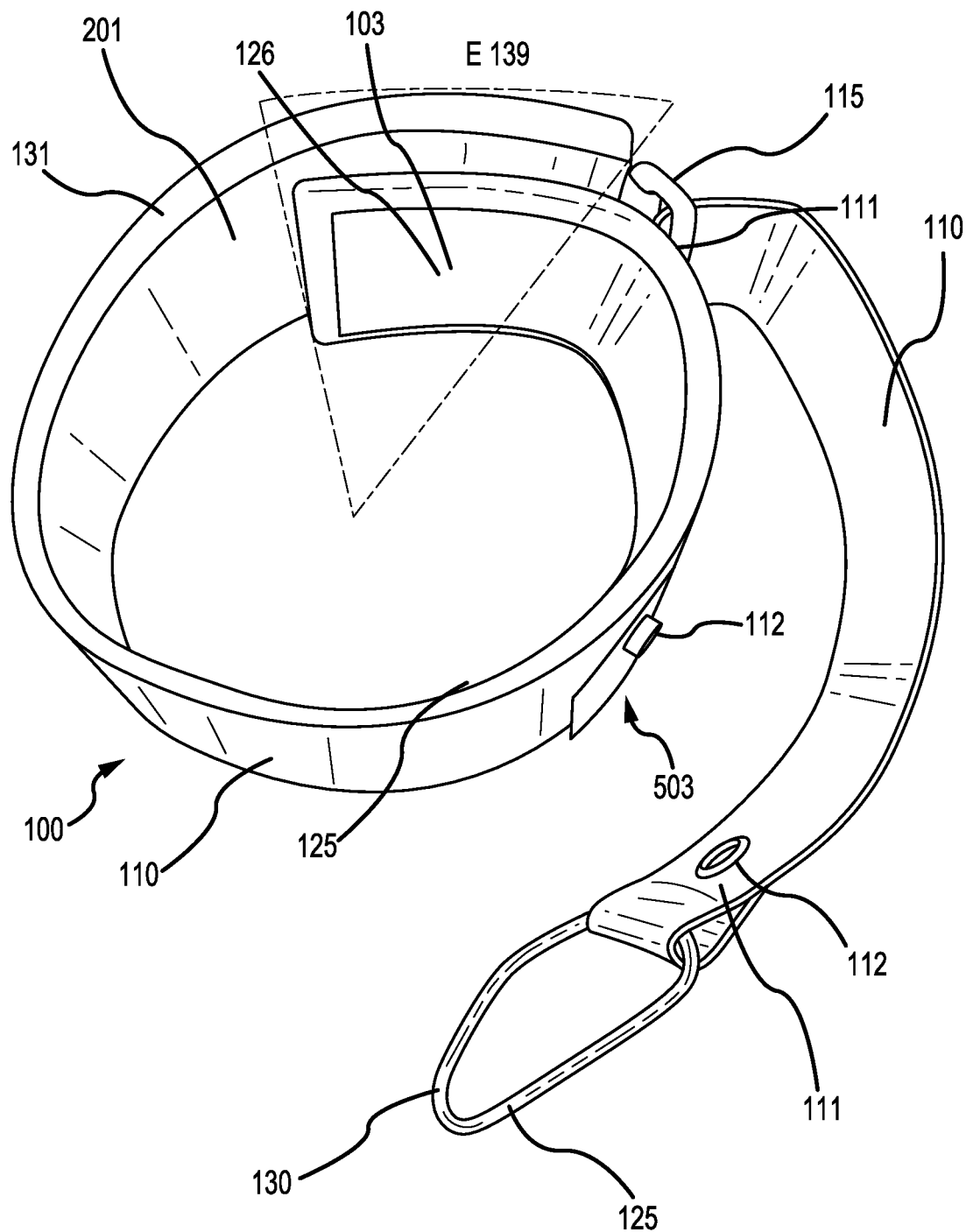
FIG. 14D—shows a prototype inflatable belt built around the design aspects of FIG. 14C, further incorporating color identification and reflective features.

FIG. 14C further shows a perspective view of the adjustable distance measuring and positive locking system 1400 as adapted to the inflatable belt 100 of a linked inflatable chamber concept as described in the provisional applications incorporated herein in full by reference. FIG. 14D shows a physical prototype that was constructed with this design. The inflatable belt 100 contains similar key features such as input port 104, inner belt material 101, and outer belt material 102. The notable difference is that instead of a second fastening means 111 connected to the end of the first fastening means 110, a positive locking means 1404 is placed in communication with the first fastening means. Consequently, a positive lock adjustment 1403, containing the mating part of the positive locking means 1404 is placed at a length along the first fastening means 110 as shown in FIG. 14C. The specific location of the positive lock adjustment 1403 is made as previously described either with incorporation of a distance indicator 1402 on the inflatable belt 100 itself or measuring with an external distance indicator such as a ruler.

FIG. 14C is a good example of a fold back style belt and illustrates how the adjustable distance measuring and positive locking system 1400 can be adapted to one of the many embodiments described in this, and the previously filed, provision applications.

FIG. 14D illustrates a physical prototype of the combination discussed above with a few notable features. First, the overlap length 139 concept, represented by E, is clearly illustrated to show how an inflatable bladder 103 can overlap itself to accommodate users with smaller limb girths. Second, a coloring element in the form of handle 130, is shown to make identification of sizes simple and quick, which is important in a facility that uses lots of belts. Third, optional reflective edging 131, is employed to assist safety for users who want to do BFR training outside in dark conditions such as running on the side of the road. Finally, an optional piece of second fastening means 111 is fixed around the positive locking means 1404 on the first fastening means 110 and adjacent to the handle 130. This optional second fastening means 111 serves a function that the user can still tighten and use the inflatable belt 100 should they lose the lock from positive lock adjustment 1403. Similarly, in a situation where the inflatable belt 100 is to be used by an expert on lots of clients one after another, it may be cumbersome to stop and measure the initial tension settings for each user. Further, the instructor is likely well experienced by that time to get the initial tension approximately correct without need of the distance measuring and positive locking system 1400 and this it is not necessary. Indeed, even an individual user will become familiar with the feel and may not need to use this prescribed distance more than the first few times. By including this optional second fastening means 111, all users and usage characteristics may be accommodated.

Figure 14E:
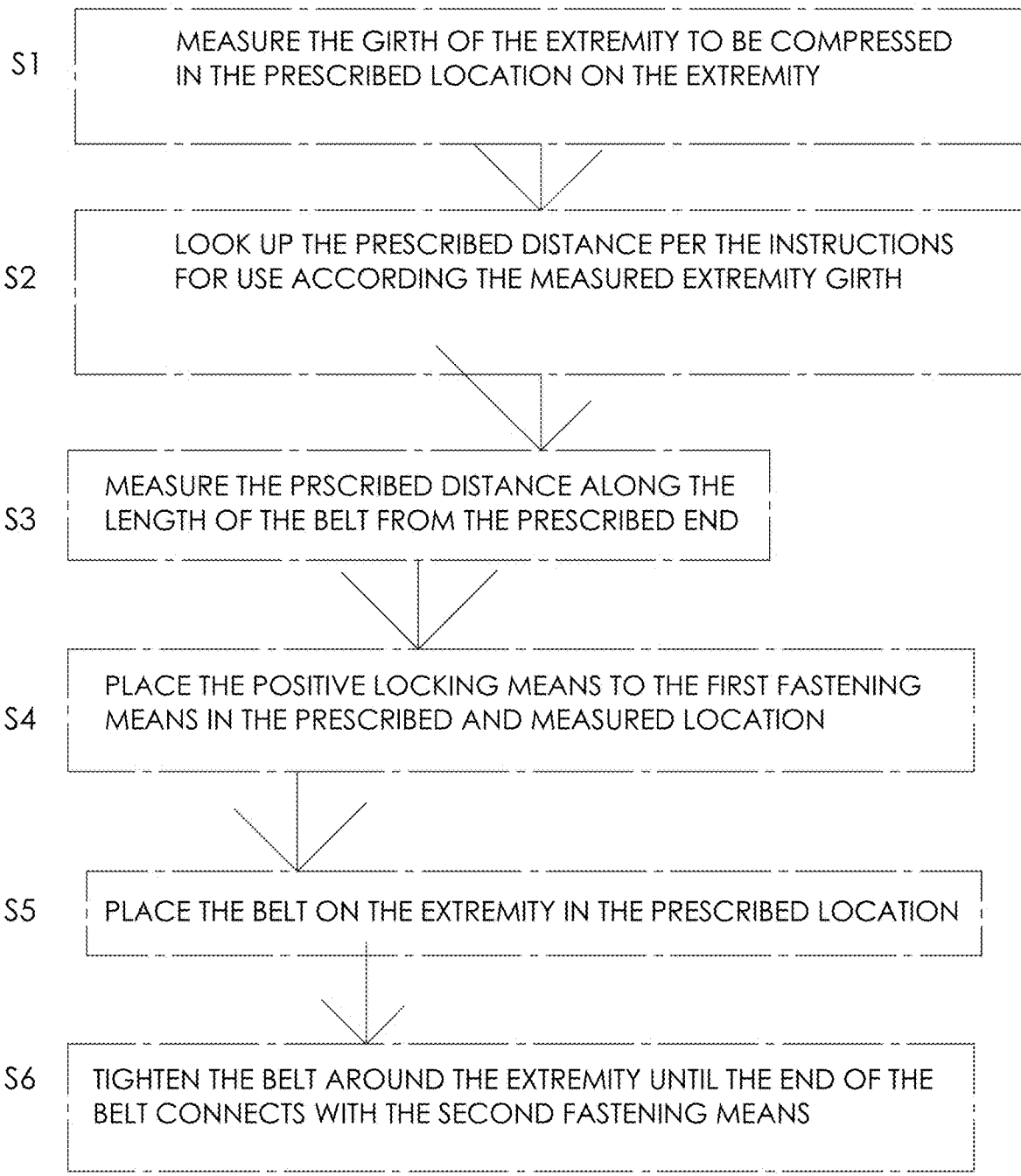
FIG. 14E—shows a step flow chart describing how a user takes advantage of the distance measuring and locking concept shown in FIGS. 14A-D.

FIG. 14E illustrates a sample procedure by which the distance measuring and positive locking system 1400 may be used. First, the user in S1 measures the girth of the extremity in the location where they desire to place the inflatable belt 100. Next, S2, the user looks up a prescribed distance in a provided table as to where along the length of the belt they should place the positive lock adjustment 1403 based on their limb girth measurement. Then, S3, the user measures the location of where to place the positive lock adjustment 1403, or uses a provided distance indicator 1402, and places the positive lock adjustment on the outer surface of the first fastening means 110 (S4). Then, (S5) the user takes the end of the belt with the mating positive locking means 1404 and pulls the belt tight such that the two positive locking means (one on the first fastening means 110 and one on the end of the belt) mate up and lock the belt in a circumference (S6). Therein, the inflatable belt 100 is fixed at a prescribed distance appropriate for the specific girth of the body segment they are securing to.

Finally it is important to stress again the importance of getting the initial tension precise and correct, which is the objective of the distance measuring and positive locking system 1400. Too loose initial tensions in the belts lead to ineffective BFR Training because the compression, albeit largely insensitive to initial positioning in the case of the design herein, may simply not have enough shrinkage and chamber expansion to apply adequate compression. Contrarily, too tight initial tension in the belts can lead to blood flow occlusion and unsafe operating conditions. All current art and research studies either ignore the concept all together, or use subjective measures of "feel" in order to instruct users how to tension existing belts. This is typically either sub-optimal or unsafe, and the applicant's invention solves these issues with a prescriptive system based on limb circumference that allows a user to very precisely, accurately, and repeatedly set the initial tension of the inflatable belt 100 around the limb prior to inflation.

Figure 15:
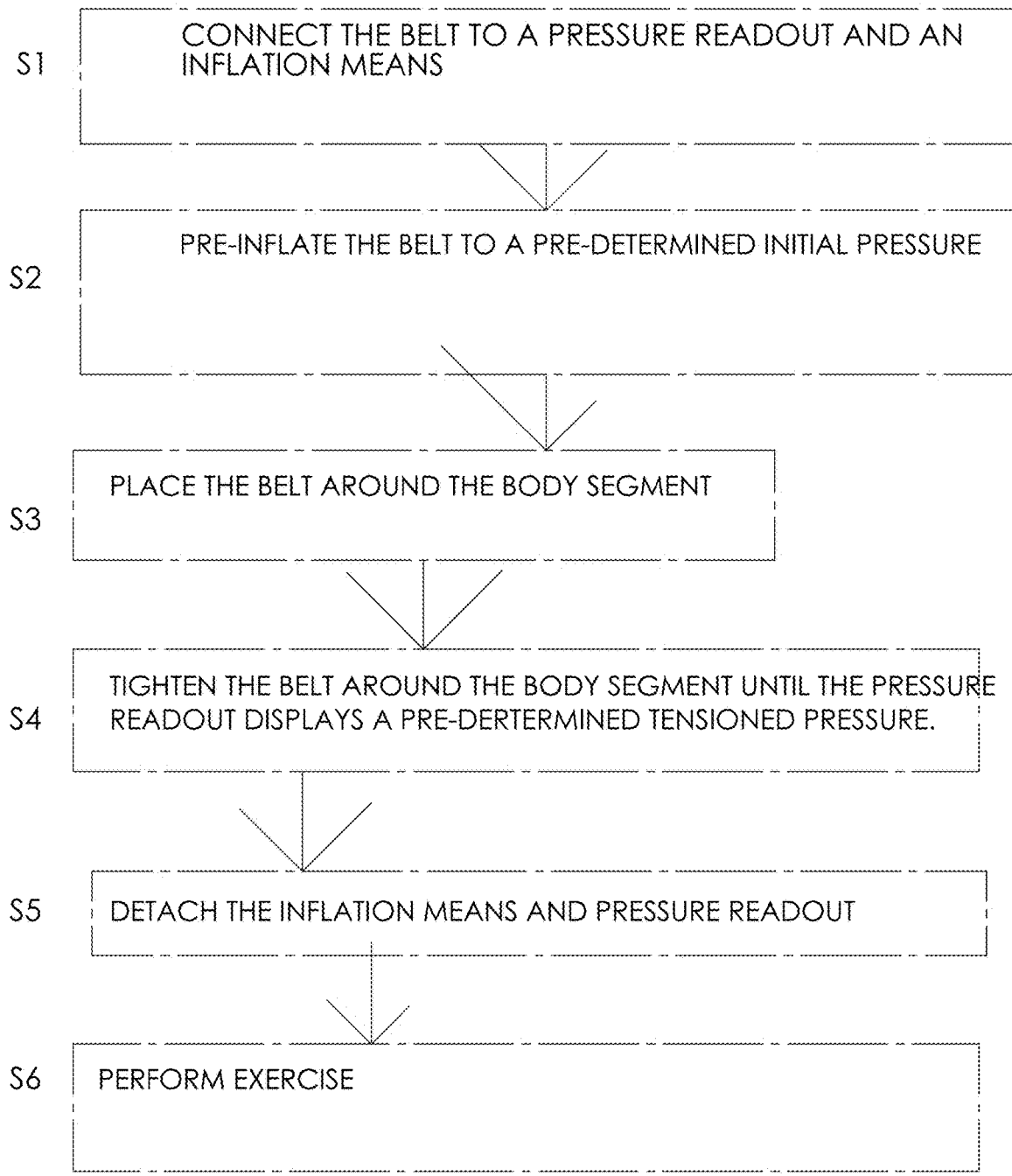
FIG. 15—shows a step flow chart describing use of an inflatable belt.

Alternate Embodiment—#25. Referring to FIG. 15, another concept for prescribing an initial tension is described that does not require additional components but only takes advantage of the properties of the inflatable belt 100, and manipulation of the pressure inside to repeatedly set an initial pre-determined tension around a body segment. The reader shall note that this method may be employed with the applications inventions or any other invention in the prior art.

In S1, the inflatable belt 100 is left off the body segment and simply connected to an inflation means 106 and a pressure readout 703 as has been shown in prior embodiments. The reader shall not the connections may be permanent, or semi-permanent, as has been previously discussed and S1 may not be necessary.

In S2, the inflatable belt 100 is pre-inflated to an initial pressure while not on the body segment. The initial pressure may be 50 mm Hg for example, but any appreciable pressure may suffice for the purposes of illustrating this method.

In S3, the inflatable belt 100 is wrapped around a body segment, to which it will be secured.

In S4, the inflatable belt 100 is tensioned around the body segment while the pressure readout 703 is monitored, and tension increased until the pressure readout reaches a pre-determined tensioned pressure. The reader shall note may such tensioning methods and mechanisms for holding, increasing, releasing tension have been disclosed in this application and the prior art and shall be applicable to this method. S4 substantially terminates the process of setting an initial belt tension around a body segment that will be consistent from one session to the next and does not require additional fasteners, distance indicators, etc as long as the initial pressure and the tensioned pressure remain consistent. Both variables may be prescribed for a specific limb girth so that the user does not need to guess, or experiment, but rather can get this data from a profile or lookup table and operate without having to think much. As Sato describes, simplifying BFR training, is imperative to widespread adoption.

In S5, the inflation means 106 and pressure readout 703 may be disconnected from the inflatable 100, but in the case these components are permanently connected, this step may be omitted.

Finally, in S6, the user now has a belt secured to their body segment at a prescribed, pre-determined tension and may start to move.

KAATSU teaches an initial pressure setting protocol consisting of placing the belt on the limb and then inflating and reading a readout. This method is overly cumbersome in that if the pressures are not as they should be the applicant must remove the belt, re-adjust it, and re-inflate to the initial pressure. This process could be iterative and is not real-time, so the applicants inventive method will be significantly faster and requires no re-adjustment, saving time and frustration.

The reader will see that the various inventions described herein, provide an economical way to easily create a multifunctional, safe, inexpensive, easy to use blood flow restriction system and inflatable belt for incorporation therein. Additionally the reader will see that inventions described herein may take advantage of current mass production processes to keep the additional cost minimal, and that by reducing component count, the applicant has not only reduced the manufacturing costs but also the level of complexity of operating the system, and the bulk of the system which, since it is a wearable product to be used during exercise, is a significant factor as Sato himself describes. The reader has also provided for improved initial tensioning of the belt, which improves consistency, the prescriptive nature, and the safety to avoid over tensioning and risk of occlusion of blood flow.

While the above description contains specificities, these should not be construed as limitations on the scope of the invention, but rather as an exemplification of preferred embodiments thereof. Many other variations are possible.

Belt Shapes/Sizes

For example, in the case of inflatable belt shape, the inflatable portion of the belt may be of any suitable geometry, size and shape to provide sufficient blood flow restriction as discussed above. Belts may come in multiple lengths and widths to accommodate a range of individuals, and not necessarily minimized in the number of variations, but rather targeted toward a specific range of limb girths, or user types. It may be noted that wider cuffs have been shown to restrict flow to the same extent at lower pressures and may offer more comfort for certain applications that don't require dynamic movements. Such width variations for a specific user, such as assisting the elderly, may improve comfort while maintaining effectiveness. Belt shapes which employ enough tissue displacement to restrict venous return, such as some examples described herein, may be used, and may not necessarily cover the entire limb. All such configurations of profiles, sizes of belts, gas bladders, locations placements of such belts on the body, and bladders on belts, may be considered within the scope of this application.

Belt Materials

Various belt and blood flow restriction system designs have been described herein, and various material constructions and configurations have likewise been disclosed. Various components being elastic, and relative degrees of elasticity have further been noted. The reader may not that for the sake of brevity, not all such combinations and material types have been discussed, but all such combinations, material properties or configurations may be considered within the scope of this invention. For example, in the case of the fastening means, cam-locks, ratchets, and hook and loop fasteners have been described, however many other such means of fastening two objects together may be used such as a high friction joint tri-glide style mechanism, glues or adhesives, ropes or knots, mechanical hooks, buttons, racks and pinions, high friction surfaces, etc may be consider encompassed within the term fastening means and this term interpreted as broadly as possible. Further, in the case of elastic members or fabrics, polyurethane coated fabrics may be substituted for PVC coated fabrics or a similar material, and urethane molds, but be of latex rubber, or similar material. In all such cases where specific materials are called out, the readers may understand that, this specification is but one example, and as long as the general concept described is achieved, the specific material, or specific property thereof, is not a requirement of the invention.

Materials described similarly may be understood to encompass combinations of materials, varying material properties such as durometer or elastic modulus, lengths and widths, and profiles, which effect properties such as elasticity and coefficient of friction, may be considered within the scope of this invention. For example, where a material is deemed to be of a certain degree of elasticity, the reader may note that all materials have some elastic properties, and what is important is the function of the material as described herein. Further the readers may note that where a material may be discussed as elastic, a non-elastic material may be combined with an elastic material to form what would be considered the original member (or visa-versa), but which is now two components and may not specifically match the description herein. However, in such cases, the readers may note that the applicant has in fact considered that materials may be combined to perform the function of the elements of the inventions described herein, but has not made all such descriptions because of the endless possible combinations possible. For example the belt spring disclosed may consist of an elastic webbing sewn to an inelastic tail, or may comprise an elastic material, sewn to an in-elastic material, sewn to another even more elastic material. All such combinations yield the same result as originally disclosed that the belt spring member has some degree of elasticity. Yet another example is the reader may note that some element properties may be altered to remove various components. For example the inflatable belt may have some degree of elasticity in order to compensate for muscle contraction, and therefore render the belt spring unnecessary. Again, the reader may note that all such combinations or omissions of components, or altering of various component properties may be considered within the scope of this invention.

Valves

Further, various valves have been disclosed and discussed herein relating to quick connect coupling valves, pressure relief valves, manual release valves, electromechanical valves, having gas glow shutoffs, not having gas flow shutoffs etc. The readers may recognize that there are many incarnations of all these kinds of valves including mechanisms, materials, fabrication technique, sizes, port designs, connections means, etc. For example, a coupling valve may be configured for quick connect with locking means, such as a clasp, or break away means, or screw type, as some limited examples. The coupling valve may have a shutoff means to trap gas upon disconnection one or both sides of the coupling valve, and the shutoff means may be any of such know mechanism including, but not limited to, duckbill valve, spring plunger, etc. Pressure relief valves and manual release valves similarly come in many shapes, sizes, materials, such as spring loaded, adjustable, non-adjustable, etc. Manual release valves further may be plunger style, screw on and off, pull tab release, rip cord release, etc. Electromechanical valves may be motor actuated, solenoid valves, or any other such valve that employs electric current to open and close. The reader may further note that any combination of such valves into a single housing and design may prove advantageous for manufacturing and cost savings. A few designs are disclosed herein, but represent only a few of many such combinations and design variations. Therefore, reader may understand the basic concept of a belt that needs to receive air into at some point, either multiple times, or one time in a factory, and the belt is therefore connected to an inflation means at least once in its lifetime. In the case where the belt needs to be inflated and deflated, one or more valves must be used to allow air into the belt, but prevent air from escaping until deemed appropriate by the user. Valves, or valve features, such as pressure limiting capability, may be further added to the system, either permanently, or semi-permanently as previously discussed in the preferred embodiment, or removable and connectable to the inflatable belt, as proves most advantageous, and as long as the belt has enough air to perform sufficient blood flow restriction, and satisfactorily maintains this air during the training procedure, any and all combinations of valve quantities, types, features, etc. shall be deemed considered and within the scope of the herein disclosed inventions. Valves may further be made to be adjustable or left non-adjustable, and specific configuration may be the most appropriate for a given belt design.

User

The user in the context of this application may be deemed to mean the person using the inventions described. This may be a client, patient, instructor, personal user, doctor, athletic trainer, coach, etc.

Electromechanical Function

The application has disclosed various modes of operation of an electromechanical system for controlling inflation pressure in the inflatable belts with electromechanical valves and manual inflation means. The reader shall note that while the manual inflation means yields certain advantages as discussed herein, inflation means may also be electromechanical as described in the prior art. Further, the applicant has disclosed various procedures of how such manual plus electromechanical systems function, but the reader shall note that various steps may be omitted, or repeated to yield desired effects, and various additional sensors may be added to further augment such systems. For example, instead of holding the electromechanical valve open at the end of a protocol, the system may hold it closed and wait for a signal from the user, for example a shake that is sensed by an accelerometer (not shown), to wake up from a sleep mode and open the valve. This would save battery power for example. Many such variations and sensor combinations may be disclosed in further applications. Another example is the various timers may be omitted and simply wait for a user to disconnect the inflation means and hold whatever pressure is inside. Or there may be input means to adjust the pressure during the protocol. Data may not be sent to the microcontroller to set a pressure, and this may just be a preset factory setting for example. Active pressure regulation may be added, instead as described in FIG. 9, where the pressure goes above a target, and then is dropped until it is below the target, and not inflated any more. Active pressure regulation may allow the user to add a little more air into the system to further get closer to the target, or in the case of fully automated system, may add it the air itself. Workout timers may also be ignored, and while it adds an element of safety, it is not an essential feature to illustrate how an manual plus electromechanical system can function in a similar way to a fully manual system. The reader may note the many combinations and features may be added or omitted and still the core inventions disclosed and claimed herein may be considered to encompass all such iterations.

General

One skilled in the art will recognized any minor modifications that would be needed for such an intermingling and such modifications may be considered within the scope of this specification and claims. Further, it may be recognized that many of the components described may be combined into a single object via different manufacturing processes such as welding, injection molding, casting, etc. While the applicant discusses some of these options briefly in the application, it may be recognized any and all combinations of the components discussed herein may be considered within the scope of this application and covered by the claims written. Similarly, it may be recognized that many components in the system and their connection points, or connection means, may also be interchanged or rearranged to achieve the same effect as the disclosed configurations. For example, where it is discussed that it may be advantageous to de-couple the inflation means from the inflatable belt, and a pressure relief valve is used to limit a maximum pressure in the belt, the pressure relief valve may reside either on the belt side of the coupling or the inflation means side of the coupling. In the case of residing on the belt side of the coupling, then no further shutoff mechanism is necessary on the belt side of the coupling. However, the invention will function substantially the same if the coupling employs a shutoff function to keep air in the belt, which is opened during connection of the inflation means, and the pressure relief valve is on the inflation means side of the coupling. In such a case, as long as the inflation means is connected, the pressure relief valve is in the same air-circuit as the belt, and limits the pressure therein. Upon disconnection however the pressure relief valve is not connected in the air-circuit of the belt, however neither is the inflation means and thus there is no risk of too high pressures accumulating in the belt. Thus the system is substantially similar in both cases. This is but one example, and in general, valves, and valve types, fastening means, such as cam locks, hook and loop fasteners, ratchet style mechanisms, belt springs, inner and outer belt materials etc. may be interchanged, used in quantities of more than one, altered in width, length, or profile, employed in conjunction of overlapping belt styles, or doubling back of belt styles for locking, or more complicated belt designs such as those shown in patents to Sato, and the inventions disclosed herein may be considered to have encompassed all such permutations and combinations of such components. Yet another example is the inflatable belt may have two input ports, one to allow air in and another in communication with an outlet system such as a pressure relief valve. While such design is not shown in the figures above, the reader may note this concept is another example of how multiple items may be employed, and components shifted within the system to connect with different components, while the same overall system and effectiveness is maintained. Further still, the location and placement of various elements may be moved and altered such that they appear to differ from the figures shown, and description attached, however, all such configurations and combinations may be considered within the scope of the inventions disclosed herein. For example, in the case of the hook and loop fastener shown on the inflatable belt in FIG. 1K, the hook and loop fastener may be exchanged and the function still maintained. In addition, the location of the input port may be in the middle of the inflatable belt instead of on one end. The body interface component, such as neoprene rubber, shown in FIG. 1 E may be permanently attached the inflatable bladder, or it may be removable. If removable, the attachment means may be for example, hook and loop fasteners, and the fasteners may be along the edges as shown in FIG. 1A, B or may run along the full width of both the inflatable bladder and body interface component. In the case the hook and loop fasteners run along the full width, they may be elastic such that the inflatable bladder may still inflate against the user's limb. As illustrated, there are many constructional permutations and combinations, and altering of various material properties which yield satisfactory results in an inflatable belt for use in a blood flow restriction system, and all such combinations and permutations and material property choices may be considered within the scope of this invention.

Belt Configurations

As has been discussed in both this application and patents to Sato, there are a variety of ways to form a belt around a user's limb and each has some advantages and disadvantages as discussed in the various applications. The reader may recognize that the inventive concepts disclosed herein may be considered adaptable, by changing, but limited to, the following: size, length, location, neighboring components, adding or removing one or more components, such as a loop coupler, material property, such as elasticity, etc. Such modifications represent numerous permutations and configurations which are too many to reasonably depict and describe herein, however the reader may understand that the applicant has thought of such reasonable applications, and may consider as such, part of the scope of this disclosed invention.

Purpose of Inflatable Belts

The previous discussion has extensively covered the use of the applicant's invention and inflatable belt 100 design in the context of a muscle development tool used for BFR training. However the applicant would like to point out that the generic construction can be useful for wrapping anything tight against the body, and not necessarily for the purpose of restricting blood flow.

Some purposes for this could be affixing, or otherwise integrating the design to clothing to pull a section of clothing tight against the arm, leg, or even waist as in a traditional belt. Such consideration may be useful for example in conjunction with an unweighting system where it is often difficult to have garments grab, or adhere to the body as a vertical force is applied. In this circumstance, the applications invention may serve to aid in wrapping or grabbing onto a body in order to lock and provide an anchor off of which to pull. The belt could be applied external to the garment or integrated into the garment, for example a pair of shorts, or a shirt. The shrinking belt portion may warp around the chest, or waist, or arms, or any part of the body so as to fulfill its purpose. Any sort of lifting or force transfer apparatus may be connected to the belt itself, or to a structure that is connected to the belt, such that the load is eventually transferred to the body in such a way that the belt helps with efficient and comfortable load transfer.

Another example may be applying compression in the case of a wrapping an ice bag or heating pad to the limb. In these cases, it is often difficult to get a good wrap on the limb, or requires a lot of plastic to wrap around in order to stay in place when the person stands up or wants to move from one spot to another. In these cases, a fast inflating sleeve that sounds an ice bag or heating pad, and that secures it tight to a limb may be particularly useful for quick on/off, and without wasting materials such as plastic wrap that is commonly used.

In any of these, or related use cases, the reader shall understand that all the designs, aspects, characteristics, methods, and inventions described in this application shall be applicable to such use cases, and this generic concept of securing a belt to a body segment make take advantage of the inventions described in this specification and the provided claims.

Although the description above contains many specifications, these should not be construed as limiting the scope of the invention but as merely providing illustrations of some of the presently preferred embodiments of this invention. Thus the scope of this invention should be determined by the appended claims and their legal equivalents, rather than by the examples given.

What is claimed is:

1. A belt for securing to a body segment, the belt comprising:
    an inner belt material;
    an outer belt material, wherein the inner belt material has a higher degree of elasticity than the outer belt material, wherein the inner belt material and the outer belt material are connected along a perimeter to form a substantially airtight gas bladder for accepting a gas;
    an input port in communication with the gas bladder, wherein the input port comprises a tube heat sealed between the inner belt material and the outer belt material;
    a belt fastening means for fastening the belt around the body segment, wherein the belt fastening means comprises a first fastening means associated with a first end of the belt and a second fastening means associated with a second end of the belt, and the first fastening means is attachable to the second fastening means to limit an initial circumference of the belt when wrapped around the body segment, and wherein the belt fastening means comprises elastic properties;
    at least one body interfacing component configured to locate the belt exterior to the body segment by a distance of at least about 1.5 mm and less than about 5 mm prior to inflation of the gas bladder, wherein the at least one body interfacing component comprises neoprene;
    a loop coupler associated with an end of the belt;
    a stop mechanism associated with one of the first fastening means or the second fastening means which prevents the associated fastening means from exiting the loop coupler, keeping the belt in a substantially ring-like shape;
    a positive locking means in communication with the first fastening means; and
    a positive lock adjustment at a length along the first fastening means.

2. The belt of claim 1, wherein the stop mechanism comprises a bar which mechanically interferes with the loop coupler.

3. The belt of claim 1, further comprising an inflation means that is non-removable and in communication with the belt and wherein the inflation means comprises an electromechanical pump.

4. The belt of claim 3, wherein the belt further comprises a microprocessor, wherein:
    the microprocessor is configured to store instructions for the electromechanical pump,
    the microprocessor is configured to communicate with the electromechanical pump,
    the microprocessor is configured to receive instructions from an external computer, and
    the external computer comprises a PC, phone, or tablet.

5. The belt of claim 4, wherein the microprocessor is configured to receive instructions from the external computer via a wireless communication means.

6. The belt of claim 4, wherein the microprocessor is configured to receive user feedback.

7. The belt of claim 1, wherein the outer belt material is machine washable, wherein the inner belt material comprises polyurethane coated nylon stretch fabric, wherein the body segment is a limb, and wherein the gas bladder is configured to cover at least 30% of a user's limb circumference.

8. The belt of claim 7, wherein the gas bladder is not configured to cover the user's entire limb circumference, and wherein the gas bladder is configured to only apply compression to a specific region on the limb.

9. The belt of claim 7, wherein a length of the gas bladder is equal to the length of the smallest limb circumference of the expected user such that the gas bladder never overlaps itself.

10. The belt of claim 1, wherein the belt further comprises a pressure readout device, and an automated pressure relief mechanism, wherein:
    the automated pressure relief mechanism comprises a pressure limiting valve, wherein the automated pressure relief mechanism is combined with a manual relief mechanism to form a pressure relief valve combo;
    the automated pressure relief mechanism comprises an adjustable cap which is configured to compress a spring which in turn pushes a pressure relief plunger to sandwich an o-ring between the pressure relief plunger and a pressure relief valve body to create an airtight seal;
    and
    the pressure readout device is in communication with a gas hose in between the automated pressure relief mechanism and an inflation means.

11. The belt of claim 1, wherein the belt is configured to produce an obstruction or impediment to deep venous flow coming out of the body segment.

12. The belt of claim 1, wherein the at least one body interfacing component is removable.

13. The belt of claim 1, wherein the gas bladder comprises a first circumference at a first edge of the gas bladder and a second circumference at a second edge of the gas bladder, wherein the first circumference is greater than the second circumference.

14. The belt of claim 1, wherein the gas bladder comprises additional anti roll features on either side configured to prevent the belt from moving on the user's limb during inflation, muscle contraction, and exercise.

15. The belt of claim 1, wherein the belt further comprises notched markings, and wherein the notched markings correspond to a pre-calculated table that links specific body segment girths with a specific notched marking.

16. The belt of claim 1, wherein the belt further comprises reflective edging.

* * * * *